(12) United States Patent
Sinai et al.

(10) Patent No.: US 9,549,798 B2
(45) Date of Patent: Jan. 24, 2017

(54) APPARATUSES FOR THE AMELIORATION OF URINARY INCONTINENCE IN FEMALES

(71) Applicant: Kimberly-Clark Worldwide, Inc., Neenah, WI (US)

(72) Inventors: Nir Sinai, Alon HaGalil (IL); Elan Ziv, Ramat-Gan (IL); Idan Buder, Mitzpe Gilon (IL); Jacob Gilan, Binyamina (IL); Meital Vaknin, Kiryat-Shmona (IL); Eliahu Eliachar, Haifa (IL); Yohanan Maggeni, Ilania (IL)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 175 days.

(21) Appl. No.: 14/078,586

(22) Filed: Nov. 13, 2013

(65) Prior Publication Data

US 2014/0073846 A1 Mar. 13, 2014

Related U.S. Application Data

(63) Continuation of application No. 11/886,248, filed as application No. PCT/IL2006/000346 on Mar. 16, 2006, now Pat. No. 8,617,047, which is a continuation-in-part of application No. PCT/IL2005/000304, filed on Mar. 17, 2005.

(60) Provisional application No. 60/719,422, filed on Sep. 22, 2005, provisional application No. 60/762,059, filed on Jan. 25, 2006.

(51) Int. Cl.
*A61F 2/00* (2006.01)
*A61B 17/00* (2006.01)

(52) U.S. Cl.
CPC ............ *A61F 2/0009* (2013.01); *A61F 2/005* (2013.01); *A61B 2017/00805* (2013.01)

(58) Field of Classification Search
CPC ........... A61F 2/005; A61F 2/0004; A61F 6/08
USPC ................ 128/897, 834–837; 600/29–32, 37
See application file for complete search history.

(56) References Cited

U.S. PATENT DOCUMENTS

| | | | |
|---|---|---|---|
| 2,141,040 A | 12/1938 | Holt |
| 2,146,574 A | 2/1939 | Hay |
| 2,432,768 A | 12/1947 | Kurkjian |
| 2,938,519 A | 5/1960 | Marco |

(Continued)

FOREIGN PATENT DOCUMENTS

| | | |
|---|---|---|
| DE | 271657 | 3/1914 |
| DE | 19816349 | 10/1999 |

(Continued)

OTHER PUBLICATIONS

European Search Report and the European Search Opinion Dated Nov. 14, 2013 From the European Patent Office Re. Application No. 11188150.4.

(Continued)

*Primary Examiner* — Samuel Gilbert
(74) *Attorney, Agent, or Firm* — Kimberly-Clark Worldwide, Inc.

(57) ABSTRACT

An apparatus for treating urinary incontinence with a support section adapted for providing urethral support; an anchoring section for resisting movement of the apparatus; an insert, a portion of which is adapted to be positioned where the support section attaches to the node; and, wherein the insert urges the support section radially outwards from a central axis of the apparatus.

7 Claims, 34 Drawing Sheets

(56) References Cited

U.S. PATENT DOCUMENTS

| | | | |
|---|---|---|---|
| 3,138,159 A | 6/1964 | Schmidt | |
| 3,646,929 A | 3/1972 | Bonnar | |
| 3,683,906 A | 8/1972 | Robinson | |
| 3,789,828 A | 2/1974 | Schulte | |
| 3,797,478 A | 3/1974 | Walsh et al. | |
| 3,841,304 A | 10/1974 | Jones | |
| 4,019,498 A | 4/1977 | Hawtrey | |
| 4,019,499 A | 4/1977 | Fitzgerald | |
| 4,139,006 A | 2/1979 | Corey | |
| 4,142,649 A | 3/1979 | Forgey | |
| 4,212,301 A | 7/1980 | Johnson | |
| 4,307,716 A * | 12/1981 | Davis | A61F 6/08 128/834 |
| 4,428,365 A | 1/1984 | Hakky | |
| 4,457,299 A | 7/1984 | Cornwell | |
| 4,553,533 A | 11/1985 | Leighton | |
| 4,726,805 A | 2/1988 | Sanders | |
| 4,823,814 A | 4/1989 | Drogendijk et al. | |
| 4,846,784 A | 7/1989 | Haber | |
| 4,850,963 A | 7/1989 | Sparks et al. | |
| 4,920,986 A | 5/1990 | Biswas | |
| 5,007,894 A | 4/1991 | Enhorning | |
| 5,014,722 A | 5/1991 | Bauer | |
| 5,036,867 A | 8/1991 | Biswas | |
| 5,041,077 A | 8/1991 | Kulick | |
| 5,090,424 A | 2/1992 | Simon et al. | |
| 5,224,493 A | 7/1993 | Sawan et al. | |
| 5,224,494 A | 7/1993 | Enhorning | |
| 5,336,208 A | 8/1994 | Rosenbluth et al. | |
| 5,352,182 A | 10/1994 | Kalb et al. | |
| 5,370,657 A | 12/1994 | Irie | |
| 5,386,836 A | 2/1995 | Biswas | |
| 5,417,226 A | 5/1995 | Juma | |
| 5,483,976 A | 1/1996 | McLaughlin et al. | |
| 5,603,685 A | 2/1997 | Tutrone, Jr. | |
| 5,609,586 A | 3/1997 | Zadini et al. | |
| 5,618,256 A | 4/1997 | Reimer | |
| 5,659,934 A | 8/1997 | Jessup et al. | |
| 5,671,755 A | 9/1997 | Simon et al. | |
| 5,724,994 A | 3/1998 | Simon et al. | |
| 5,755,906 A | 5/1998 | Achter et al. | |
| 5,771,899 A | 6/1998 | Martelly et al. | |
| 5,782,745 A | 7/1998 | Benderev | |
| 5,785,640 A | 7/1998 | Kresch et al. | |
| 5,788,664 A | 8/1998 | Scalise | |
| 5,795,346 A | 8/1998 | Achter et al. | |
| 5,894,842 A | 4/1999 | Rabin et al. | |
| 6,013,023 A | 1/2000 | Klingenstein | |
| 6,090,038 A | 7/2000 | Zunker et al. | |
| 6,090,098 A | 7/2000 | Zunker et al. | |
| 6,142,928 A | 11/2000 | Zunker et al. | |
| 6,158,435 A | 12/2000 | Dorsey | |
| 6,189,535 B1 | 2/2001 | Enhorning | |
| 6,216,698 B1 | 4/2001 | Regula | |
| 6,251,122 B1 | 6/2001 | Tsukernik | |
| 6,413,206 B2 | 7/2002 | Biswas | |
| 6,415,484 B1 | 7/2002 | Moser | |
| 6,418,930 B1 | 7/2002 | Fowler | |
| 6,428,467 B1 | 8/2002 | Benderev | |
| 6,458,072 B1 | 10/2002 | Zunker | |
| 6,460,542 B1 | 10/2002 | James | |
| 6,461,215 B1 | 10/2002 | Kunz et al. | |
| 6,478,726 B1 | 11/2002 | Zunker | |
| 6,503,190 B1 | 1/2003 | Ulmsten et al. | |
| 6,558,370 B2 | 5/2003 | Moser | |
| 6,645,136 B1 | 11/2003 | Zunker et al. | |
| 6,676,594 B1 | 1/2004 | Zunker et al. | |
| 6,679,831 B1 | 1/2004 | Zunker et al. | |
| 6,739,340 B1 | 5/2004 | Jensen et al. | |
| 6,770,025 B2 | 8/2004 | Zunker | |
| 6,808,485 B2 | 10/2004 | Zunker | |
| 7,036,511 B2 | 5/2006 | Nissenkorn | |
| 7,717,892 B2 | 5/2010 | Bartning et al. | |
| 7,931,671 B2 | 4/2011 | Tenerz | |
| 8,435,168 B2 | 5/2013 | Ziv et al. | |
| 2002/0068023 A1 | 6/2002 | Davis | |
| 2002/0083949 A1 | 7/2002 | James | |
| 2002/0115906 A1 | 8/2002 | Miller | |
| 2002/0120243 A1 | 8/2002 | Kraemer et al. | |
| 2002/0138035 A1 | 9/2002 | Hull, Jr. | |
| 2002/0156341 A1 | 10/2002 | Zunker | |
| 2002/0156343 A1 | 10/2002 | Zunker | |
| 2002/0183711 A1 | 12/2002 | Moser | |
| 2003/0149334 A1 * | 8/2003 | Ulmsten | A61F 2/005 600/29 |
| 2003/0149392 A1 | 8/2003 | Arnould | |
| 2004/0054252 A1 | 3/2004 | Zunker | |
| 2004/0078013 A1 | 4/2004 | Zunker et al. | |
| 2004/0084054 A1 | 5/2004 | Kaseki et al. | |
| 2004/0122285 A1 | 6/2004 | Zunker | |
| 2004/0158122 A1 | 8/2004 | Guerquin | |
| 2004/0199100 A1 | 10/2004 | LeMay et al. | |
| 2005/0016545 A1 | 1/2005 | Nissenkorn | |
| 2006/0100475 A1 | 5/2006 | White et al. | |
| 2007/0088189 A1 | 4/2007 | Levy | |
| 2007/0203429 A1 | 8/2007 | Ziv | |
| 2007/0244352 A1 | 10/2007 | Ziv | |
| 2008/0149109 A1 | 6/2008 | Ziv | |
| 2008/0281149 A1 | 11/2008 | Sinai et al. | |
| 2009/0266367 A1 | 10/2009 | Ziv et al. | |
| 2009/0283099 A1 | 11/2009 | Harmanli | |
| 2011/0065980 A1 | 3/2011 | Ziv et al. | |
| 2012/0271098 A1 | 10/2012 | Ziv et al. | |
| 2013/0165743 A1 | 6/2013 | Ziv et al. | |

FOREIGN PATENT DOCUMENTS

| | | |
|---|---|---|
| EP | 0264258 | 4/1988 |
| EP | 0274762 | 7/1988 |
| EP | 0 933 069 A1 | 8/1988 |
| EP | 0700669 | 3/1996 |
| EP | 0921778 | 6/1999 |
| EP | 0955024 | 11/1999 |
| EP | 1139963 | 10/2001 |
| EP | 1139962 | 5/2005 |
| EP | 1727491 | 12/2006 |
| FR | 2843700 | 2/2004 |
| GB | 1115727 | 5/1968 |
| GB | 2352181 | 1/2001 |
| GB | 2384436 | 7/2003 |
| JP | 63-177852 | 7/1988 |
| JP | 06-133996 A | 5/1994 |
| JP | 61-33996 | 5/1994 |
| JP | 09-501595 | 2/1997 |
| JP | 2001-502929 | 3/2001 |
| JP | 2002-532198 A | 2/2002 |
| JP | 2002-5332199 | 10/2002 |
| WO | WO 88/10106 | 12/1988 |
| WO | WO 89/09582 | 10/1989 |
| WO | WO 95/05790 | 3/1995 |
| WO | WO 96/01084 | 1/1996 |
| WO | WO 97/34550 | 9/1997 |
| WO | WO 98/49980 | 11/1998 |
| WO | WO 00/03659 | 1/2000 |
| WO | WO 00/36996 | 6/2000 |
| WO | WO 00/67662 | 11/2000 |
| WO | WO 02/26160 | 4/2002 |
| WO | WO 02/089704 | 11/2002 |
| WO | WO 03/047476 | 6/2003 |
| WO | WO 04/000433 | 12/2003 |
| WO | WO 2004/103213 | 12/2004 |
| WO | WO 2005/087153 | 9/2005 |
| WO | WO 2005/087154 | 9/2005 |
| WO | WO 2006/097935 | 9/2006 |
| WO | WO 2008/010214 | 1/2008 |
| WO | WO 2008/079271 | 7/2008 |
| WO | WO 2008/152628 | 12/2008 |

(56) References Cited

FOREIGN PATENT DOCUMENTS

WO   WO 2009/044394   4/2009
WO   WO 2009/130702   10/2009

OTHER PUBLICATIONS

Applicant-Initiated Interview Summary Dated Aug. 9, 2013 From the US Patent and Trademark Office Re. U.S. Appl. No. 12/680,575.
Applicant-Initiated Interview Summary Dated Jun. 28, 2013 From the US Patent and Trademark Office Re. U.S. Appl. No. 12/680,575.
Communication Pursuant to Article 94(3) EPC Dated Nov. 3, 2011 From the European Patent Office Re. Application No. 07789949.0.
Communication Pursuant to Article 94(3) EPC Dated Feb. 4, 2011 From the European Patent Office Re. Application No. 04734069.0.
Communication Pursuant to Article 94(3) EPC Dated Apr. 16, 2009 From the European Patent Office Re.: Application No. 05718876.5.
Communication Pursuant to Article 94(3) EPC Dated Mar. 23, 2010 From the European Patent Office Re.: Application No. 05718876.5.
Communication Pursuant to Rules 70(2) and 70a(2) EPC Dated Nov. 8, 2013 From the European Patent Office Re. Application No. 06711327.4.
Communication Relating to the Results of the Partial International Search Dated Mar. 3, 2011 From the International Searching Authority Re. Application No. PCT/IL2010/000985.
Communication Relating to the Results of the Partial International Search Dated Dec. 7, 2007 From the International Searching Authority Re.: Application No. PCT/IL2007/000893.
Communication Relating to the Results of the Partial International Search Dated Jan. 12, 2009 From the International Searching Authority Re.: Application No. PCT/IL2008/001292.
Communication Relating to the Results of the Partial International Search Dated Aug. 18, 2009 From the International Searching Authority Re.: Application No. PCT/IL2009/000443.
Communication Under Rule 112 EPC Dated Oct. 22, 2007 From the European Patent Office Re.: Application No. 05718876.5.
Communication Under Rule 71(3) EPC Dated May 27, 2011 From the European Patent Office Re. Application No. 09735573.9.
Communiction Pursuant to Article 94(3) EPC Dated Jul. 2, 2010 From the European Patent Office Re.: Application No. 05718877.3.
Communiction Pursuant to Article 94(3) EPC Dated Apr. 16, 2009 From the European Patent Office Re.: Application No. 05718877.3.
Decision to Refuse a European Patent Application Dated Feb. 25, 2013 From the European Patent Office Re. Application No. 04734069.0.
European Search Report Under Rule 112 EPC Dated Dec. 27, 2007 From the European Patent Office Re.: Application No. 05718876.5.
Examination Report Dated Oct. 13, 2010 From the Instituto Mexicano de la Propiedad Industrial Re. Application No. MX/a/2007/011339 and Its Summary in English.
Examination Report Dated Oct. 13, 2011 From the Instituto Mexicano de la Propiedad Industrial Re. Application No. MX/a/2007/011339 and Its translation Into English.
Examination Report Dated Feb. 16, 2012 From the Government of India, Patent Office, Intellectual Property Building Re. Application No. 3837/CHENP/2006.
Examination Report Dated Jan. 16, 2012 From the Instituto Mexicano de la Propriedad Industrial Re. Application No. PA/a/2006/010653 and Its Summary in English.
Examination Report Dated May 30, 2012 From the Instituto Mexicano de la Propiedad Industrial Re. Application No. MX/a/2007/011339 and Its Translation Into English.
Examination Report Dated Mar. 31, 2011 From the Instituto Mexicano de la Propiedad Industrial Re. Application No. MX/a/2007/011339.
Examiner-Initiated Interview Summary Dated Oct. 10, 2012 From the US Patent and Trademark Office Re. U.S. Appl. No. 12/680,575.
Examiner's Report Dated Dec. 9, 2009 From the Australian Government, IP Australia Re.: Application No. 2005221424.

Examiner's Report Dated Dec. 15, 2010 From the Australian Government, IP Australia Re.: Application No. 2005221424.
Examiner's Report Dated Nov. 29, 2010 From the Australian Government, IP Australia Re. Application No. 2006224158.
International Preliminary Report on Patentability Dated Jul. 6, 2006 From the International Preliminary Examining Authority Re.: Application No. PCT/IL2005/000304.
International Preliminary Report on Patentability Dated Jun. 7, 2012 From the International Bureau of WIPO Re. Application No. PCT/IL2010/000985.
International Preliminary Report on Patentability Dated Dec. 1, 2009 From the International Preliminary Examining Authority Re.: Application No. PCT/IL2008/001292.
International Preliminary Report on Patentability Dated Oct. 14, 2008 From the International Preliminary Examining Authority Re.: Application No. PCT/IL06/00346.
International Preliminary Report on Patentability Dated Jul. 15, 2010 From the International Preliminary Examining Authority Re.: Application No. PCT/IL2009/000443.
International Preliminary Report on Patentability Dated Dec. 23, 2009 From the International Bureau of WIPO Re.: Application No. PCT/IL2008/000786.
International Preliminary Report on Patentability Dated Jul. 24, 2006 From the International Preliminary Examining Authority Re.: Application No. PCT/IL2005/000303.
International Preliminary Report on Patentability Dated Jan. 29, 2009 From the International Bureau of WIPO Re.: Application No. PCT/IL2007/000893.
International Search Report and the Written Opinion Dated May 9, 2011 From the International Searching Authority Re. Application No. PCT/IL2010/000985.
International Search Report and the Written Opinion Dated Oct. 26, 2005 From the International Searching Authority Re.: Application No. PCT/IL2005/000303.
International Search Report and the Written Opinion Dated Oct. 28, 2009 From the International Searching Authority Re.: Application No. PCT/IL2009/000443.
International Search Report Dated Dec. 11, 2006 From the International Searching Authority Re.: Application No. PCT/IL06/00346.
International Search Report Dated Apr. 14, 2008 From the International Searching Authority Re.: Application No. PCT/IL2007/000893.
International Search Report Dated Sep. 23, 2005 From the International Searching Authority Re.: Application No. PCT/IL2005/000304.
International Search Report. Dated Oct. 24, 2008 From the International Searching Authority Re.: Application No. PCT/IL2008/000786.
International Search Report Dated Mar. 25, 2009 From the International Searching Authority Re.: Application No. PCT/IL2008/001292.
Interview Summary Dated Feb. 9, 2011 From the US Patent and Trademark Office Re.: U.S. Appl. No. 10/593,367.
Letter After Telephone Conference Dated Jul. 5, 2010 From the International Searching Authority Re. Application No. PCT/IL2009/000443.
Notice of Acceptance Dated Feb. 2, 2011 From the Australian Government, IP Australia Re.: Application No. 2005221424.
Notice of Allowance Dated Oct. 2, 2013 From the US Patent and Trademark Office Re. U.S. Appl. No. 12/417,011.
Notice of Allowance Dated Aug. 6, 2013 From the US Patent and Trademark Office Re. U.S. Appl. No. 11/886,248.
Notice of Allowance Dated Jan. 7, 2013 From the US Patent and Trademark Office Re. U.S. Appl. No. 12/373,937.
Notice of Allowance Dated Nov. 14, 2011 From the US Patent and Trademark Office Re.: U.S. Appl. No. 10/593,367.
Notice of Allowance Dated Mar. 31, 2010 From the US Patent and Trademark Office Re.: U.S. Appl. No. 10/557,865.
Notification Dated Dec. 17, 2008 From the Patent Office of the Russian Federation Re.: Application No. 2006136791 and Its translation Into English.

(56) References Cited

OTHER PUBLICATIONS

Notification of Reasons for Rejection Dated Oct. 4, 2013 From the Japanese Patent Office Re. Application No. 2011-223943 and Its Translation Into English.
Notification of Reasons for Rejection Dated Feb. 18, 2011 From the Japanese Patent Office Re. Application No. 2007-503494 and Its Translation into English.
Office Action Dated Sep. 1, 2008 From the Israeli Patent Office Re.: Application No. 156070 and Its Translation Into English.
Office Action Dated Sep. 1, 2008 From the Israeli Patent Office Re.: Application No. 157117 and Its Translation Into English.
Office Action Dated Apr. 5, 2011 From the Israel Patent Office Re.: Application No. 156070 and Its Translation Into English.
Office Action Dated Dec. 5, 2012 From the Israel Patent Office Re. Application No. 176883 and Its Translation Into English.
Office Action Dated Jan. 9, 2009 From the State Intellectual Property Office of the People's Republic of China Re.: Application No. 200580016245.2 and Its Translation Into English.
Office Action Dated Jan. 18, 2010 From the Israel Patent Office Re.: Application No. 156070 and Its Translation Into English.
Office Action Dated Jul. 24, 2011 From the Israel Patent Office Re. Application No. 176883 and Its Translation Into English.
Official Action Dated Jul. 1, 2013 From the US Patent and Trademark Office Re. U.S. Appl. No. 12/663,714.
Official Action Dated Aug. 4, 2010 From the US Patent and Trademark Office Re.: U.S. Appl. No. 10/598,872.
Official Action Dated Sep. 5, 2008 From the US Patent and Trademark Office Re.: U.S. Appl. No. 10/557,865.
Official Action Dated Mar. 6, 2009 From the US Patent and Trademark Office Re.: U.S. Appl. No. 10/557,865.
Official Action Dated May 6, 2013 From the US Patent and Trademark Office Re. U.S. Appl. No. 11/886,248.
Official Action Dated Apr. 9, 2012 From the US Patent and Trademark Office Re. U.S. Appl. No. 12/417,011.
Official Action Dated Mar. 12, 2013 From the US Patent and Trademark Office Re. U.S. Appl. No. 12/680,575.
Official Action Dated Oct. 12, 2010 From the US Patent and Trademark Office Re. U.S. Appl. No. 10/598,872.
Official Action Dated Feb. 14, 2011 From the US Patent and Trademark Office Re.: U.S. Appl. No. 10/598,872.
Official Action Dated Oct. 14, 2011 From the US Patent and Trademark Office Re. U.S. Appl. No. 12/417,011.
Official Action Dated Feb. 15, 2012 From the US Patent and Trademark Office Re. U.S. Appl. No. 12/373,937.
Official Action Dated Oct. 15, 2009 From the US Patent and Trademark Office Re.: U.S. Appl. No. 10/557,865.
Official Action Dated Apr. 17, 2009 From the Patent Office of the Russian Federation Re.: Application No. 2006136791 and Its Translation Into English.
Official Action Dated Feb. 19, 2010 From the US Patent and Trademark Office Re.: U.S. Appl. No. 10/593,367.
Official Action Dated Jun. 21, 2011 From the US Patent and Trademark Office Re.: U.S. Appl. No. 10/593,367.
Official Action Dated Jul. 23, 2012 From the US Patent and Trademark Office Re. U.S. Appl. No. 12/373,937.
Official Action Dated Jul. 23, 2013 From the US Patent and Trademark Office Re. U.S. Appl. No. 10/598,872.
Official Action Dated Jun. 23, 2010 From the US Patent and Trademark Office Re.: U.S. Appl. No. 10/593,367.
Official Action Dated Aug. 24, 2012 From the US Patent and Trademark Office Re. U.S. Appl. No. 11/886,248.
Official Action Dated Sep. 24, 2013 From the US Patent and Trademark Office Re. U.S. Appl. No. 13/772,410.
Official Action Dated Oct. 27, 2009 From the Federal Institute of Industrial and Intellectual Property, Patents and Trademarks, ROSPATENT, of the Russian Federation Re.: Application No. 2007138489 and Its Translation Into English.
Official Action Dated Dec. 28, 2010 From the US Patent and Trademark Office Re.: U.S. Appl. No. 10/593,367.
Official Action Dated Apr. 29, 2010 From the US Patent and Trademark Office Re.: U.S. Appl. No. 10/598,872.
Official Action Dated May 31, 2011 From the US Patent and Trademark Office Re. U.S. Appl. No. 12/417,011.
Patent Examination Report Dated Aug. 9, 2012 From the Australian Government, IP Australia Re. Application No. 2007274574.
Request for Examination Dated Apr. 4, 2013 From the Federal Service for Intellectual Property, Federal State Budgetary Institution, Federal Institute of Industrial Property of the Russian Federation Re. Application No. 2010146714 and Its Summary in English.
Request for Examination Dated Jun. 11, 2010 From the Federal Institute of Industrial and Intellectual Property, Patents and Trademarks, ROSPATENT, of the Russian Federation Re.: Application No. 2010100368 and Its Summary in English.
Request for Examination Dated Mar. 29, 2012 From the Federal Institute of Industrial and Intellectual Property, Patents and Trademarks, ROSPATENT, of the Russian Federation Re.: Application No. 2010100368 and Its Summary in English.
Requisition by the Examiner Dated Feb. 19, 2013 From the Canadian Intellectual Property Office Re. Application No. 2,560,877.
Requisition by the Examiner Dated Aug. 22, 2012 From the Canadian Intellectual Property Office Re. Application No. 2,600,988.
Requisition by the Examiner Dated May 22, 2012 From the Canadian Intellectual Property Office Re. Application No. 2,560,877.
Requisition by the Examiner Dated May 28, 2013 From the Canadian Intellectual Property Office Re. Application No. 2,600,988.
Requisition by the Examiner Dated Aug. 29, 2011 From the Canadian Intellectual Property Office Re. Application No. 2,560,877.
Response Dated Aug. 1, 2010 to Notification of Reasons of Rejection Dated Apr. 8, 2010 From the Japanese Patent Office Re.: Application No. 2007-503494.
Response Dated Jun. 1, 2011 to Notification of Reasons for Rejection of Mar. 18, 2011 From the Japanese Patent Office Re. Application No. 2006-531002.
Response Dated Nov. 3, 2010 to Communication Pursuant to Article 94(3) EPC of Jul. 2, 2010 From the European Patent Office Re. Application No. 057188877.3.
Response Dated Jun. 5, 2011 to the Communication Pursuant to Article 94(3) EPC of Feb. 4, 2011 From the European Patent Office Re. Application No. 04734069.0.
Response Dated Aug. 7, 2011 to Office Action of Apr. 5, 2011 From the Israel Patent Office Re.: Application No. 156070.
Response Dated Dec. 8, 2010 to Examiner's Report of Dec. 9, 2009 From the Australian Government, IP Australia Re.: Application No. 2005221424.
Response Dated Aug. 10, 2011 to Official Action of May 31, 2011 From the US Patent and Trademark Office Re. U.S. Appl. No. 12/417,011.
Response Dated Mar. 10, 2011 to Notification of Reasons for Rejection of Dec. 24, 2010 From the Japanese Patent Office Re. Application No. 2007-503495.
Response Dated Aug. 11, 2011 to Examination Report of Mar. 31, 2011 From the Instituto Mexicano de la Propiedad Industrial Re. Application No. MX/a/2007/011339.
Response Dated Jan. 12, 2011 to Examination Report of Oct. 13, 2010 From the Instituto Mexicano de la Propiedad Industrial Re. Application No. MX/a/2007/011339.
Response Dated Jan. 13, 2011 to Official Action of Oct. 12, 2010 From the US Patent and Trademark Office Re.: U.S. Appl. No. 10/598,872.
Response Dated Jun. 14, 2011 to Official Action of Feb. 14, 2011 From the US Patent and Trademark Office Re.: U.S. Appl. No. 10/598,872.
Response Dated Mar. 15, 2010 to Official Action of Oct. 15, 2009 From the US Patent and Trademark Office Re.: U.S. Appl. No. 10/557,865.
Response Dated Nov. 16, 2010 to Office Action of Sep. 17, 2010 From the State Intellectual Property Office of the People's Republic of China Re.: Application No. 200680017262.2.

(56) References Cited

OTHER PUBLICATIONS

Response Dated Jan. 17, 2011 to Examiner's Report of Dec. 15, 2010 From the Australian Government, IP Australia Re.: Application No. 2005221424.
Response Dated Oct. 19, 2011 to Official Action of Jun. 21, 2011 From the US Patent and Trademark Office Re.: U.S. Appl. No. 10/593,367.
Response Dated Jun. 20, 2011 to Office Action of Dec. 21, 2010 From the State Intellectual Property Office of the People's Republic of China Re. Application No. 200780033622.2.
Response Dated Oct. 20, 2010 to Official Action of Jun. 11, 2010 From the Federal Institute of Industrial and Intellectual Property, Patents and Trademarks, ROSPATENT, of the Russian Federation Re.: Application No. 2010100368.
Response Dated Jun. 21, 2010 to Office Action of Jan. 29, 2010 From the State Intellectual Property Office of the People's Republic of China Re.: Application No. 200680017262.2.
Response Dated Feb. 22, 2010 to International Search Report and the Written Opinion of Oct. 28, 2009 From the International Searching Authority Re.: Application No. PCT/IL2009/000443.
Response Dated Mar. 25, 2010 to Official Action of Feb. 19, 2010 From the US Patent and Trademark Office Re.: U.S. Appl. No. 10/593,367.
Response Dated Oct. 25, 2010 to Official Action of Jun. 23, 2010 From the US Patent and Trademark Office Re.: U.S. Appl. No. 10/593,367.
Response Dated Dec. 27, 2009 to Official Action of Oct. 29, 2009 From the Federal Institute of Industrial and Intellectual Property, Patents and Trademarks, ROSPATENT, of the Russian Federation Re.: Application No. 2007138489.
Response Dated Mar. 28, 2011 to Official Action of Dec. 28, 2010 From the US Patent and Trademark Office Re.: U.S. Appl. No. 10/593,367.
Response Dated Nov. 28, 2011 to Examiner's Report of Nov. 29, 2010 From the Australian Government, IP Australia Re. Application No. 2006224158.
Response Dated Jun. 29, 2010 to Official Action of Apr. 29, 2010 From the US Patent and Trademark Office Re.: U.S. Appl. No. 10/598,872.
Response Dated Jun. 29, 2011 to Office Action of Apr. 29, 2011 From the State Intellectual Property Office of the People's Republic of China Re.: Application No. 200680017262.2.
Response Dated May 29, 2011 to Communication Pursuant to Article 94(3) EPC of Feb. 4, 2011 From the European Patent Office Re. Application No. 04734069.0.
Response Dated Aug. 30, 2010 to Notification of Reasons for Rejection of Jun. 1, 2010 From the Japanese Patent Office Re. Application No. 2006-531002.
Response Dated Sep. 30, 2010 to Communication Pursuant to Article 94(3) EPC of Mar. 23, 2010 From the European Patent Office Re.: Application No. 05718876.5.
Response Dated Aug. 31, 2010 to Official Action of Aug. 4, 2010 From the US Patent and Trademark Office Re.: U.S. Appl. No. 10/598,872.
Restriction Official Action Dated Nov. 1, 2012 From the US Patent and Trademark Office Re. U.S. Appl. No. 12/680,575.
Restriction Official Action Dated Feb. 6, 2013 From the US Patent and Trademark Office Re. U.S. Appl. No. 12/663,714.
Restriction Official Action Dated Feb. 28, 2012 From the US Patent and Trademark Office Re. U.S. Appl. No. 11/886,248.
Second Supplemental Notice of Allowability Dated Jun. 3, 2010 From the US Patent and Trademark Office Re.: U.S. Appl. No. 10/557,865.
Supplemental Notice of Allowability Dated Apr. 2, 2013 From the US Patent and Trademark Office Re. U.S. Appl. No. 12/373,937.
Supplemental Notice of Allowability Dated Sep. 24, 2013 From the US Patent and Trademark Office Re. U.S. Appl. No. 11/886,248.
Supplemental Notice of Allowability Dated Apr. 27, 2010 From the US Patent and Trademark Office Re.: U.S. Appl. No. 10/557,865.
Supplementary European Search Report and the European Search Opinion Dated Oct. 21, 2013 From the European Patent Office Re. Application No. 06711327.4.
Translation of Decision for Rejection Dated Jun. 9, 2011 From the Japanese Patent Office Re. Application No. 2007-503495.
Translation of Notification of Reasons for Rejection Dated Jun. 1, 2010 From the Japanese Patent Office Re. Application No. 2006-531002.
Translation of Notification of Reasons for Rejection Dated Mar. 18, 2011 From the Japanese Patent Office Re. Application No. 2006-531002.
Translation of Notification of Reasons for Rejection Dated Dec. 24, 2010 From the Japanese Patent Office Re. Application No. 2007-503495.
Translation of Notification of Reasons of Rejection Dated Apr. 8, 2010 From the Japanese Patent Office Re.: Application No. 2007-503494.
Translation of Office Action Dated Mar. 5, 2013 From the State Intellectual Property Office of the People's Republic of China Re. Application No. 200980123856.5.
Translation of Office Action Dated May 6, 2013 From the State Intellectual Property Office of the People's Republic of China Re. Application No. 200780033622.2.
Translation of Office Action Dated Dec. 21, 2010 From the State Intellectual Property Office of the People's Republic of China Re. Application No. 200780033622.2.
Translation of Office Action Dated Aug. 22, 2013 From the State Intellectual Property Office of the People's Republic of China Re. Application No. 200780033622.2.
Translation of Office Action Dated Feb. 22, 2012 From the State Intellectual Property Office of the People's Republic of China Re. Application No. 200780033622.2.
Translation of Office Action Dated Nov. 22, 2012 From the State Intellectual Property Office of the People's Republic of China Re. Application No. 200780033622.2.
Translation of Office Action Dated Apr. 29, 2011 From the State Intellectual Property Office of the People's Republic of China Re.: Application No. 200680017262.2.
Translation of Office Action Dated Jan. 29, 2010 From the State Intellectual Property Office of the People's Republic of China Re.: Application No. 200680017262.2.
Translation of Reasons for Rejection Dated Mar. 18, 2013 From the Japanese Patent Office Re. Application No. 2011-223943.
Translation of Search Report Dated Nov. 22, 2012 From the State Intellectual Property Office of the People's Republic of China Re. Application No. 200780033622.2.
Written Opinion Dated Dec. 11, 2006 From the International Searching Authority Re.: Application No. PCT/IL06/00346.
Written Opinion Dated Apr. 14, 2008 From the International Searching Authority Re.: Application No. PCT/IL2007/000893.
Written Opinion Dated Nov. 22, 2005 From the International Searching Authority Re.: Application No. PCT/IL2004/000433.
Written Opinion Dated May 23, 2006 From the International Preliminary Examining Authority Re.: Application No. PCT/IL2005/000303.
Written Opinion Dated Sep. 23, 2005 From the International Searching Authority Re.: Application No. PCT/IL2005/000304.
Written Opinion Dated Oct. 24, 2008 From the International Searching Authority Re.: Application No. PCT/IL2008/000786.
Written Opinion Dated Mar. 25, 2009 From the International Searching Authority Re.: Application No. PCT/IL2008/001292.
Communication Pursuant to Article 94(3) EPC Dated Nov. 29, 2013 From the European Patent Office Re. Application No. 08808093.2.
Office Action Dated Nov. 12, 2013 From the State Intellectual Property Office of the People's Republic of China Re. Application No. 200980123856.5 and Its Translation Into English.
Invitation Pursuant to Rule 62a(1) EPC dated Aug. 8, 2013 from the European Patent Office re: Application No. 06711327.4.
Translation of Office Action dated Sep. 17, 2010 from the State Intellectual Property Office of the People's Republic of China re: Application No. 200680017262.2.

* cited by examiner

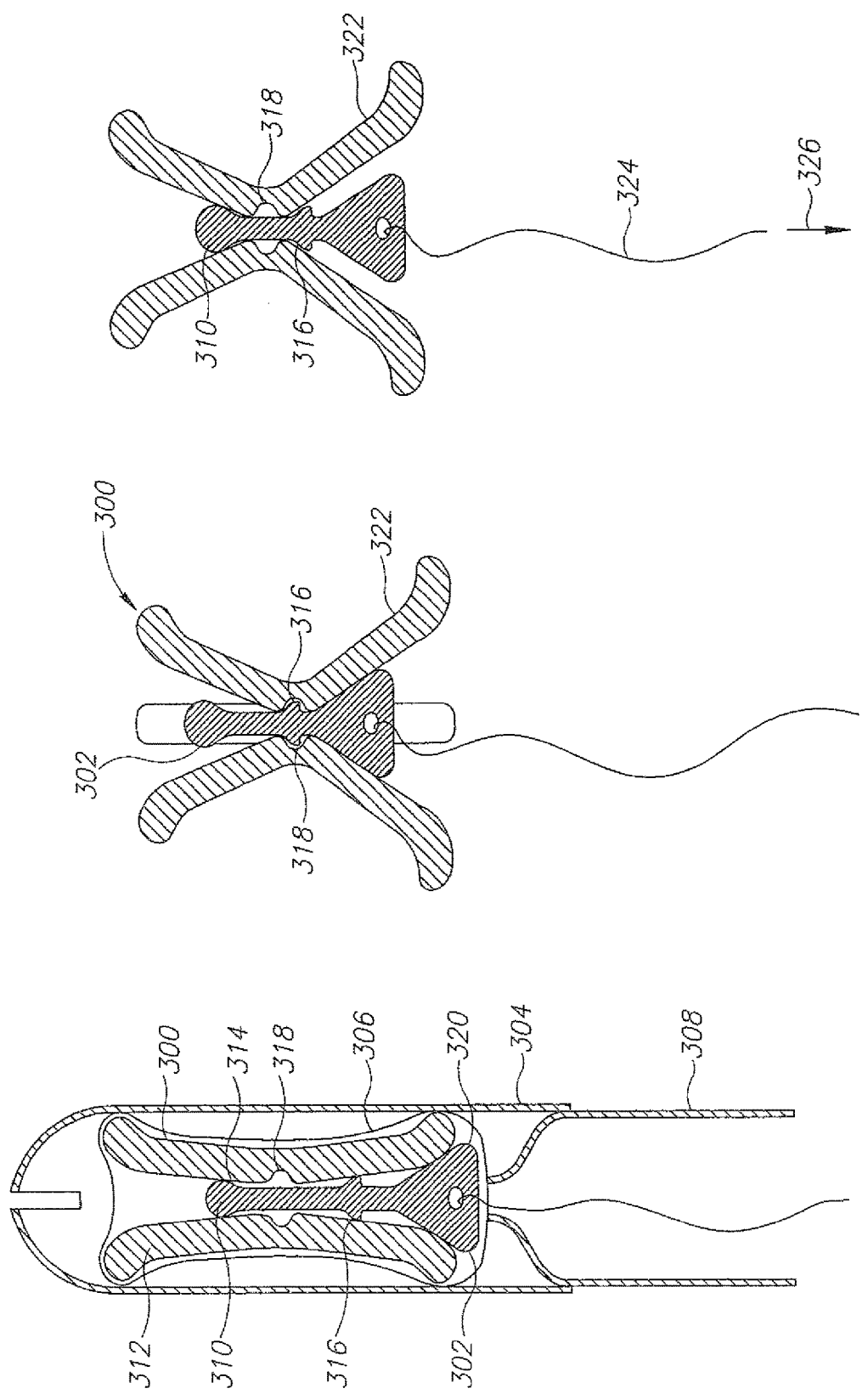

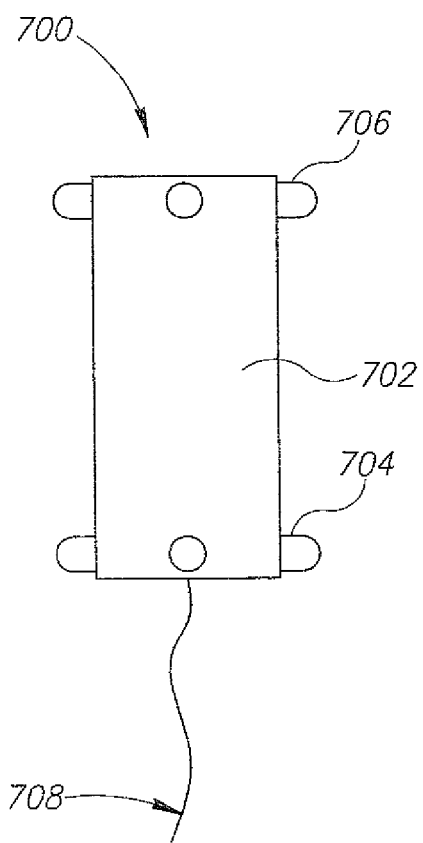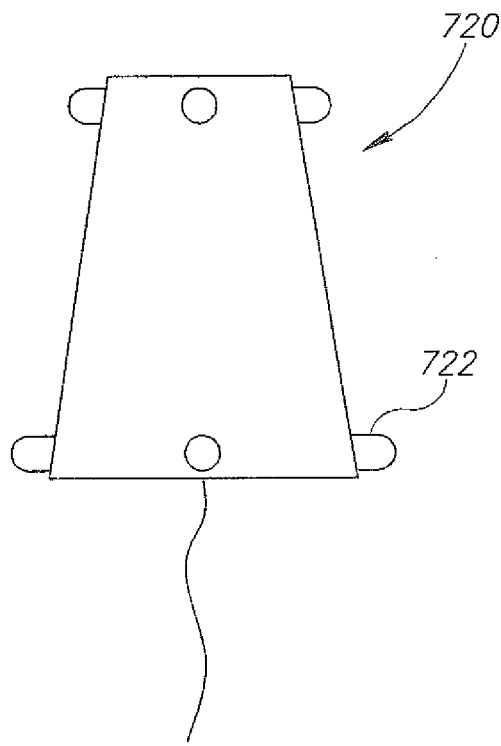
FIG.7A  FIG.7B
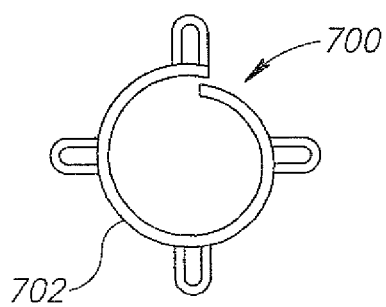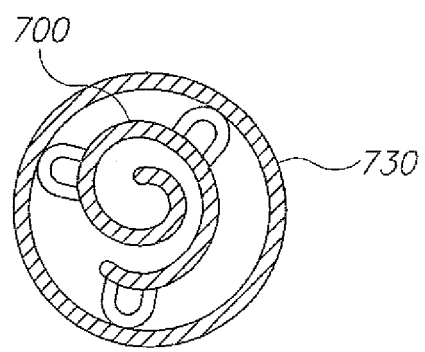
FIG.7C  FIG.7D

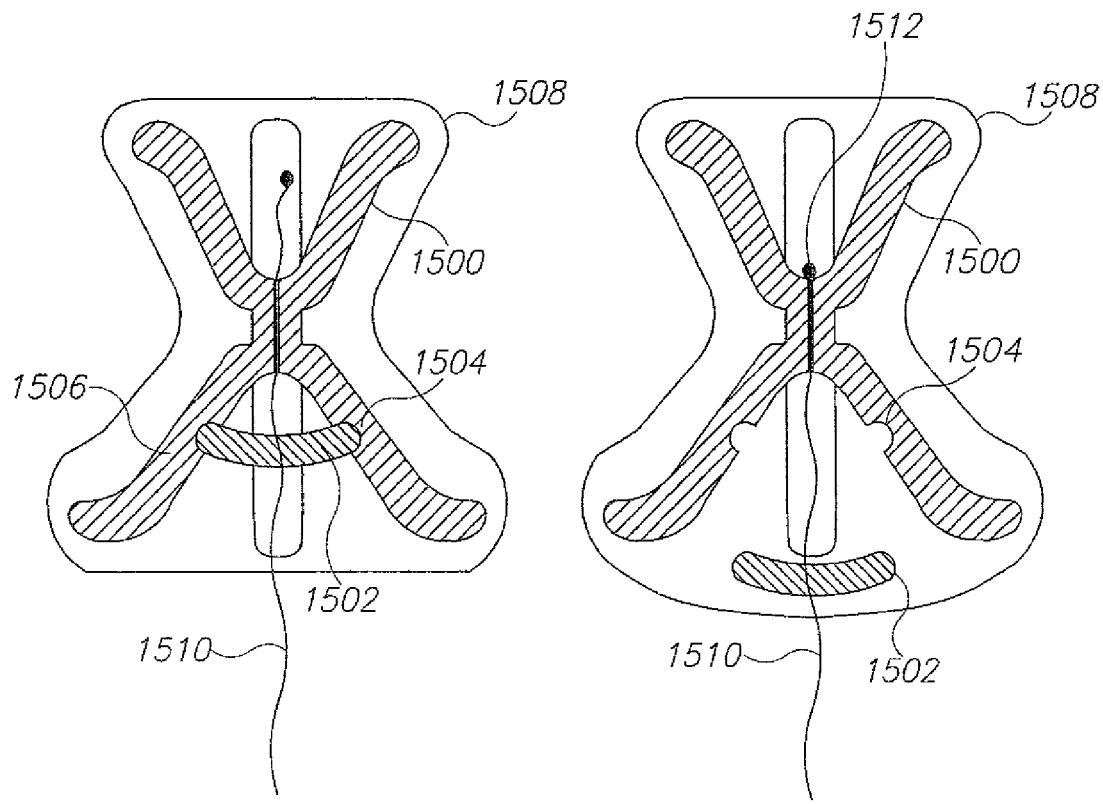
FIG.15A  FIG.15B
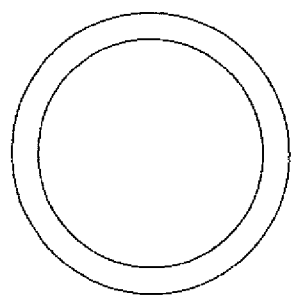 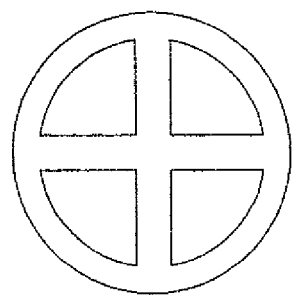
FIG.15C  FIG.15D

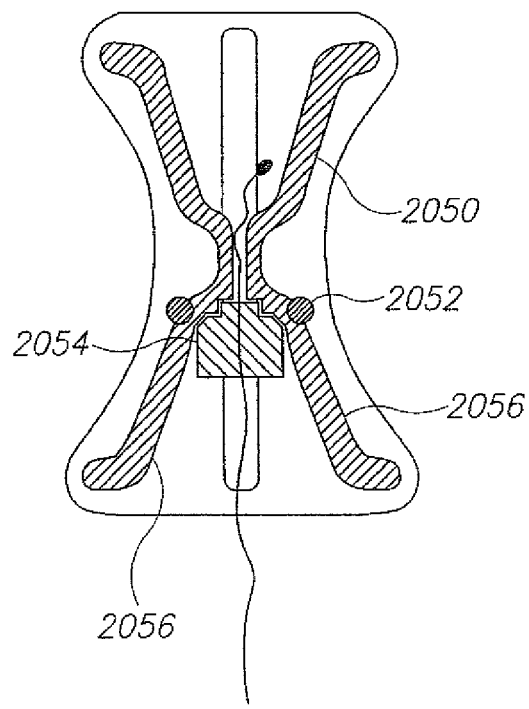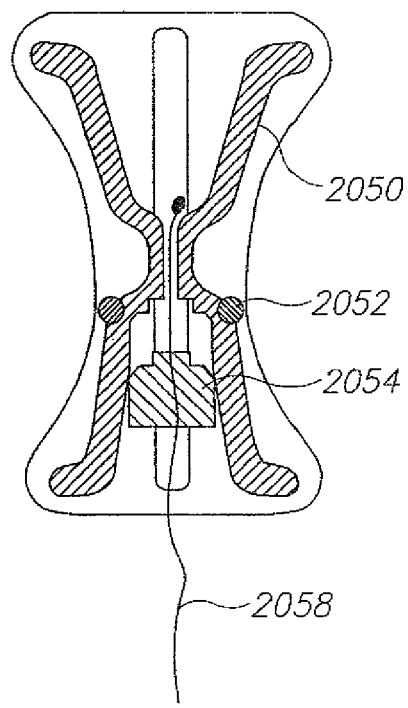
FIG.20D  FIG.20E
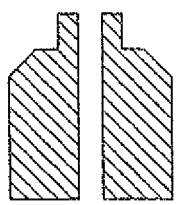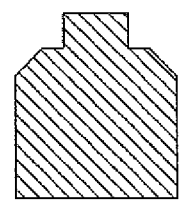
FIG.20F  FIG.20G
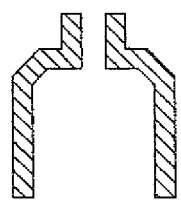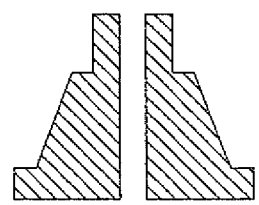
FIG.20H  FIG.20I

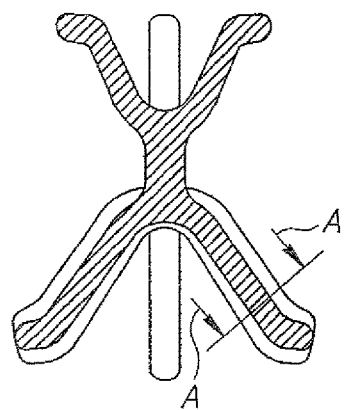
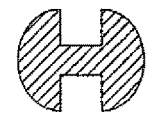
FIG.22A
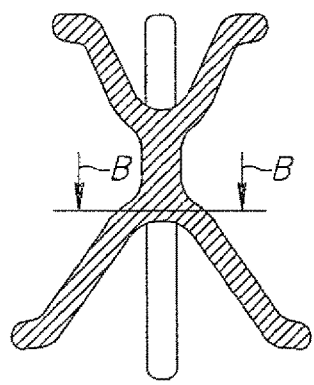
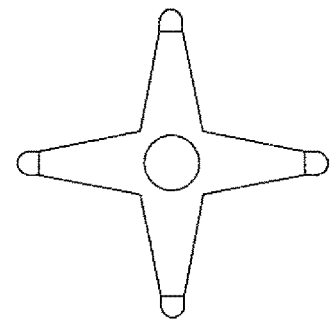
FIG.22B
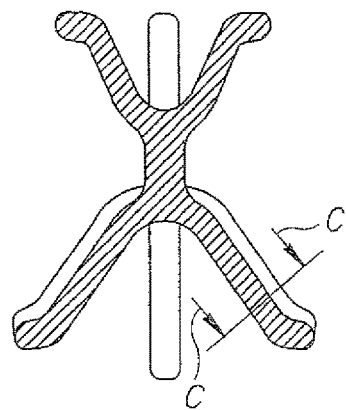
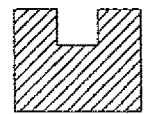
FIG.22C

APPARATUSES FOR THE AMELIORATION OF URINARY INCONTINENCE IN FEMALES

RELATED APPLICATIONS

This application is a continuation of U.S. patent application Ser. No. 11/886,248 filed on Sep. 13, 2007, now U.S. Pat. No. 8,617,047, which is a National Phase of PCT Patent Application No. PCT/IL2006/000346 having International Filing Date of Mar. 16, 2006, now published as WO 2006/097935 on Sep. 21, 2006, which is a continuation-in-part of PCT Application No. PCT/IL2005/000304 filed on Mar. 17, 2005, now published as WO 2005/087154 and entitled "Apparatus for the Prevention of Urinary Incontinence in Females" and a continuation-in-part of PCT Patent Application No. PCT/IL2004/000433 filed on May 20, 2004, now published as WO 2004/000433, the disclosures of which are herein incorporated by reference. Those related applications also claim the benefit of priority under 35 USC 119(e) of U.S. Provisional Patent Application No. 60/553,964 filed on Mar. 18, 2004; 60/555,977 filed on Mar. 25, 2004; 60/570,469 filed on May 13, 2004; 60/570,535 filed on May 13, 2004; 60/598,835 filed on Aug. 5, 2004; 60/602,636 filed on Aug. 19, 2004, the disclosures of which are herein incorporated by reference. In addition to the above, PCT Patent Application No. PCT/IL2006/000346 claims the benefit of priority under 35 USC 119(e) of U.S. Provisional Patent Application No. 60/719,422 filed on Sep. 22, 2005 and 60/762,059 filed on Jan. 25, 2006, the disclosures of which are herein incorporated by reference.

FIELD OF INVENTION

The present invention relates generally to treating feminine medical conditions, for example by providing devices for the prevention of female incontinence and/or prolapse.

BACKGROUND OF THE INVENTION

Urinary incontinence is a widespread problem among females. It is estimated that up to 50% of women occasionally leak urine involuntarily, and that approximately 25% of women will seek medical advice at some point in order to deal with the problem. Stress incontinence, the most common type of urinary incontinence, refers to the involuntary loss of urine resulting from abdominal pressure rise occurring during exercise, coughing, sneezing, laughing, etc. While many different factors may contribute to the development of stress incontinence, it is most prevalent among women ages 35-65 and those who have had multiple vaginal deliveries. Stress incontinence is both aggravating and unpleasant for women, and it can also be embarrassing. Many women wear sanitary pads or diapers in order to deal with incontinence, though this is not a real solution to the problem and it can be very inconvenient and unreliable. Surgical treatment may involve securing the paraurethral tissues to the periosteum of the pubic bone or the rectus facia in order to elevate the bladder neck above the pelvic floor and thereby distribute pressure equally to the bladder, the bladder neck, and the mid-urethra. Recently, a procedure known as "TVT" ("Tension Free Vaginal Tape") was developed, in which a mesh tape is implanted underneath the mid-urethra, creating a hammock on which the urethra may kink during a rise in intra-abdominal pressure. However, surgery is only suitable for severe cases, and the majority of women experiencing incontinence do not need, and certainly would rather avoid, surgical solutions.

One modality of non-surgical treatment involves the use of devices that are inserted into the vagina, either by a medical practitioner or by the woman herself. Most devices are designed to apply pressure against the bladder neck so as to inhibit or completely block the flow of urine through the urethra. A variety of such devices are known in the art. For example, refer to U.S. Publication No. 2002/0183711 to Moser, entitled, "Urinary Incontinence Device"; U.S. Pat. No. 6,739,340 to Jensen, et al., entitled, "Device for prevention of involuntary urination"; U.S. Pat. No. 6,679,831 to Zunker, et al., entitled, "Resilient incontinence insert and a method of making the same"; U.S. Pat. No. 6,460,542 to James, entitled, "Female incontinence control device"; U.S. Pat. No. 6,413,206 to Biswas, entitled, "Intra-vaginal device"; U.S. Pat. No. 5,785,640 to Kresch, entitled "Method for Treating Female Incontinence"; U.S. Pat. No. 5,771,899 to Martelly, et al., entitled, "Pessary"; U.S. Pat. No. 5,618,256 to Reimer, entitled, "Device for Arrangement in the Vagina for Prevention of Involuntary Urination with Females and an Applicator for use in Insertion of the Device"; U.S. Pat. No. 5,417,226 to Juma, entitled, "Female Anti-Incontinence Device"; U.S. Pat. No. 5,386,836 to Biswas, entitled, "Urinary Incontinence Device"; U.S. Pat. No. 5,007,894 to Enhorning, entitled, "Female Incontinence Device"; and U.S. Pat. No. 4,920,986 to Biswas, entitled, "Urinary Incontinence Device", the disclosures of which are herein incorporated by reference.

One problem with many of the above listed devices is that they completely block the urethra and thus they need to be removed or collapsed in order to allow the woman to urinate. To overcome this drawback, vaginal devices have been developed having specialized shapes that do not completely block the urethra but these devices tend to be large, uncomfortable, and intrusive. They also tend to cause irritation or soreness to the vagina.

Another common shortcoming is that most devices known in the art also tend to be difficult or painful to insert and/or remove. In order to correctly inhibit urine flow, the device needs to be properly positioned in the vaginal canal. As a result, a doctor may be required to properly position the device. In most cases, the device is adapted for remaining in the vagina for a prolonged period of time (due to the time and expense of requiring a trained medical professional to insert the device). However, when positioned in the vagina for an extended period of the time, the device may cause vaginal infections, necrosis, or bleeding.

SUMMARY OF THE INVENTION

An aspect of some exemplary embodiments of the invention relates to providing incontinence devices with inserts adapted to provide resilient reinforcement to at least a portion of the device. Optionally, the incontinence devices are provided with support arms. In some exemplary embodiments, an insert is used in conjunction with the support arms of the incontinence device to provide urethral support to a patient. In an exemplary embodiment of the invention, the insert urges the support arms to expand radially (radially outwards from a central axis of the device) for providing urethral support. Optionally, radial expansion is up to 20% of the previous radial profile of the device. Optionally, radial expansion is up to 50% of the previous radial profile of the device. In some embodiments, radial expansion is more than 50% of the previous radial profile of the device. In some exemplary embodiments of the invention, an insert is located at the convergence of the support arms at a central node of the incontinence device. In some exemplary embodiments of the invention, the insert penetrates the central node of the incontinence device. In some exemplary embodiments of the invention, the insert is positioned on a surface of the device, an interior surface, which is located opposite a vaginal wall.

In an exemplary embodiment of the invention, the insert is conical shaped. Optionally, the insert is geometrically locking. Optionally, the insert is of varying geometry. Optionally, the insert is bi-stable. Optionally, the insert is an o-ring. Optionally, the insert is comprised of a plurality of components removably fitted together. Optionally, at least a portion of the insert is elastic. In some exemplary embodiments of the invention, the insert locks into at least one position on the incontinence device. In some exemplary embodiments of the invention, the insert removably locks into position on the incontinence device. In some exemplary embodiments of the invention, the insert is positioned in relation to the incontinence device such that support and/or pressure are rendered to the anchor arms of the device.

In some exemplary embodiments of the invention, the incontinence device is deployed using an applicator, such as those described herein and in related applications. The incontinence device is optionally provided with a removal device for removing the device from the vagina after use. In some exemplary embodiments of the invention, the incontinence device is provided with a cover. Optionally, urethral support is mid-urethral support.

In some exemplary embodiments of the invention, an incontinence device is provided with an internal and/or external resilient support member. Optionally, the resilient support member biases arms of the incontinence device. Optionally, the resilient support member biases arms of the incontinence device radially outwards from a central axis of the incontinence device. Optionally, resilient support member biases arms of the incontinence device radially inwards towards a central axis of the incontinence device. Optionally, the resilient support member is used for at least the support arms of the incontinence device. Optionally, the resilient support member is used for at least the anchor arms of the incontinence device. Optionally, the insert is positioned in relation to an incontinence device such that support and/or pressure are rendered to the support arms of the device. In some exemplary embodiments of the invention, support rendered by insert to device is support against the forces exerted on the arms by a vaginal wall. In some exemplary embodiments of the invention, the pressure urges the arms radially outward from a central axis of the device, causing radial expansion of the device.

In some exemplary embodiments of the invention, an incontinence device is provided with tension reducing arms. Optionally, tension is reduced by providing the arms with a folding section. In some exemplary embodiments of the invention, the tension reducing arms are folded while in storage within an applicator, however upon deployment, the arms expand to render support and/or anchoring.

An aspect of some exemplary embodiments of the invention relates to providing an incontinence device with multiple stable configurations. In some exemplary embodiments of the invention, an incontinence device is provided with a component which is at least bi-stable. Optionally, the bi-stable component is provided with a first stable position, which does not cause the device to expand radially, and at least a second stable position, which causes the device to expand radially. Optionally, the bi-stable component transfers from the first stable position to the second stable position without substantially moving in relation to the incontinence device. Optionally, the bi-stable component transfers from the first stable position to the second stable position by moving in relation to the incontinence device. In some exemplary embodiments of the invention, the device is provided with a removal device which is capable of changing the second stable position to the first stable position. Optionally, the device is used with a cover. Optionally, the device is deployed in a vagina using an applicator.

An aspect of some exemplary embodiments of the invention relates to providing an incontinence device which is comprised of different components with different material properties in order to achieve a particular operational profile. For example, in some exemplary embodiments of the invention, an insert is provided to the incontinence device where the insert is partially elastic and/or partially rigid. Optionally, a partially rigid insert is used to apply selective expansion and/or retraction of support and/or anchoring sections of the incontinence device. Optionally, different components with different material properties are used to distribute forces exerted on and/or by the incontinence device. In some exemplary embodiments of the invention, the incontinence device is comprised of different materials with different material properties in order to provide effective incontinence treatment.

An aspect of some exemplary embodiments of the invention relates to providing at least a portion of an incontinence device with elasto-mechanical radial expansion. In some exemplary embodiments of the invention, force is supplied for elasto-mechanical radial expansion by an elastic central member. Optionally, the elastic central member is operationally connected to expanders (which in some embodiments are mechanical, hence the name "elasto-mechanical") which cause radial expansion of the device. Optionally, the device is provided with support arms, which constitute a portion of the device which is radially expanded. Optionally, the device is provided with anchor arms, which constitute a portion of the device which is radially expanded. In some exemplary embodiments of the invention, radial expansion of the incontinence device occurs upon ejection of the device from an applicator. In some exemplary embodiments of the invention, the device is provided with a removal device which stops the elastic central member from exerting force on the expanders thereby causing a radial contraction of the device and/or enabling easier removal of the device.

An aspect of some exemplary embodiments of the invention relates to providing an incontinence device with an elastomeric ring for assisting with radial expansion and/or contraction of the device. In some exemplary embodiments of the invention, the elastomeric ring is used in a plurality of positions in relation to the device in order to provide radial expansion and/or contraction to the device. Optionally, the elastomeric ring slides along an exterior of the device in order to assume the plurality of positions. In some exemplary embodiments of the invention, the shapes of the incontinence device and/or a pivot piece assist the elastomeric ring with expansion and/or contraction of the incontinence device. In some exemplary embodiments of the invention, the device is provided with a removal device which dislodges the pivot piece allowing for device contraction and/or easier removal of the device. In some exemplary embodiments of the invention, the elastomeric ring is a component of a bi-stable incontinence device. In some exemplary embodiments of the invention, the elastomeric ring is not flexible. Optionally, the elastomeric ring is not ring shaped; it is optionally square, rectangular, triangular, ovoid, or u-shaped, for example.

An aspect of some exemplary embodiments of the invention relates to providing at least one tensile element to an incontinence device for providing radial expanding force, but not compressive force, to the device. In some exemplary embodiments of the invention, at least one tensile element extends between an arm of an anchor section and a corresponding arm of a support section of the incontinence device. Optionally, the at least one tensile element is elastic. In some exemplary embodiments of the invention, the at least one tensile element is stretched prior to deployment and while being stored in an applicator. Optionally, the at least one tensile element substantially unstretches upon being deployed, setting providing expansion force to the incontinence device as a function of the natural unstretched length of the connector. In some exemplary embodiments of the invention, the at least one tensile element helps to resist movement of the support section and/or the anchor section after deployment of the device in the vagina. Optionally, the flexibility of the support section and/or anchor section are adjusted depending on the desired response to the at least one tensile element.

An aspect of some exemplary embodiments of the invention relates to an incontinence device which scrolls in order to increase and/or decrease its size profile. In some exemplary embodiments of the invention, the incontinence device is rolled up around its central axis to reduce the diameter of the device. Optionally, the reduced diameter device is stored in an applicator prior to deployment. In an exemplary embodiment of the invention, when the scrolled incontinence device is deployed out of the applicator, it at least partially unrolls to assume a larger diameter to provide support to the patient's urethra. Optionally, the scrolling device is provided with a plurality of protrusions for offering support and/or anchoring. In some exemplary embodiments of the invention, the device is adapted so that the arms and/or protrusions of the device position themselves on either side of the urethra; either directly upon deployment or after movement by the user causes slight rotation of the device. Optionally, the scrolling device is cylindrical. Optionally, the scrolling device has a larger diameter at one end than the other end.

In an exemplary embodiment of the invention, an incontinence device is provided with a plurality of connected scrolling sections. Optionally, two scrolling sections are provided to incontinence device. Optionally, scrolling sections are connected by a flexible member. In some exemplary embodiments of the invention, a scrolling section is located at each end of the flexible member. Optionally, scrolling sections are provided with a plurality of protrusions for offering support and/or anchoring. In some exemplary embodiments of the invention, scrolling sections roll around the central axis of the device to reduce their radial profile. Optionally, the reduced radial profile device is stored in an applicator. In some exemplary embodiments of the invention, upon deployment of the incontinence device, scrolling sections unroll to assume a larger diameter to provide support to a patient's urethra. Optionally, support is mid-urethral.

An aspect of some exemplary embodiments of the invention relates to providing lubrication at least to the external surface of an applicator. Optionally, the applicator is for inserting an incontinence device. Optionally, lubrication is provided by a reservoir ring positioned around the circumference of the applicator. Optionally, the reservoir ring is porous. Optionally, the reservoir ring is hollow. Optionally, lubrication is provided by a layer on the applicator which is revealed when a cover is removed. Optionally, lubrication is provided by a movable sleeve positioned on the applicator and wherein the lubricant is located. In an exemplary embodiment of the invention, the applicator is lubricated prior to insertion into the patient's vagina. Optionally, the ring is removed after lubrication but prior to insertion. Optionally, the sleeve is removed after lubrication but prior to insertion. Optionally, an indicator, such as a ring, is used on the applicator to indicate the proper depth for insertion of the applicator in order to achieve effective device deployment. Optionally, the ring physically stops the applicator at the proper depth for insertion of the applicator in order to achieve effective device deployment.

An aspect of some exemplary embodiments of the invention relates to providing applicators for extending the shelf life of incontinence devices. Optionally, any radially expandable device is used with the shelf life extending applicators. In an exemplary embodiment of the invention, an applicator is provided with a flared section for storage of at least the support section of an incontinence device. The flared section allows the support section to remain at least partially unstressed during storage. Optionally, a central node of the incontinence device is also located in flared section. Optionally, the flared section is sized to accommodate at least partially expanded arms of the incontinence device. Optionally the flared section is used to indicate the proper depth for insertion of the applicator in order to achieve effective device deployment.

In some exemplary embodiments of the invention, an applicator is provided with a plurality of slots adapted and constructed to accommodate arms of an incontinence device such that when incontinence device is located within the applicator the arms protrude outwardly and/or uncompressed. Optionally, a movable sleeve is used to position the outwardly protruding arms inside the applicator in preparation for deployment. Optionally, an indicator, such as a ring, is used on the applicator to indicate the proper depth for insertion of the applicator in order to achieve effective device deployment.

An aspect of some exemplary embodiments of the invention relates to minimizing the size of an incontinence device deployment package by reducing the size of a plunger used to deploy an incontinence device from an applicator. In an exemplary embodiment of the invention, a telescoping plunger is provided. Optionally, the plunger is folded. Optionally, the telescoping plunger is comprised of at least two sections. Optionally, the plunger in a closed condition is approximately half its size when in a deployed condition. In an exemplary embodiment of the invention, a ring is located on the plunger to provide friction between the plunger and an applicator during relative movement between them. Optionally, the ring resists inadvertent dislodgment of the plunger form the applicator.

In an exemplary embodiment of the invention, the applicator contacts a central portion, such as the node, of the incontinence device to deploy it from the applicator. Optionally, the applicator deploys the incontinence device by contacting at least one support arm. In an embodiment of the invention, at least part of the applicator, such as the plunger is used to help place the support arm into a deployed position.

There is thus provided in accordance with an exemplary embodiment of the invention, an apparatus for treating urinary incontinence, comprising: a support section adapted for providing urethral support; an anchoring section for resisting movement of the apparatus; an insert, a portion of which is adapted to be positioned proximal to the support section; and, wherein the insert selectively provides at least support to the support section of the apparatus. Optionally, the insert is adapted to provide pressure to the support section, causing radial expansion of the support section. Optionally, the support section is flexible. In an exemplary embodiment of the invention, the support section is comprised of at least one support arm. Optionally, the insert is an o-ring. Optionally, the insert is flared. Optionally, the urethral support is mid-urethral support. In an exemplary embodiment of the invention, the apparatus further comprises a cover. Optionally, the insert is conical. Optionally, the insert is comprised of a plurality of geometrically interlocking elements. Optionally, the insert is comprised of at least a supporting protrusion and a locking protrusion. Optionally, the insert is an invertible membrane. Optionally, the insert is a ringed insert. In an exemplary embodiment of the invention, the apparatus further comprises a resilient support member. Optionally, the resilient support member biases at least the support section towards a central axis of the apparatus. Optionally, the resilient support member biases at least the support section away from a central axis of the apparatus. Optionally, the support section and anchoring section are comprised of at least 2 arms, respectively. Optionally, the arms are provided with a folding section. Optionally, the cover substantially encapsulates the apparatus. Optionally, at least the support section and the anchoring section are flexible. Optionally, the apparatus is flexible. In an exemplary embodiment of the invention, the apparatus further comprises a removal device.

There is this provided in accordance with an exemplary embodiment of the invention, an apparatus for treating urinary incontinence, comprising: a support section adapted for providing urethral support; an anchoring section for resisting movement of the apparatus; and, an insert, adapted to provide at least support to the support section and at least a portion of the insert being elastic. Optionally, the insert is comprised of a plurality of components removably fitted together. Optionally, the insert urges the support section radially outwards from a central axis of the apparatus. Optionally, the insert is provided with an expanded end which provides radial expansion to the anchoring section. In an exemplary embodiment of the invention, the apparatus further comprises a cover. Optionally, the cover substantially encapsulates the apparatus. Optionally, at least the support section and the anchoring section are flexible. Optionally, the apparatus is flexible. In an exemplary embodiment of the invention, the apparatus further comprises a removal device. Optionally, the urethral support is mid-urethral support. Optionally, the support section is comprised of at least one support arm.

There is thus provided in accordance with an exemplary embodiment of the invention, an apparatus for treating urinary incontinence, comprising: a support section adapted for providing urethral support; an anchoring section for resisting movement of the apparatus; at least one expander node, provided with at least one expander connected to the apparatus; an elastic member which passes through the at least one expander node; a removable safety catch provided to an expanded end of the elastic member which prevents expanded end from passing through the at least one expander node, and, wherein when the elastic member is substantially unstretched, the at least one expander causes radial expansion of the apparatus. In an exemplary embodiment of the invention, the apparatus further comprises a cover. Optionally, the cover substantially encapsulates the node, support section and the anchoring section. Optionally, at least the support section and the anchoring section are flexible. In an exemplary embodiment of the invention, the apparatus further comprises a removal device provided to the safety catch. Optionally, the urethral support is mid-urethral support. Optionally, the support section is comprised of at least one support arm.

There is thus provided in accordance with an exemplary embodiment of the invention, an apparatus for treating urinary incontinence, comprising: a support section adapted for providing urethral support; an anchoring section for resisting movement of the apparatus; a first groove; an elastomeric ring positioned on an exterior surface of the apparatus within the first groove; and, wherein the elastomeric ring provides compression force to at least a portion of the apparatus. Optionally, the elastomeric ring applies compression force to the support section to effectuate radial contraction of the support section. In an exemplary embodiment of the invention, the apparatus further comprises a second groove located between the first groove and the support section. In an exemplary embodiment of the invention, the apparatus further comprises a pivot piece located in a third groove. Optionally, upon deployment the elastomeric ring transitions from the first groove to the second groove causing radial expansion of the support and anchor sections. In an exemplary embodiment of the invention, the apparatus further comprises a removal device attached at least to the pivot piece. In an exemplary embodiment of the invention, the apparatus further comprises a cover. Optionally, the support and anchoring sections are flexible.

There is thus provided in accordance with an exemplary embodiment of the invention, an apparatus for treating urinary incontinence, comprising: a support section adapted for providing urethral support; an anchoring section for resisting movement of the apparatus; and, a tensile element, the tensile element attached to the support section and the anchoring section and adapted to provide radial expansion to the apparatus. Optionally, the tensile element is elastic.

There is thus provided in accordance with an exemplary embodiment of the invention, an apparatus for treating urinary incontinence, comprising: a support section adapted for providing urethral support; and, wherein the apparatus is provided with a first stable position and second stable position, such that when apparatus is in the second stable position the support section renders support to the urethra. Optionally, the support section is provided with a plurality of support arms. In an exemplary embodiment of the invention, the apparatus further comprises a bi-stable component wherein the bi-stable component is attached to the support section. Optionally, the bi-stable component is a flexible membrane. Optionally, the bi-stable component is a locking element. Optionally, the bi-stable component is ring. In an exemplary embodiment of the invention, the apparatus further comprises a first groove associated with the first stable position and a second groove associated with the second stable position. Optionally, the ring is slidable on an exterior of the apparatus from the first groove to the second groove. In an exemplary embodiment of the invention, the apparatus further comprises a removal device. Optionally, a removal device is attached to the bi-stable component for changing the second stable position to the first stable position.

There is thus provided in accordance with an exemplary embodiment of the invention, an apparatus for treating urinary incontinence, comprising: a support section adapted to render support to a urethra; an insert, the insert comprising a first material which exhibits first material properties and at least a second material which exhibits second material properties; and, wherein the insert selectively expands the support section. Optionally, the first material is flexible. Optionally, the second material is more rigid than the support section.

There is thus provided in accordance with an exemplary embodiment of the invention, an apparatus for treating urinary incontinence, comprising: a central node, wherein the central node is a rolled sheet; a plurality of support protrusions located on the node; and, a plurality of anchor protrusions located on the node. Optionally, the central node when rolled has a larger diameter on one end than the other end.

There is thus provided in accordance with an exemplary embodiment of the invention, an apparatus for treating urinary incontinence, comprising: a connector; and, a plurality of scrolling sections. Optionally, the connector is flexible. Optionally, the scrolling sections are provided with a plurality of protrusions for rendering urethral support. Optionally, the scrolling sections are provided with a plurality of protrusions for rendering anchoring. Optionally, the plurality of scrolling sections means two sections. Optionally, each of the two sections is located on an opposite end of the connector.

There is thus provided in accordance with an exemplary embodiment of the invention, an apparatus for inserting a vaginal device, comprising: an enclosure for containing the vaginal device; and a lubricating element located externally of the enclosure. Optionally, the lubricating element is a ring located around a circumference of the enclosure. Optionally, the lubricating element is a layer of lubricant applied to the enclosure which is revealed when a cover to the layer is removed. Optionally, the lubricating element is a movable sleeve located around a circumference of the enclosure. Optionally, the lubricating element is a layer of lubrication on the enclosure. Optionally, the lubrication is highly viscous such that once lubrication is located on the enclosure it substantially remains in place until use.

There is thus provided in accordance with an exemplar embodiment of the invention, an apparatus for extending the shelf life of a vaginally insertable device, comprising: an enclosure adapted for receipt of at least a first portion of the device and vaginal insertion; a section adapted for receipt of at least a second portion of the device such that the second portion is at least partially expanded. Optionally, the section is a flared enclosure. Optionally, the section is provided with a plurality of slots. Optionally, the slots are sized and numbered to accommodate the second portion of the device. In an exemplary embodiment of the invention, the apparatus further comprises a slidable sleeve located externally of the enclosure for repositioning the second portion of the device prior to insertion of the device into a vagina.

There is thus provided in accordance with an exemplary embodiment of the invention, an apparatus for motivating a vaginally insertable device, comprising: an outer section, adapted for insertion into a vaginal applicator; and, an inner section, capable of insertion into and movement within the outer section. In an exemplary embodiment of the invention, the apparatus further comprises a ring, wherein the ring is located on the outer section such that friction is created by ring when there is movement of the apparatus relative to the applicator.

There is this provided in accordance with an exemplary embodiment of the invention, a collapsible apparatus for inserting a vaginal device, comprising: an enclosure for containing the vaginal device; and a plunger adapted to coaxially fit within the enclosure. Optionally, the plunger is substantially located within the enclosure during storage. Optionally, an insert is provided to the vaginal device. Optionally, the insert is attached to a removal/activator device. Optionally, the removal activator device is removably latched to the plunger. Optionally, movement of the plunger out of the enclosure moves the insert at least partially through the vaginal device.

BRIEF DESCRIPTION OF THE FIGURES

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which:

FIG. 3A is a profile view of an incontinence device with a varying geometry insert as in an applicator in accordance with an exemplary embodiment of the invention;

FIG. 3B is a profile view of an incontinence device with a varying geometry insert as deployed in accordance with an exemplary embodiment of the invention;

FIG. 3C is a profile view of an incontinence device with a varying geometry insert during removal in accordance with an exemplary embodiment of the invention;

FIG. 7A is a profile view of a scrolling incontinence device in accordance with an exemplary embodiment of the invention;

FIG. 7B is a profile view of a scrolling incontinence device with a flared proximal end in accordance with an exemplary embodiment of the invention;

FIG. 7C is a top and/or bottom view of a scrolling incontinence device in accordance with an exemplary embodiment of the invention;

FIG. 7D is a top view of a scrolling incontinence device in an applicator in accordance with an exemplary embodiment of the invention;

FIG. 15A is a cross-sectional view of an incontinence device with an o-ring insert, in accordance with an exemplary embodiment of the invention;

FIG. 15B is a cross-sectional view of an incontinence device with an o-ring insert being removed, in accordance with an exemplary embodiment of the invention;

FIGS. 15C and 15D are top views of exemplary configurations of an o-ring insert, in accordance with an exemplary embodiment of the invention;

FIG. 20D is a cross-sectional view of an alternative incontinence device provided with an elastomeric ring in a deployed configuration, in accordance with an exemplary embodiment of the invention;

FIG. 20E is a cross-sectional view of an alternative incontinence device provided with an elastomeric ring in a removal configuration, in accordance with an exemplary embodiment of the invention;

FIGS. 20F-I are cross-sectional views of alternative inserts which can be used with incontinence devices described herein, in accordance with an exemplary embodiment of the invention;

FIG. 22A is a cross-sectional view of an exemplary arm configuration, in accordance with an exemplary embodiment of the invention;

FIG. 22B is an exemplary cross-sectional view of an incontinence device, in accordance with an exemplary embodiment of the invention;

FIG. 22C is a cross-sectional view of an exemplary arm configuration, in accordance with an exemplary embodiment of the invention;

DETAILED DESCRIPTION OF EXEMPLARY EMBODIMENTS

Introduction

Figure 1A:
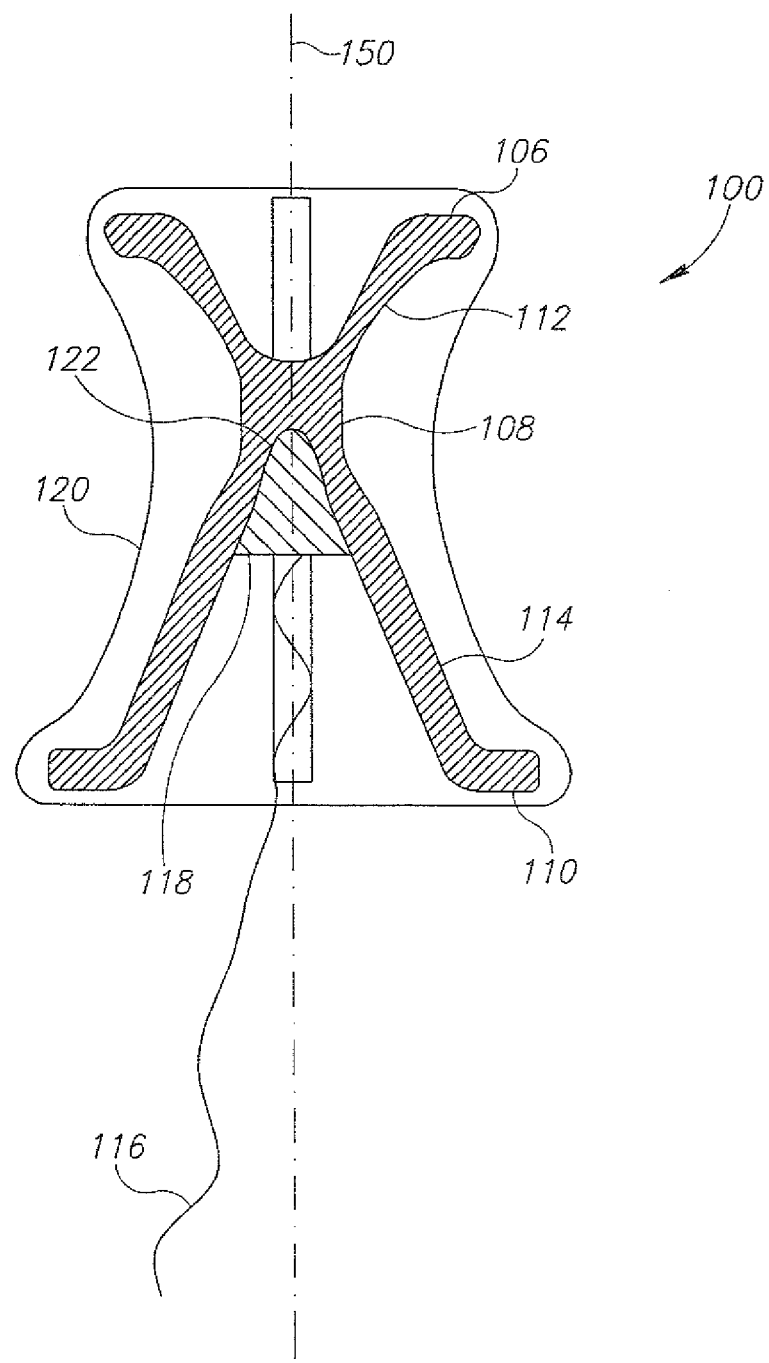
FIG. 1A is a profile view of an incontinence device with a conical insert in accordance with an exemplary embodiment of the invention.

Referring to FIG. 1A, a profile view of an exemplary embodiment of the incontinence device 100 is shown. In an exemplary embodiment of the invention, the device 100 is arranged around a central axis 150 and divided into three parts. Optionally, the device has more or less parts. A top section 106 is provided which serves as the "anchoring" element, for stabilizing the device within the vagina. There are two types of anchoring, axial anchoring which acts in the direction along the central axis of the vagina, and radial anchoring which acts side-to-side or substantially perpendicular to the central axis of the vagina. A bottom section 110 is provided which serves as the "supporting" element, for generating urethral support. In some embodiments of the invention, support is generated at a mid-urethral location. In some embodiments of the invention, the bottom supporting section 110 provides at least one form of anchoring to help anchor device 100 in position. In some embodiments of the invention, the entire length of device 100 is between 30 mm and 50 mm. optionally, device 100 is larger or smaller depending on the individual needs of the patient. In some exemplary embodiments of the invention, the various sections, parts and/or elements described are optional. In some exemplary embodiments of the invention, the functions the various sections, parts and/or elements perform are optional.

In some exemplary embodiments, a central section 108, or node, is provided which optionally connects anchoring 106 and supporting 110 elements. The node 108 of this and many other devices described herein has a length which is only a small portion of the overall length of the device, in some embodiments of the invention. In some embodiments of the invention, the length of the node is less than 15% of the entire length of the device. In some embodiments of the invention, the length of the node is less than 20% of the entire length of the device. In other embodiments of the invention, the length of the node is less than 30% the entire length of the device. In an exemplary embodiment of the invention, the length of the overall device is up to 75 mm. Optionally, the length of the overall device is up to 60 mm. Optionally, the length of the overall device is 50 mm. In some exemplary embodiments of the invention, the overall device is not less than 30 mm in length. In some embodiments of the invention, a node which is short relative to the entire length of the device allows for more flexibility in varying the stiffness, the comfort, and the size of device 100. Optionally, the node is not provided with one axis longer than the other, the axes are equal in length (e.g. a sphere or a cube). In an exemplary embodiment of the invention, a small node in relation to the overall length of the device allows for greater control over the behavior of the anchoring and support arms, described below. This is because the overall length of the device is somewhat determined by the topography of the vagina. If, for example, the central node was a significant portion of the overall length of the device, then the arms would be short in length and at an angle to the central node close to 90°. This configuration does not have the advantage of being able to take advantage of the flexibility that is possible with longer arms at a lower angle of incidence to the central node.

In some exemplary embodiments of the invention, a cover 120, described in more detail below, is provided to device 100. The elements of the device 100 optionally function as an internal support structure for a cover 120. Optionally, the tension of cover 120 is increased by the arms of device 100.

In an exemplary embodiment, the anchoring element 106 and the supporting element 110 have four (4) arms each or arm sets 112 and 114, respectively. In an exemplary embodiment of the invention, four arms are provided to each section in which two are generally projected towards the bladder, and two are generally projected towards the vaginal floor adjacent the bowels. The two support arms which project towards the bladder fit within natural slots on either side of the urethra in some embodiments of the invention. Optionally, the anchoring and supporting elements are provided with more or less arms. For example, the anchoring element could have more arms if there is concern about unwanted movement of device 100. In other embodiments of the invention, the arms are provided at varied angles with respect to the node 108 and/or each other. Optionally the arms 112 and 114 are flexible or rigid and are constructed of a biocompatible material. Optionally, each of the arms reacts individually to the forces exerted on them by the vaginal wall, like independent suspension in an automobile. Optionally, each of the support arms functions separately to render support to the urethra. Optionally, padding elements adapted for contact are provided to the arms where they are likely to contact the vaginal wall of the user in order to increase the contact surface area and thus, increase comfort to the wearer. Padding elements also reduce the likelihood of necrosis due to the reduced pressure exhibited between the device and the vaginal wall, as a result of the increase in contact surface area between the two. In an exemplary embodiment of the invention, the anchoring element does not apply significant pressure to the wearer's vagina and/or urethra, thereby enhancing comfort.

In some embodiments of the invention, other structure is provided instead of arms which is capable of supporting the urethra, in the case of the support section, or preventing the device from unintentionally moving, in the case of the anchor section. For example, at least one cone, protrusion, and/or extension attached to the node could be used for anchoring and support.

The anchoring arms of the device prevent the device from moving unintentionally out of position. In an exemplary embodiment of the invention, the anchor element arms 112 resist motion of the device towards the uterus because the arms increase their angle to the node 108. This effective increase in radius operates to counteract the motion of the device further into the vagina. In some embodiments of the invention, anchor element arms 112 are provided with a large angle to the node to enhance this anchoring effect. It should be noted that this enhanced anchoring effect is observed only up until a maximum angle. A narrowed node 108 increases the flexibility and the possible ranges of movement for the overall device 100 in some embodiments of the invention. Optionally, devices such as wires and/or springs are embedded in the neck in order to enhance flexibility for device 100. This additional flexibility can enhance the comfort of the woman while wearing the device 100. Optionally, the additional flexibility of device 100 enables more comfortable defecation in comparison to prior art devices. Any of the embodiments described herein are optionally utilized in conjunction with a narrowed node 108.

While the arms are flexible, it should be noted that they are rigid enough to prevent unwanted motion of the device towards the entrance of the vagina. Optionally, the arms are rigid but the node is flexible, the node thus providing flexible anchoring and support. Movement towards the vaginal opening is resisted by the arms which position themselves in the vagina towards the cervix and which, in some exemplary embodiments of the invention are held in place by pressure exerted on them by the vaginal wall, see for example the description of "tenting" below. These features work independently from and in conjunction with the tenting behavior of the vaginal walls described below, which also helps to maintain the device in place.

An additional feature of the anchoring arms of the device 100 is that they operate remotely from the support arms. This reduces the amount of pressure applied to the urethra by the device because in some exemplary embodiments of the invention, the support arms do not need to render anchoring functions in addition to support. Optionally, the urethral support is mid-urethral support. Such a configuration increases comfort to the wearer, prevents unnecessary damage to the tissues adjacent to the device, increases the anchoring function of the device, and in some optional embodiments of the invention allows the wearer to void voluntarily without having to remove the device to urinate.

The arms 112 of the anchoring element 106 force the device 100 to remain in situ within the vagina, unable to substantially move inwards or outwards, or to rotate. One reason this occurs is as a result of the special tendency of vaginal walls to collapse and form an occluded lumen. The arms of the device cause "tenting" of the walls on top of them with resultant sagging of the walls around the node 108, thereby stabilizing the device 100. The arms 114 of the supporting element 110 cause relative elevation of the tissues around mid-urethra, acting as a hammock. This hammock supports mid-urethra in a tension free manner, much like the TVT operation. In a woman who leaks urine during a stressful event (when abdominal pressure rises during coughing, sneezing, etc.), the urethra sags down but meets the hammock in its mid part. The meeting of the urethra and the hammock causes an elevation of the intraurethral pressure with resultant urinary continence. In some embodiments of the invention the radiating support arms 114 of device 100 create an overall device radial diameter of 25 mm to 50 mm within the vaginal cavity. Optionally, the diameter is larger or smaller depending on the individual needs of the patient.

It should also be noted that for certain women, the described devices herein can also be used as a treatment for prolapse. For example, arms which are expanded to a certain radius for incontinence treatment can optionally expand to a larger radius for prolapse treatment. For example, prolapse treating configurations optionally exhibit a diameter of up to 100 mm.

Various incontinence device embodiments are described herein, many of which utilize inserts to assist with radial expansion of the incontinence device. It should be noted that many of these inserts optionally have multiple stop positions which correspond to multiple incontinence device configurations. Specific positions are optionally selected depending on the needs of the patient. In addition, although certain nomenclature is used (e.g. "anchoring" and "support") it should be understood that these are for ease of reference only, and in some embodiments of the invention an "anchoring" section could be used for providing urethral support and/or vice versa.

Exemplary Devices with an Insert for Treating Incontinence

In some exemplary embodiments of the invention, arms are manufactured so that they are biased towards a central axis of device 100. In such an embodiment, it is expected that storage (e.g. storage in an applicator, such as described below) in a contracted configuration imposes less stress on device 100 than if it was manufactured with arms biased in an expanded configuration. The arms are optionally placed in an expanded configuration during or after deployment, such as by using the inserts described herein. In an exemplary embodiment of the invention, it is conceived that removal of the insert causes the arms to return to the contracted state for easy removal from the user's vagina.

Many of the exemplary incontinence devices described herein are optionally manufactured with anchoring and/or support elements (e.g. arms) being biased in a contracted, non-deployed configuration.

FIGS. 1A-B, 2A-D, 3A-C, 15A-D, 16A-D, 17A-D, 18A-B, 23A-B, 27A-B and 28A-C show different exemplary embodiments of inserts which are optionally used with an incontinence device. Inserts are generally used to provide the support arms with additional support against pressure exerted on the support arms by the vaginal wall and/or with radial expansion. In addition, removable inserts such as those described herein, enable the incontinence devices to render effective incontinence treatment while avoiding some of the storage stresses that would normally come with devices which render such effective treatment. In an exemplary embodiment of the invention, storage stresses are avoided because the insert is stored in a non-deployed position, the non-deployed position not exerting treatment level pressure on the support arms. It should be understood, that the inserts and device configurations described in reference to FIGS. 1A-B, 2A-D, 3A-C, 15A-D, 16A-D, 17A-D, 18A-B, 23A-B, 27A-B and 28A-C are exemplary only, and that different configurations are optionally used depending on the needs of the patient. For example, the insert is optionally shaped to urge the support arms to different radial expansion diameters, as measured from a central axis of the device. Optionally, the insert is provided with a plurality of removably locking positions on the device, with each locking position corresponding to a slightly different configuration, such as radial expansion diameter, of the device.

In the exemplary embodiment of the invention depicted in FIG. 1A, incontinence device 100 is provided with a conical insert 118. Conical insert 118 is designed such that upon insertion into a conical recess 122, located just proximal of node 108, conical insert 118 applies outward radial pressure to support arms 114, thereby causing them to diverge and support the urethra. Optionally, conical insert 118 is inserted into conical recess 122 upon deployment from an applicator, via pressure from a plunger. Optionally, conical insert 118 is prepositioned in conical recess 122 prior to deployment. Optionally, varying sizes of conical insert 118 are used depending on the spread desired from support arms 114.

In an exemplary embodiment of the invention, conical insert 118 once deployed into conical recess 122 is removably fixed there by friction and/or pressure. Friction is created between the outer surface of conical insert 118 and the surface facing conical insert 118 of conical recess 122. This friction resists movement of conical insert 118 from conical recess 122, especially with the addition of pressure exerted on conical insert 118 by support arms 114. In an exemplary embodiment of the invention, pressure on conical insert 118 by support arms 114 is ultimately derived from pressure on device 100 from the vaginal wall.

In some exemplary embodiments of the invention, conical insert 118 is constructed from any material capable of urging support arms 114 outward. Optionally, device 100 is positioned beneath the mid-urethra to render support. Optionally, any of the devices described herein render mid-urethral support. Conical insert 118 is optionally constructed of the same material as device 100. Optionally, conical insert 118 is constructed of a harder and/or stiffer and/or denser material than device 100 to provide enhanced resistance to the counter-pressure of the vaginal wall. In some exemplary embodiments of the invention, a removal device 116, such as a string, is attached to conical insert 118.

Figure 1B:
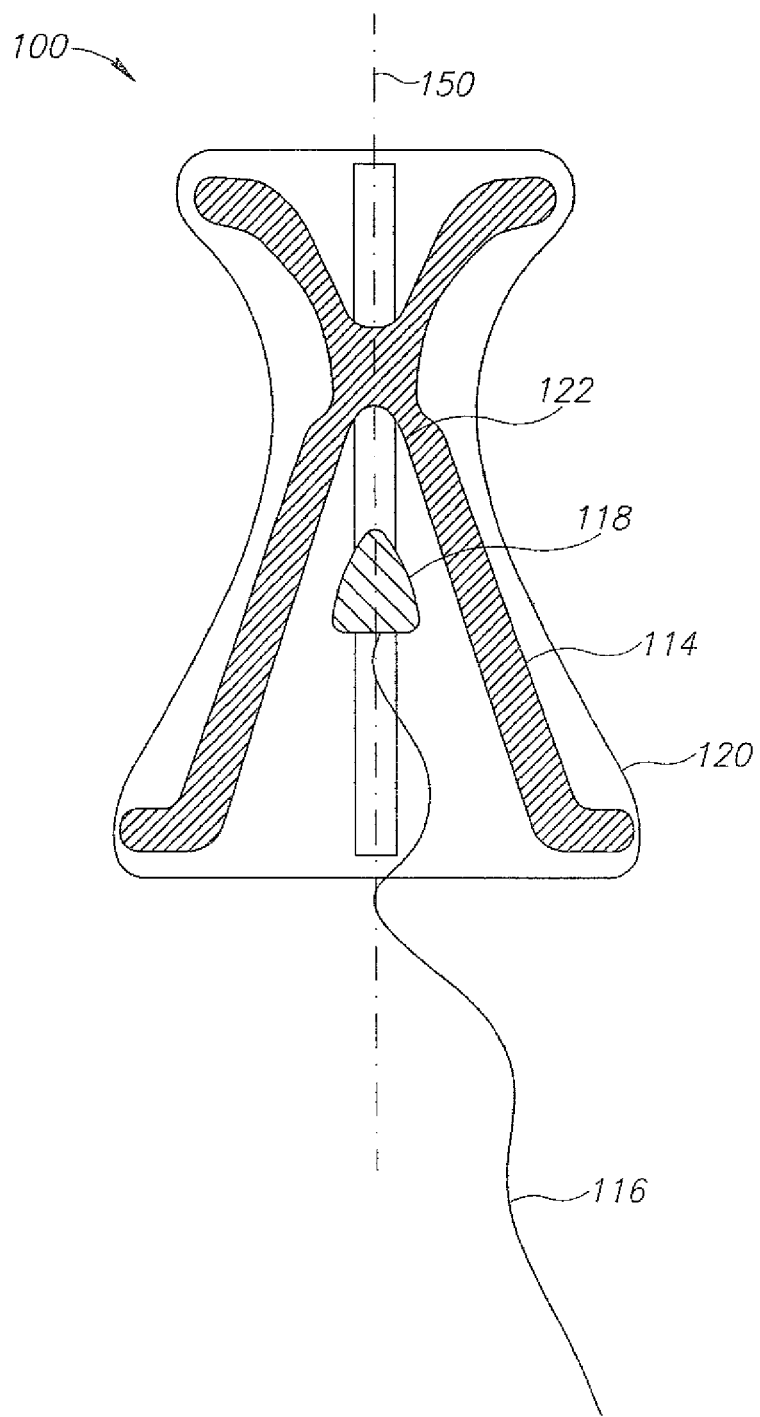
FIG. 1B is a profile view of an incontinence device with a conical insert during device removal in accordance with an exemplary embodiment of the invention.

Referring to FIG. 1B, a profile view of incontinence device 100 with conical insert 118 is shown during device 100 removal, in accordance with an exemplary embodiment of the invention. In some embodiments, application of a downward force, a force away from the cervix, dislodges conical insert 118 from conical recess 122. Once the support rendered to support arms 114 is removed by removing conical insert 118, they are more easily able to converge towards central axis 150 facilitating easier and/or more comfortable removal of device 100 than if the arms 114 were fully deployed with conical insert 118 reinforcement. Optionally, conical insert 118 remains within cover 120 upon detachment from conical recess 122. Optionally, additionally or alternatively, a removal device is attached to cover 120 wherein upon a downward force exercised on the removal device causes cover 120 to collapse on support arms 114, forcing them towards central axis 150 and therefore reducing the radial profile of device 100 for easier removal.

Figure 2D:
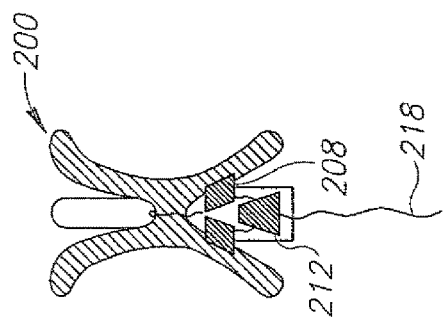
FIG. 2D is a profile view of an incontinence device with a geometric locking insert showing device removal in accordance with an exemplary embodiment of the invention.
Figure 2C:
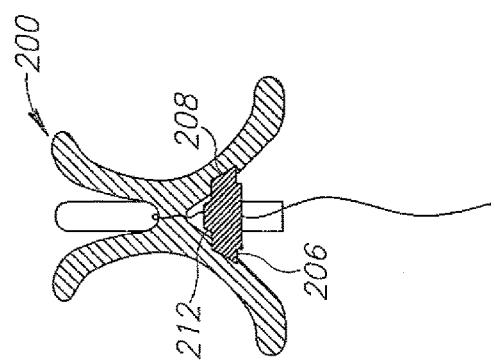
FIG. 2C is a profile view of an incontinence device with a geometric locking insert in a deployed position in accordance with an exemplary embodiment of the invention.
Figure 2B:
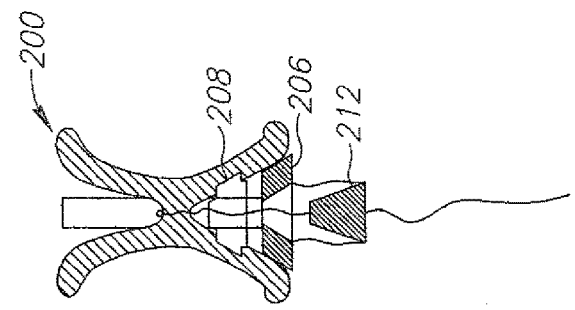
FIG. 2B is a profile view of an incontinence device with a geometric locking insert being deployed in accordance with an exemplary embodiment of the invention.
Figure 2A:
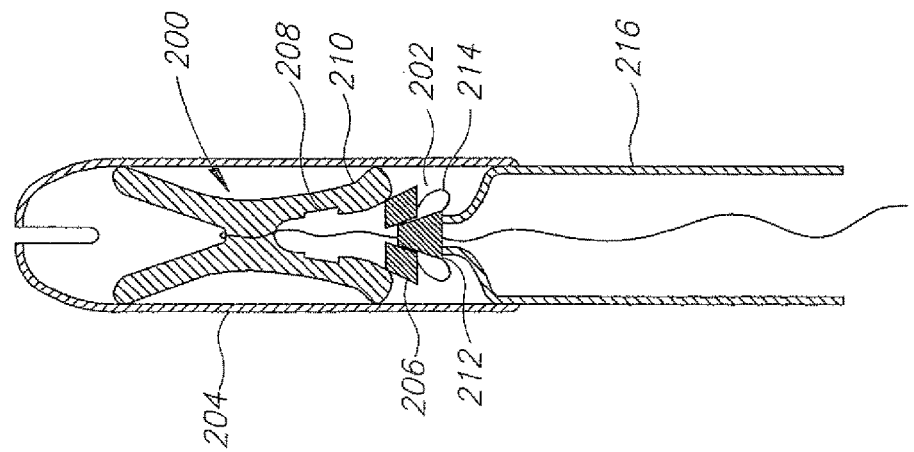
FIG. 2A is a profile view of an incontinence device with a geometric locking insert in an applicator in accordance with an exemplary embodiment of the invention.

FIG. 2A shows a profile view of an incontinence device 200 with a geometric locking insert 202 in accordance with an exemplary embodiment of the invention. Device 200 is slightly different than device 100 in that it is optionally comprised of more than one piece. The addition of at least one additional piece allows for part of the insert to lock with device 200, and for part of the insert to be removable to assist with device 200 removal. In addition, in some exemplary embodiments of the invention, an external ring 206 of device 200 is capable of mechanically locking into the support arms. Device 200 is shown in an applicator 204 which can optionally be used to deploy device 200 in the vagina. In some exemplary embodiments of the invention, device 200 is comprised of a plurality of components. Optionally, external ring 206 is provided which is adapted to be locked into a slot 208 located on the inner surfaces of support arms 210. Optionally, a plurality of slots are located on the inner surfaces of support arms 210, external ring 206 being pushed from slot to slot until the desired radial expansion of support arms 210 is achieved. Optionally, there is provided an internal insert 212 adapted to geometrically mate with the inner surface of external ring 206 such that internal insert 212 can be inserted through external ring 206. Optionally, more than external ring 206 and internal insert 212 comprise geometric locking insert 202. Optionally, a connecting device 214 is provided which maintains internal insert 212 in close proximity to external ring 206 in a suitable orientation for insertion of internal insert 212 through external ring 206.

In an exemplary embodiment of the invention, device 200 is stored in applicator 204 in a partially assembled state, such as shown in FIG. 2A. In some exemplary embodiments of the invention, maintaining device 200 in a partially assembled state, particularly where external ring 206 is not locked into slot 208, the device adapted to better withstand storage stresses while not in use, allowing for longer storage and/or greater efficacy of device 200. Deployment of device 200 is illustrated in FIG. 2B where internal insert 212 is urged through external ring 206 by a plunger 216 (depicted in FIG. 2A), in an exemplary embodiment of the invention. Upon the engagement of external ring 206 by internal insert 212, external ring 206 is urged towards slot 208 by continued pressure towards the cervix on plunger 216. Device 200 eventually locks itself in slot 208, which in turn urges support arms 210 radially outwards into a deployed position thereby exerting a predefined supportive tension, in an exemplary embodiment of the invention.

FIG. 2C illustrates device 200 in a deployed mode according to an exemplary embodiment of the invention. It can be seen that external ring 206 is locked into slot 208, which is shaped to mate with a predetermined external ring profile. Optionally, multiple slots are provided which are capable of receiving external ring 206, with each slot defining a different configuration for device 200. Optionally, external ring 206 is shaped to avoid misapplication, for example with grooves to accommodate support arms 210. Internal insert 212 is removably positioned within external ring 206. Optionally, internal insert 212 is held in place by frictional forces between external ring 206 and internal insert 212. Optionally, internal insert 212 is held in place by compression forces from support arms 210.

FIG. 2D is a profile view of device 200 showing removal of device 200, in accordance with an exemplary embodiment of the invention. Removal of device 200 is optionally achieved by pulling on removal device 218 away from the cervix. Optionally, removal device 218 is attached to internal insert 212. Additionally or optionally, removal device 218 is attached to device 200. Sufficient force on removal device 218 in a direction away from the cervix dislodges internal insert 212 from external ring 206, in accordance with an exemplary embodiment of the invention. In an exemplary embodiment of the invention, sufficient force is such that it is enough to remove internal insert 212 from its friction fit to external ring 206, accounting for at the very least the pressure rendered to internal insert 212 from the vaginal wall via device 200 and external ring 206. Once the at least partially flexible external ring 206 is no longer reinforced by internal insert 212, support arms 210 are allowed to converge towards the central axis of device 200 enabling easier and/or more comfortable removal of device 200. Optionally, a cover is used in conjunction with device 200. In an exemplary embodiment of the invention, the cover may also contribute to converging support arms 210 towards the central axis during removal. Optionally, a removal device is attached to the cover.

Referring to FIG. 3A, an incontinence device 300 with a varying geometry insert 302 is shown, in accordance with an exemplary embodiment of the invention. In some exemplary embodiments of the invention, device 300 is different from device 100 and device 200 in that varying geometry insert 302 traverses the length of the central node of device 300, as opposed to staying essentially within the confines of the support section. Varying geometry is provided to insert 302 in order to perform at least three basic functions with respect to device 300. First, the distal protrusion is used to prevent insert 302 from being pulled out of device 300 from the proximal side of device 300, in an exemplary embodiment of the invention. Second, a locking protrusion 316 is used to secure insert 302 to device 300 when in a deployed condition, in accordance with an exemplary embodiment of the invention. Third, a support protrusion is used to provide support to the support arms of device 300 in accordance with an exemplary embodiment of the invention.

In an exemplary embodiment of the invention, device 300 is depicted in an applicator 304 adapted for deployment of the device 300 into a vagina to render urethral support. Optionally, urethral support includes mid-urethral support. Optionally, device 300 is used in conjunction with a cover 306. In an exemplary embodiment of the invention, a plunger 308 is provided to proximal end of applicator 304 to facilitate deployment of device 300, where proximal end is towards the vaginal opening and distal is towards the cervix. Optionally, only two distinct protrusions are present. In an exemplary embodiment of the invention, at the distal end of insert 302 is a distal protrusion 310 located in a recess located at the convergence of the anchoring arms 312. Optionally, distal protrusion 310 is adapted and constructed to resist, optionally prevent, passage of the entire insert 302 away from the cervix through a canal 314 which passes through device 300 and which accommodates insert 302. A locking protrusion 316 is optionally located between the distal and proximal ends of insert 302 and is shaped, in accordance with some exemplary embodiments of the invention, to mate with a locking recess 318 located in canal 314. A support protrusion 320 is located at the proximal end of insert 302 in an exemplary embodiment of the invention. In some exemplary embodiments of the invention, device 300 is a device with multiple stable configurations, such as described below.

FIG. 3B illustrates incontinence device 300 in an exemplary deployed configuration, wherein insert 302 is advanced through canal 314 such that locking protrusion 316 is removably locked in locking recess 318. In some exemplary embodiments of the invention, locking protrusion 316 and/or locking recess 318 are positioned sufficiently away from support protrusion 320 such that when in a removably locked condition, support protrusion 320 is in a position to render reinforcement to support arms 322. In an exemplary embodiment of the invention, support protrusion 320 urges support arms 322 radially outwards into a predefined position, optionally depending on the shape of support protrusion 320. Optionally, support arms 322 support the mid-urethra.

Removal of device 300 is optionally accomplished by unlocking insert 302 from locking recess 318 and dislodging supporting protrusion from its deployed position at the convergence of support arms 322. Optionally, removal of incontinence device 300 is effectuated by pulling on a removal device 324, depicted in FIG. 3C away 326 from the cervix. In an exemplary embodiment of the invention, sufficient applied force to removal device 324 causes locking protrusion 316 to become dislodged from locking recess 318, unlocking locking protrusion 316 and permitting movement of insert 302 towards the vaginal opening. In an exemplary embodiment of the invention, distal protrusion 310 halts downward motion of insert 302 when it reaches the recess marking the convergence of anchoring arms 312 because it is sized larger than canal 314. Continued downward force on removal device 324 causes device 300 to be removed from vagina as removal device 324 is attached to insert 302 which is not removable from device 300. Optionally or additionally, a removal device 324 is attached to cover 306. Optionally, removal is assisted by cover 306 which urges support arms 322 towards the central axis of device 300, allowing for easier and/or more comfortable removal.

Referring to FIG. 15A, a deployed incontinence device 1500 is shown which is provided with an o-ring shaped insert 1502, examples of which are shown in more detail in FIGS. 15C and D, in accordance with an exemplary embodiment of the invention. In some exemplary embodiments of the invention, o-ring insert 1502 is removably positioned in at least one groove 1504 located on a surface, shown more clearly in FIG. 15B, of the support arms 1506 located opposite the vaginal wall and adapted to receive o-ring insert 1502 and removably hold insert 1502 there during use of incontinence device 1500. While in use, support arms 1506 of incontinence device 1500 are urged radially outwards by o-ring insert 1502 to render support to a urethra. Optionally, the mid-urethra is supported by support arms 1506. In some exemplary embodiments of the invention, incontinence device 1500 is provided with a cover 1508, which functions similarly to other covers described herein. In some exemplary embodiments of the invention, o-ring insert 1502 is not located in groove 1504 prior to deployment of incontinence device 1500 into a vagina, and is placed there during deployment using, for example, a plunger such as described with respect to other embodiments.

FIG. 15B shows a cross-sectional view of incontinence device 1500 during removal, in accordance with an exemplary embodiment of the invention. In order to facilitate removal of incontinence device 1500, in some exemplary embodiments of the invention, a removal device 1510 is used to dislodge o-ring insert 1502 from groove 1504. Removal device 1510 is attached to o-ring insert 1502 and is also optionally attached to incontinence device 1500 to enable removal device 1510 to assist with extraction of incontinence device 1500 from the vagina in which it is being used and/or to prevent loose objects from floating around inside the user's body. In some exemplary embodiments of the invention, removal device 1510 is secured to incontinence device 1500 by threading a portion of removal device 1510 through the central node of incontinence device. In some exemplary embodiments of the invention, an enlarged portion 1512 is used to prevent removal device 1510 from pulling through the central node during removal. Force exerted on removal device 1510 in a direction away from the cervix of the user will result in dislodgment of o-ring insert 1502 from device 1500 and eventually incontinence device 1500 as a whole from vagina, in some exemplary embodiments of the invention.

Figure 16A:
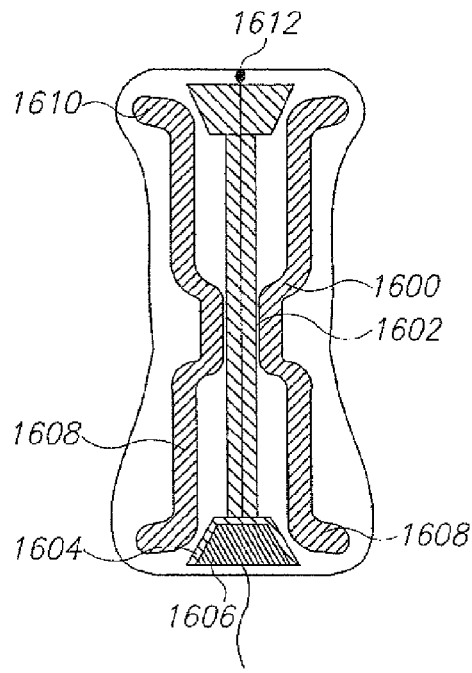
FIG. 16A is a cross-sectional view of an incontinence device with a plurality of components removably fitted together in a storage configuration, in accordance with an exemplary embodiment of the invention.
Figure 16B:
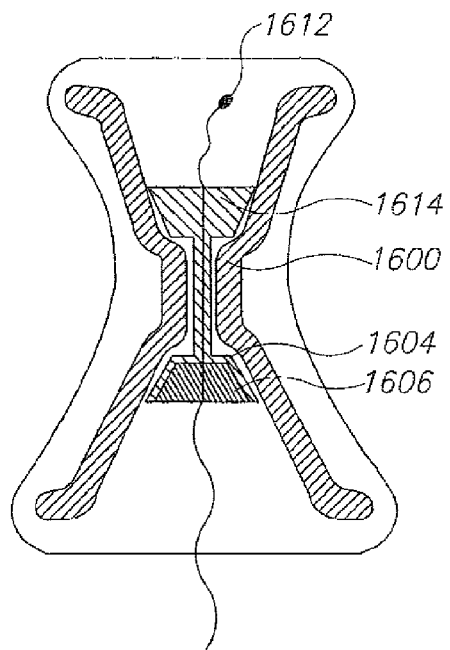
FIG. 16B is a cross-sectional view of an incontinence device with a plurality of components removably fitted together in a deployed configuration, in accordance with an exemplary embodiment of the invention.

In some exemplary embodiments of the invention, an insert 1602 which is at least partially elastic is provided to an incontinence device 1600, such as shown in FIG. 16A. FIG. 16A shows incontinence device 1600 in a storage configuration, for example if device 1600 was in an applicator. In the storage configuration, elastic insert component 1604 is stretched such that it is longer than the device 1600, such as shown in FIG. 16A. In such a configuration, the flared nature of insert 1602 does not significantly cause radial expansion of support 1608 and/or anchor arms 1610 of device 1600, such as shown in FIG. 16B. This is primarily due to stretchable nature of elastic insert component 1604 allowing insert 1602 to remain outside the realm of support 1608 and/or anchor arms 1610 of device 1600.

In some exemplary embodiments of the invention, insert 1602 is comprised of a plurality of component parts, for example elastic insert component 1604 and an addition inner insert component 1606. In some exemplary embodiments of the invention, inner insert component 1606 is adapted to removably mate with elastic insert component 1604. Optionally, inner insert component 1606 exhibits different material properties than elastic insert component 1604, for reasons described below. In an exemplary embodiment of the invention, an elastic insert component 1604 and an inner insert component 1606 are used in combination to provide radial expansion during deployment to support arms 1608 and anchor arms 1610 of the incontinence device 1600. In some exemplary embodiments of the invention, inner insert component 1606 is attached to elastic insert component 1604 with a string, which penetrates the length of elastic insert component 1604 and which is secured to elastic insert component 1604 with an expanded end 1612 at the anchoring side of device 1600. Optionally, expanded end 1612 is a knot formed by knotting and/or melting the string. It should be noted that in some exemplary embodiments of the invention the string has to be long enough to allow the stretching of elastic insert component 1604, which cups inner insert component 1606, to be longer than device 1600.

Referring to FIG. 16B, incontinence device 1600 is shown in a deployed configuration, in accordance with an exemplary embodiment of the invention. Upon deployment of device 1600 out of an applicator, the support 1608 and anchor 1610 arms are free to expand radially. In an exemplary embodiment of the invention, this freedom of movement is sufficient to allow the stretched insert 1602 to return to its nominal state. Insert 1602 unstretches causing a flared anchor end 1614 of elastic insert component 1604 to force anchor arms 1610 radially outwards and flared inner insert component 1606, cupped within elastic insert component 1604, to force support arms 1608 radially outwards as they collapse in towards the center of device 1600. In some exemplary embodiments of the invention, inner insert component 1606 is held within elastic insert component 1604 by friction between the two components. In some exemplary embodiments of the invention, elastic insert component 1604 is provided with a slight lip around its opening which helps retain inner insert component 1606 within elastic insert component 1604. In such an embodiment, the lip is not sufficient to withstand removal forces exerted on inner insert component 1606, as described below, thereby releasing inner insert component 1606 and allowing device 1600 removal.

Figure 16C:
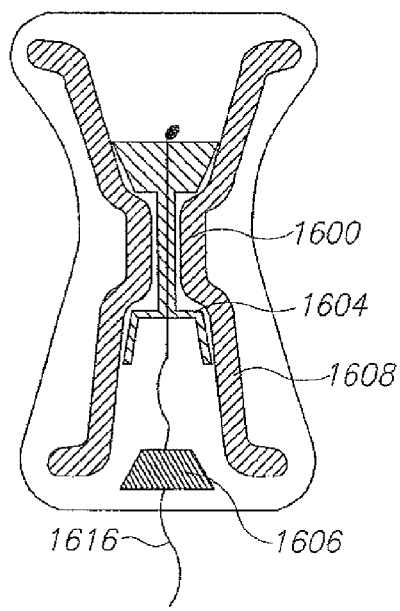
FIG. 16C is a cross-sectional view of an incontinence device with a plurality of components removably fitted together in a removal configuration, in accordance with an exemplary embodiment of the invention.

FIG. 16C shows an exemplary removal configuration of incontinence device 1600, in accordance with an exemplary embodiment of the invention. Inner insert component 1606 is optionally dislodged by pulling on a removal device 1616 in order to facilitate device 1600 removal, in some exemplary embodiments of the invention. Dislodgment of inner insert component 1606 reduces the outward radial force exerted on support arms 1608 allowing support arms 1608 to return to a nominal, less expanded state for easier removal. In some exemplary embodiments of the invention, support arms 1608 squeeze elastic insert component 1604, causing it to deform, when support arms 1608 return to their nominal state. As with other incontinence devices described herein, force on removal device 1616 away from the cervix of the user causes inner insert component 1606 to dislodge and continued force ultimately removes device 1600 from the vagina. In some exemplary embodiments of the invention, device 1600 is provided with a cover 1618.

Figure 16D:
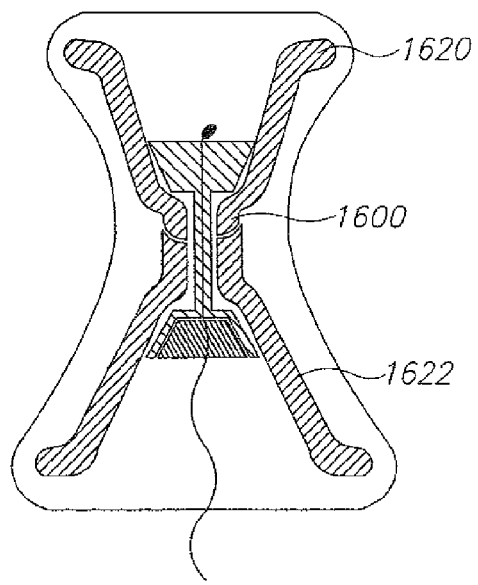
FIG. 16D is a cross-sectional view of an alternative incontinence device with a plurality of components removably fitted together in a deployed configuration, in accordance with an exemplary embodiment of the invention.

In an alternative embodiment, depicted in FIG. 16D, incontinence device 1600 is provided with a jointed central node. Optionally, the interface at the joint is like a ball joint. In some exemplary embodiments of the invention, the jointed nature of the central node results in an anchor section 1620 and a support section 1622 of device 1600 being able to move somewhat independently as a result of stresses being applied to them by movement of the wearer. In some exemplary embodiments of the invention, support section 1622 and anchor section 1620 are held in a friction causing relationship by elastic insert component 1604.

It should be noted that in some exemplary embodiments of the invention, such as those shown in FIGS. 16 and 17, at least part of the incontinence device is comprised of more than one material. Optionally, the insert is comprised of more than one material. In some exemplary embodiments of the invention, the insert is made of a first material which is at least partially flexible and/or a second material which is rigid enough to expand the support section of the incontinence device when in the proper position to do so. In some exemplary embodiments of the invention, the insert is at least more rigid than the support section of the incontinence device. In an exemplary embodiment of the invention, the first material is used for the elastic insert component 1604 and/or the second material is used for the inner insert component 1606. Selection of various materials is optionally made based on the objectives for operation of the incontinence device. For example, a more rigid material is optionally used for elastic insert component 1604 if upon removal of inner insert component 1606 it is desired that the support section still remains at least partially expanded. Optionally, a less rigid material is used for inner insert component 1606 if it is desirable to increase the comfort to the wearer and/or reduce the degree of radial expansion of the device.

Figure 17A:
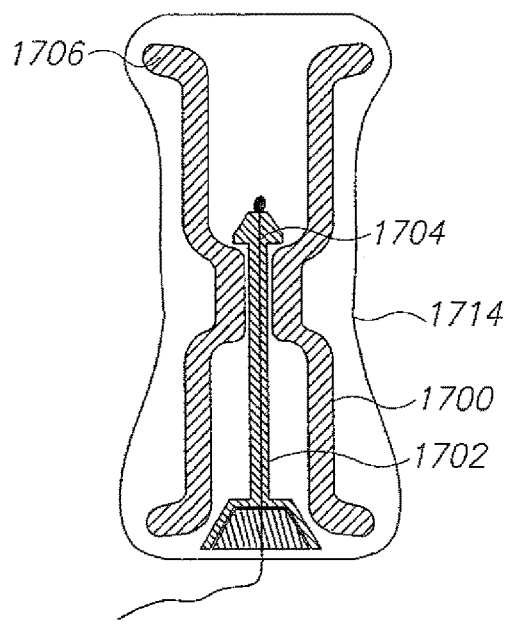
FIG. 17A is a cross-sectional view of an incontinence device with a plurality of components removably fitted together including an elastic component in a storage configuration, in accordance with an exemplary embodiment of the invention.
Figure 17B:
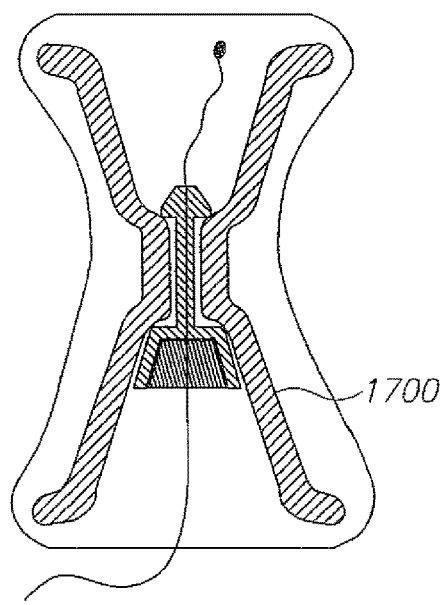
FIG. 17B is a cross-sectional view of an incontinence device with a plurality of components removably fitted together including an elastic component in a deployed configuration, in accordance with an exemplary embodiment of the invention.
Figure 17C:
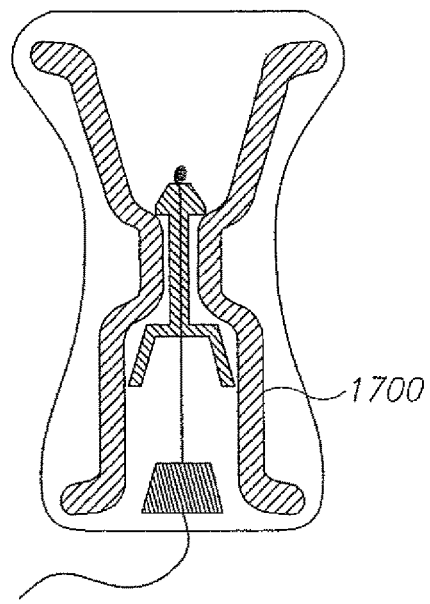
FIG. 17C is a cross-sectional view of an incontinence device with a plurality of components removably fitted together including an elastic component in a removal configuration, in accordance with an exemplary embodiment of the invention.

Referring to FIGS. 17A-C, an incontinence device 1700 is shown which also has an insert 1702 which is essentially a plurality of components removably fitted together. A difference between the incontinence device 1700 depicted in FIG. 17 and the incontinence device 1600 depicted in FIG. 16 is the anchor end 1704 of insert 1702 is not flared to cause radial expansion of the anchor arms 1706. In an exemplary embodiment of the invention, because anchor end 1704 of insert 1702 is not flared, it does not have to be outside of anchor arms 1706 during storage, which is reflected in the embodiment depicted in FIG. 17A. It can be seen that in storage, anchor end 1704 of insert 1702 does not exert radial expansion force on anchor arms 1706. FIG. 17B shows incontinence device 1700 during deployment and FIG. 17C shows device 1700 during removal. Device 1700 is optionally provided with a cover 1714. Besides providing an embodiment in which anchor arms 1706 are not radially expanded, storage stress on insert 1702 is reduced in relation to the embodiment depicted in FIGS. 16A-D because insert 1702 does not need to be stretched as far for the same sized device when in storage. In addition, upon deployment, only one side of insert 1702 needs to unstretch in order to cause radial expansion as opposed to two sides of insert 1602 (anchor and support) as shown in FIGS. 16A-D, avoiding a two stage deployment (first the anchor arms as they become free of applicator, then support arms) of device 1700.

Figure 17D:
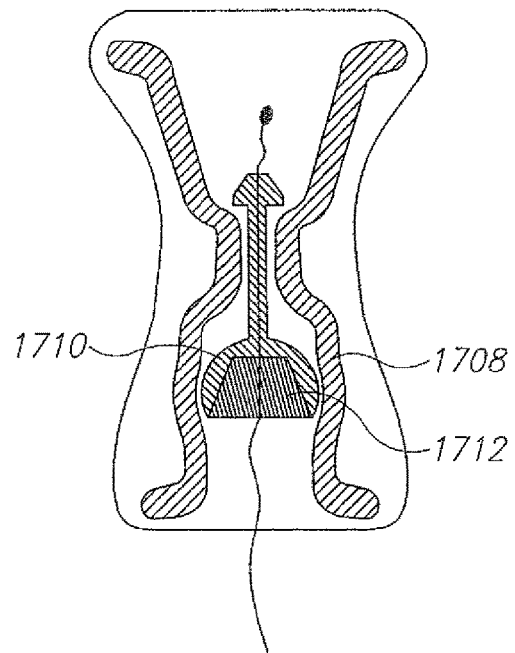
FIG. 17D is a cross-sectional view of an alternative incontinence device with a plurality of components removably fitted together including an elastic component in a deployed configuration, in accordance with an exemplary embodiment of the invention.

An alternate embodiment of incontinence device 1700 in which the support arms 1708 are configured to accommodate the elastic insert component 1710 cupping the inner insert component 1712 without them having to be outside support arms 1708 during storage, is shown in FIG. 17D. In some exemplary embodiments of the invention, this allows a shorter string connecting inner insert component 1712 to elastic insert component 1710, and also allows for a shorter elastic insert component 1710.

Figure 5:
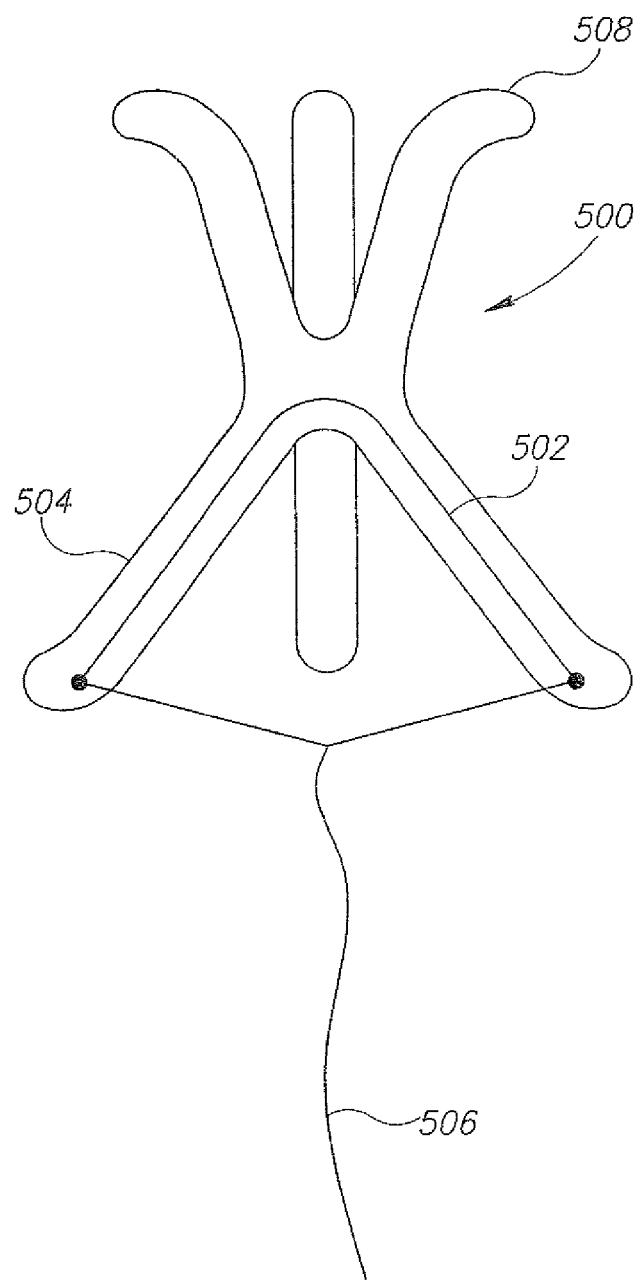
FIG. 5 is a profile view of an incontinence device with an integrated resilient support member in accordance with an exemplary embodiment of the invention.
Figure 18A:
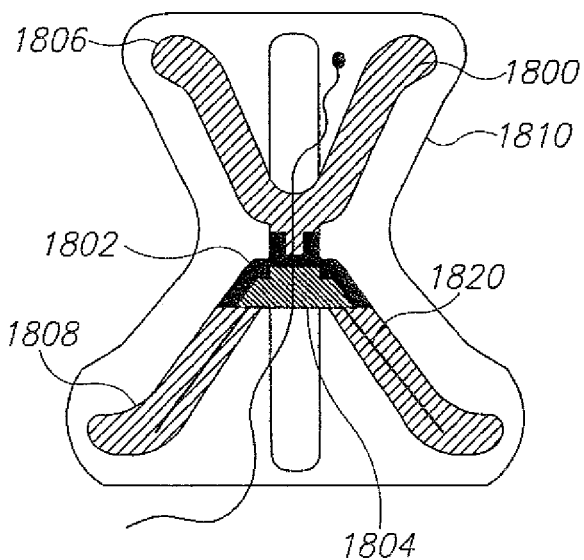
FIG. 18A is a cross-sectional view of a deployed incontinence device which uses an interlocking keystone insert, in accordance with an exemplary embodiment of the invention.

Referring to FIG. 18A, an incontinence device 1800 is shown which is provided with an insert seat 1802 adapted to removably receive an insert 1804, in accordance with an exemplary embodiment of the invention. Optionally, insert seat 1802 connects an anchoring section 1806 and a support section 1808 of incontinence device 1800 together. In an exemplary embodiment of the invention, insert 1804 is flared to provide radial expansion to insert seat 1802 and/or support section 1808 when insert 1804 is fitted into insert seat 1802. An integrated resilient support member 1820, described in more detail below with respect to FIG. 5, is shown in use with incontinence device 1800. It can be seen from FIG. 18B that in some exemplary embodiments of the invention, integrated resilient support member 1820 is adapted to cause radial expansion of support section 1808 when insert 1804 is fitted into insert seat 1802. The flared sides of insert 1804 exert pressure on the exposed ends of integrated resilient support member 1820 forcing it radially outwards, and thus support section 1808 and/or a support arm 1816 radially outwards. In an exemplary embodiment of the invention, the slope of the flared ends, and optionally their length, determines the quantity of this effect.

While FIG. 18A shows incontinence device 1800 in a deployed configuration, it should be understood that optionally insert 1804 is optionally not fitted to insert seat 1802 while in storage. For example, insert 1804 is pushed into a position fitted to insert seat 1804 by a plunger, such as described elsewhere herein, during deployment from an applicator.

Figure 18B:
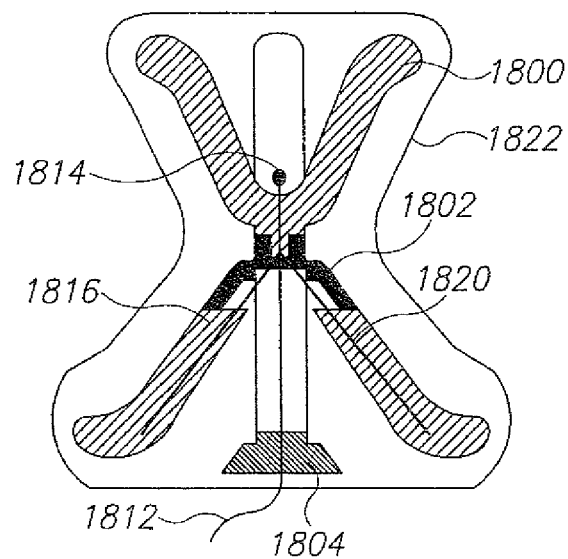
FIG. 18B is a cross-sectional view of an incontinence device which uses an interlocking keystone insert being removed, in accordance with an exemplary embodiment of the invention.

FIG. 18B shows incontinence device 1800 in a removal configuration, in accordance with an exemplary embodiment of the invention. In some exemplary embodiments of the invention, incontinence device 1800 is provided with a removal device 1812. Sufficient force applied on removal device 1812 pulling away from the user's cervix causes insert 1804 to dislodge from insert seat 1802, thereby removing the source of increased radial expansion of support section 1808 and easing the removal of device 1800. Optionally, pulling on removal device 1812 causes a collapse of at least support section 1808 and/or seat 1802 of device. Optionally, seat 1802 is predisposed to collapse inwards towards a central axis of device 1800. Force away from the user's cervix is sustained in order to pull device 1800 out of the user's vagina. An expanded end 1814 of removal device 1812 is used to prevent removal device 1812 from being pulled out of incontinence device 1800 during removal and also to prevent separation of insert 1804 from the rest of device 1800. In some exemplary embodiments of the invention, device 1800 is provided with a cover 1810, 1822.

Figure 23A:
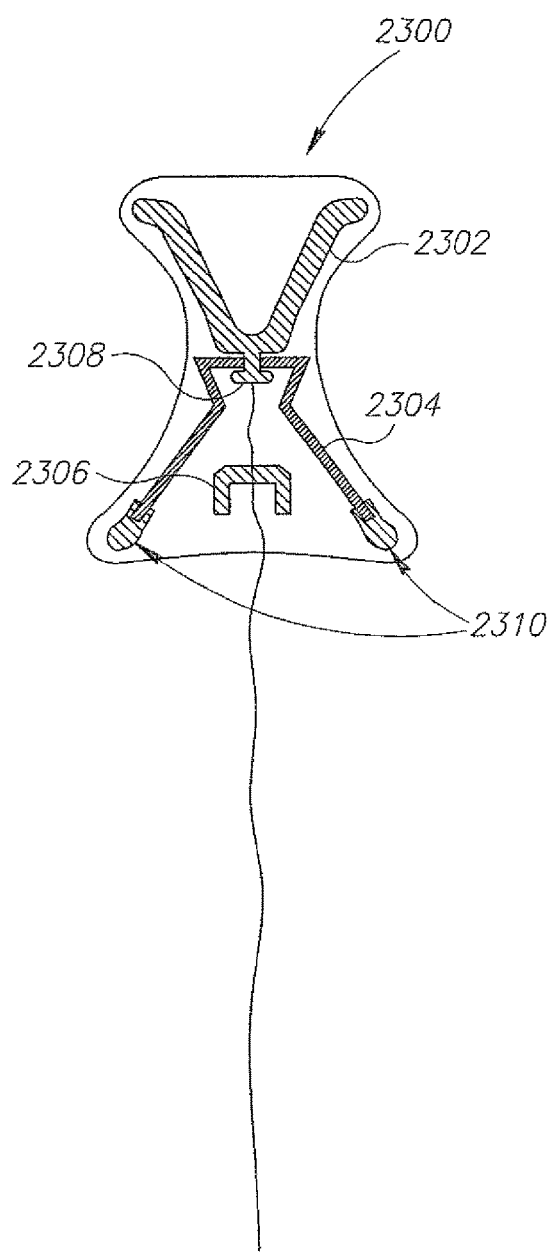
FIG. 23A is a cross-sectional view of an incontinence device provided with a leaf spring support section, in accordance with an exemplary embodiment of the invention.
Figure 23B:
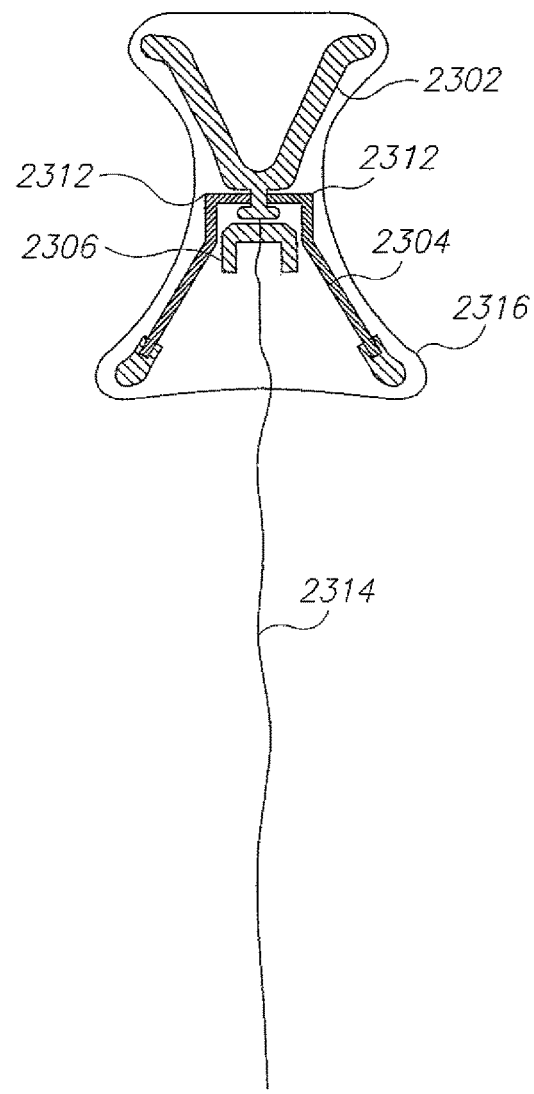
FIG. 23B is a cross-sectional view of a deployed incontinence device provided with a leaf spring support section, in accordance with an exemplary embodiment of the invention.

Referring to FIG. 23A, an incontinence device 2300 is shown which is provided with a resilient, biased support section in accordance with an exemplary embodiment of the invention. Device 2300 is comprised of at least an anchoring section 2302, a support section 2304 and an insert 2306, in an embodiment of the invention. Optionally, device 2300 includes a central node, providing an intersection and/or bridging structure between anchoring section 2302 and support section 2304. In some exemplary embodiments of the invention, support section 2304 is comprised of a plurality of arms 2310, two of which are shown in FIGS. 23A-B. In an exemplary embodiment of the invention, anchoring section 2302 is formed of a biocompatible material and operates similar to other anchoring sections described herein. Anchoring section 2302 is attached to support section 2304, for example using a tucker 2308 as shown in FIG. 23A.

In an exemplary embodiment of the invention, support section 2304 is formed such that it maintains a nominal compressed configuration (which is biased towards a central axis of device 2300), but is flexible enough to be placed into an expanded configuration by insert 2306 (as shown in FIG. 23B). In some exemplary embodiments of the invention, support section 2304 applies a modicum of support when in the compressed configuration. Optionally, support section 2304 is a leaf spring which is biased towards a central axis of device 2300. Optionally, support section 2304 is formed with an integrated resilient support member, such as shown in FIG. 5. Optionally, support section 2304 is comprised of metal. Alternatively or additionally, support section 2304 is comprised of plastic. In an exemplary embodiment of the invention, the ends of arms 2310 are capped with a biocompatible material in order to provide enhanced comfort to the user. Optionally, the material capping arms 2310 is flexible, such as rubber or plastic. In some embodiments of the invention, insert 2306 is capable of use with a device 2300 with only two support section 2304 arms 2310.

In operation, insert 2306 is forced upwards towards tucker 2308 with a plunger (not shown). Continued pressure using the plunger in this direction causes device 2300 to eventually deploy out of an applicator (not shown), assuming the deployed position depicted in FIG. 23B. FIG. 23B shows insert 2306 within support section 2304 which is flexed at flex points 2312 during the positioning of insert 2306 therein. Reconfiguration of support section 2304 to render support is a result of the positioning of insert 2306 within in an exemplary embodiment of the invention. In an exemplary embodiment of the invention, insert 2306 is maintained within support section 2304 by the compressive force applied to it by the biased support section 2304. In an embodiment of the invention, removal of device 2300 is via downward force on removal device 2314 away from cervix and towards the vaginal opening. Insert 2306 is dislodged from support section 2304 by this force on removal device 2314 allowing arms 2310 to contract to the compressed configuration and permitting comfortable removal of device 2300. In an embodiment of the invention, device 2300 is provided with a cover 2316 similar to those described elsewhere herein.

Figures 27A, 27B:
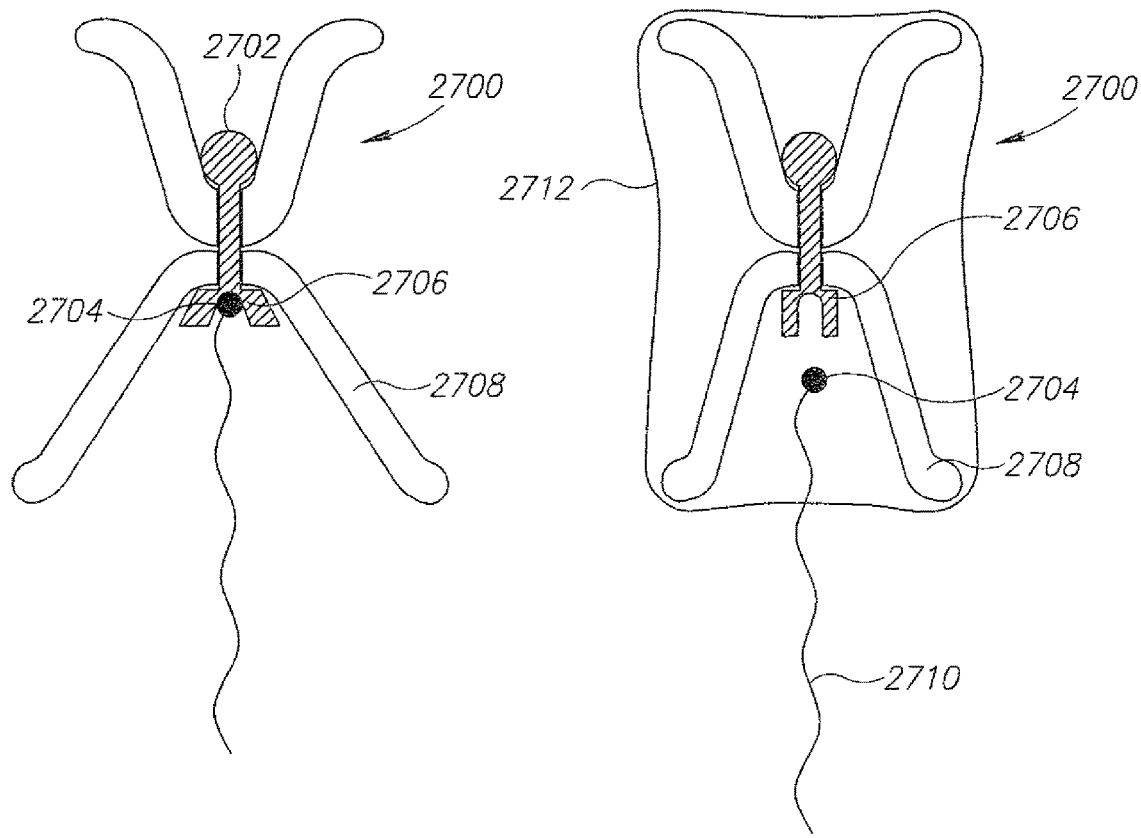
FIG. 27A is a profile view of an incontinence device with an expandable insert in a deployed configuration, in accordance with an exemplary embodiment of the invention.
FIG. 27B is a profile view of an incontinence device with an expandable insert in a removal configuration, in accordance with an exemplary embodiment of the invention.

Referring to FIG. 27A, an incontinence device 2700 is depicted with an expandable insert 2702, in accordance with an exemplary embodiment of the invention. Device 2700 is shown deployed, for example as it would be in a user's vagina. An insert head 2706 is expanded by an insert expander 2704 in a deployed configuration and in a removal configuration insert head 2706 is contracted, or contracts of its own volition, by the removal of insert expander 2704, in accordance with an exemplary embodiment of the invention. In an exemplary deployed configuration, insert expander 2704 is positioned within a slot in insert head 2706. In some embodiments of the invention, insert head 2706 is expanded by insert expander 2704, causing insert head 2706 to exert pressure on support arms 2708 of device 2700. In an embodiment of the invention, the pressure exerted by insert head 2706, as a result of insert expander 2704, causes radial expansion of support arms 2708 and subsequently treatment for incontinence. In an exemplary embodiment of the invention, insert expander 2704 is not positioned in insert head 2706 during storage. Optionally, insert head 2706 is flexible. In an exemplary embodiment of the invention, expandable insert 2702 has an expanded portion which prevents expandable insert 2702 from being pulled through device 2700 during removal, as shown in FIG. 27B.

FIG. 27B shows incontinence device 2700 in a removal configuration, in accordance with an exemplary embodiment of the invention. Removal is initiated by pulling on removal device 2710 which dislodges insert expander 2704 from insert head 2706, in some exemplary embodiments of the invention. Upon the dislodgment of insert expander 2704 from insert head 2706, insert head 2706 substantially releases the force exerted on support arms 2708, allowing them to contract, or at the minimum making them less resistant to collapsing towards a cerntral axis of device 2700, for easier and more comfortable removal of device 2700. In an embodiment of the invention, device 2700 is used with a cover 2712 which is provided with an opening which is sized such that removal device 2710 can pass, but not insert expander 2704, due to the larger size of insert expander 2704. Continued downward force on removal device 2710 away from cervix and towards the vaginal opening will eventually cause insert expander 2704 to catch on cover 2712 near the opening (since it cannot pass through the opening) and pull device 2700 out of the vagina. As described elsewhere herein, force applied on cover 2712 using removal device 2710 also assists the contraction of support arms 2708 easing removal of device 2700.

Figure 28A:
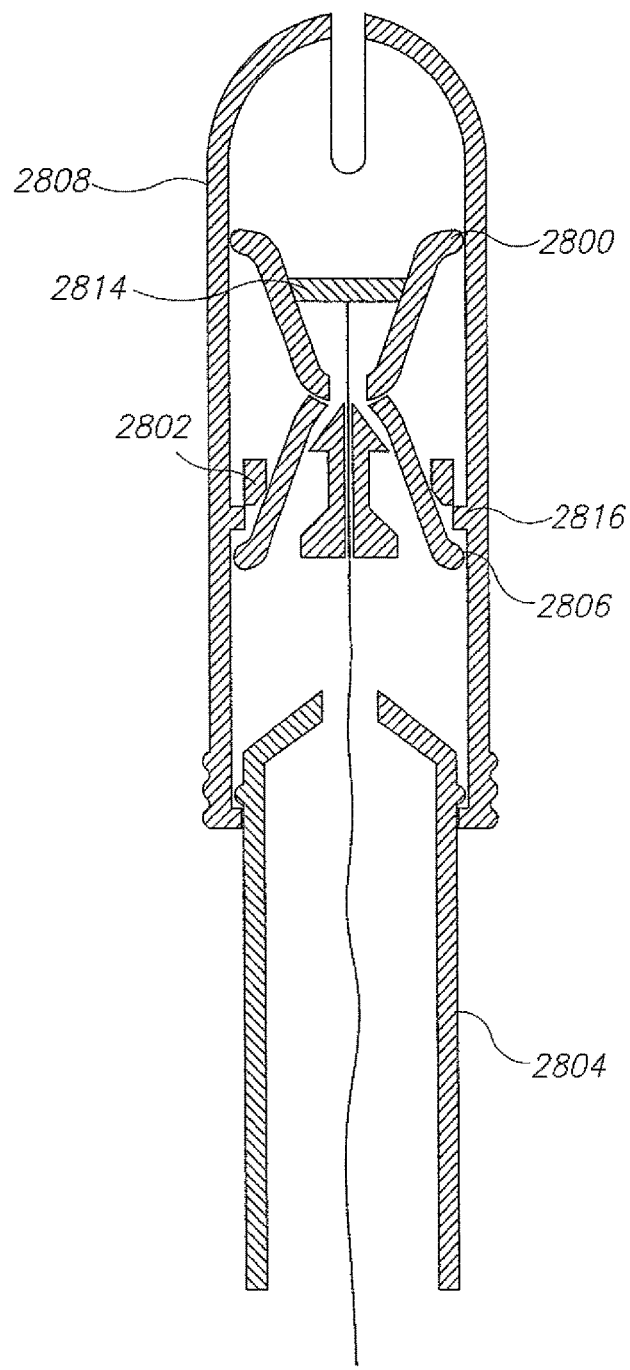
FIG. 28A is a profile view of an incontinence device with a ringed insert in a storage configuration, in accordance with an exemplary embodiment of the invention.

Referring to FIG. 28A, an incontinence device 2800 with a ringed insert 2802 is shown in a storage configuration, in accordance with an exemplary embodiment of the invention. An exemplary ringed insert 2802 can be seen in perspective in FIG. 28C. Support arms 2806 of the device pass through openings 2850 between the ring and the central portion of ringed insert 2802, in accordance with an exemplary embodiment of the invention. In some embodiments of the invention, ringed insert 2802 is not positioned within device 2800 while device 2800 is in storage, extending life and improving performance. In an exemplary embodiment of the invention, a removal/activator device 2812 is fastened to a removal/activation plate 2814 located distally from a central portion of device 2800.

In an exemplary embodiment of the invention, deployment of device 2800 is commenced by pulling down on removal/activator device 2812, causing device 2800 to move towards the proximal end of the applicator 2808, and affecting a pulling of the ringed insert 2802 into incontinence device 2800. In an exemplary embodiment of the invention, activation ledges 2816 are provided to applicator 2808 to provide a counter-force to the pulling of device 2800 onto insert 2802. Optionally, plunger 2804 is used to force insert 2802 into device 2800 to apply radial expansion force to the support arms 2806, which will assume their deployed configuration upon device 2800 ejection from applicator 2808. Deployment out of applicator 2808 and into vagina is performed as described with respect to other embodiments herein.

Figure 28B:
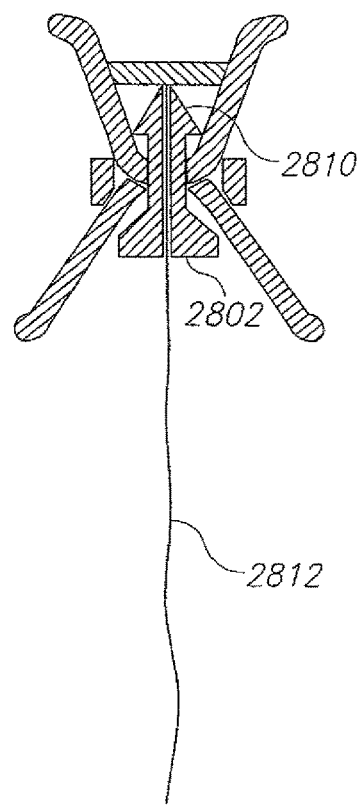
FIG. 28B is a profile view of an incontinence device with a ringed insert in a deployed configuration, in accordance with an exemplary embodiment of the invention; and, FIG. 28C is a perspective view of a ringed insert, in accordance with an exemplary embodiment of the invention.
Figure 28C:
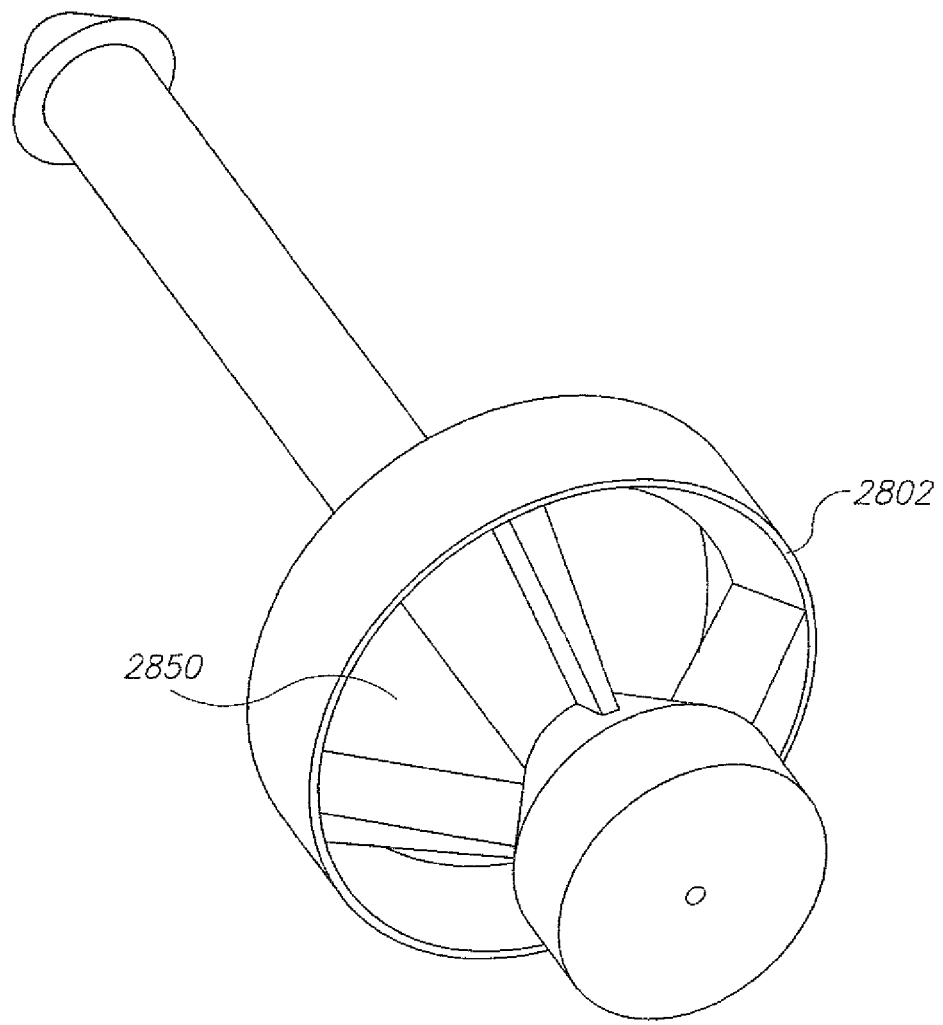

An exemplary deployed configuration of device 2800 is shown in FIG. 28B. In an embodiment of the invention, ringed insert 2802 is positioned through device 2800 such that an insert head 2810 is located at the distal side of device 2800. Optionally, insert head 2810 is shaped, for example like an arrow-head, to allow its passage through device 2800 during deployment, but to prevent passage of insert 2802 back through device 2800, to the original configuration, thereafter. In an exemplary embodiment of the invention, in a deployed configuration ringed insert 2802 applies force to support arms 2806 causing them to expand radially outwards. Optionally, device 2800 is provided with removal/activator device 2812, which, in addition to activating the incontinence device 2800, can be used like other removal devices described herein. Optionally, device 2800 is provided with a cover.

Exemplary Devices with Multiple Stable Configurations for Treating Incontinence

In some exemplary embodiments of the invention, incontinence devices are provided with multiple stable configurations for treating incontinence. Optionally, a bi-stable component is used to provide incontinence devices with a first stable position, for storage and/or removal, and a second stable position, for rendering incontinence treatment. As used herein, the bi-stable component is sometimes referred to as an insert, a locking element and/or an elastomeric ring. FIGS. 4A-C and 14A-B show exemplary embodiments of bi-stable inserts used with incontinence devices which do not substantially move in relation to the incontinence device in order to transfer from the first stable position to the second. FIGS. 3A-C, above, and FIGS. 20A-C, described below in another section, show an exemplary embodiment of a bi-stable device where the bi-stable component moves in relation to the incontinence device when transferring from the first stable position to the second stable position. It should also be noted that in an exemplary embodiment of the invention, deployment of the bi-stable devices occurs after the devices are properly positioned within the vagina, "popping" into their second stable position when the bi-stable insert is switched to the second position. In an exemplary embodiment of the invention, popping deployment is more comfortable than other forms of deployment described herein because the support arms do not exert pressure against the vaginal wall until the incontinence device is already in a position to render incontinence treatment.

Figure 4C:
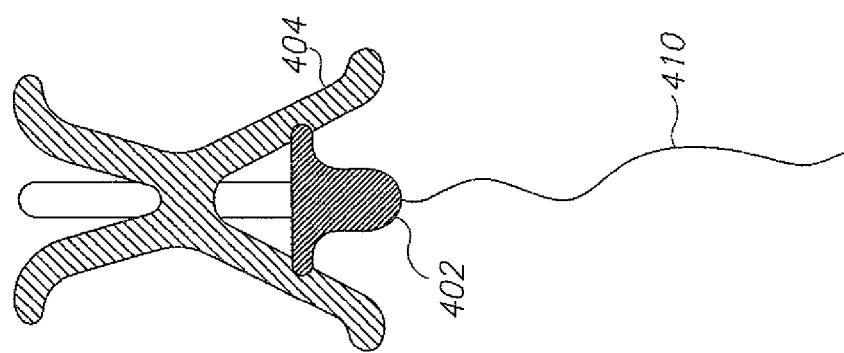
FIG. 4C is a profile view of an incontinence device with an inverting insert during removal in an exemplary embodiment of the invention.
Figure 4B:
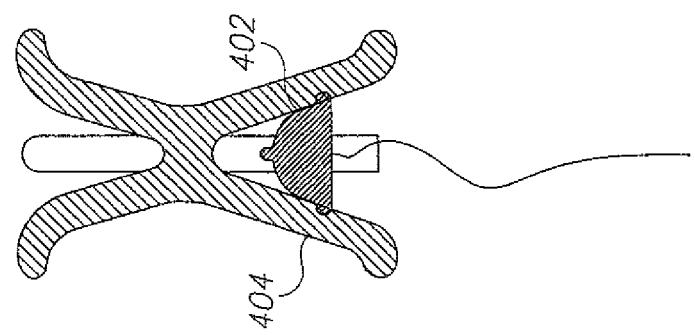
FIG. 4B is a profile view of an incontinence device with an inverting insert deployed in accordance with an exemplary embodiment of the invention.
Figure 4A:
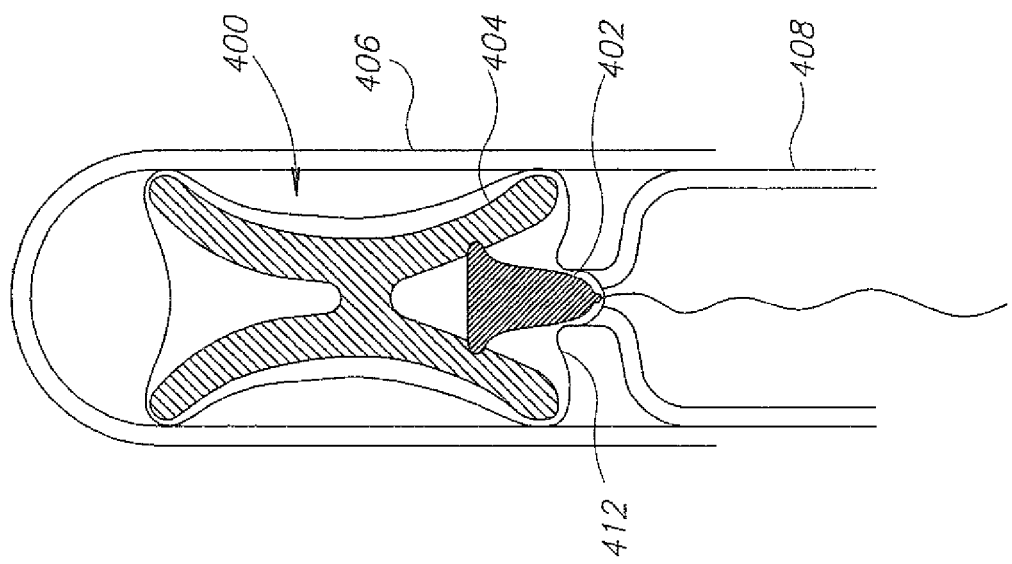
FIG. 4A is a profile view of an incontinence device with an inverting insert located in an applicator in accordance with an exemplary embodiment of the invention.

FIG. 4A is a profile view of an incontinence device 400 with an inverting, bi-stable insert 402 located in an applicator 406 in accordance with an exemplary embodiment of the invention. Inverting insert 402 resembles a flexible bowl-shaped membrane, in an exemplary embodiment of the invention. Insert 402 is constructed such that when membrane is biased towards the proximal end of device 400 in a first configuration, insert 402 membrane is flaccid. However, when the membrane is pushed through the center of insert 402 towards the distal end of device 400, the insert 402 membrane exerts radially expanding pressure on the support arms 404 of device 400 and the arms 404 "pop" into position. In an exemplary embodiment of the invention, insert 402 membrane has variable wall width, and therefore, different tension at every point. Optionally, insert 402 is located between support arms 404 of device 400. Optionally, insert membrane 402 is pushed through its own center, thereby deploying device 400 into a second configuration, by a plunger 408 located at the proximal end of applicator 406.

FIG. 4B is a profile view of incontinence device 400 with an inverting insert 402 deployed, in accordance with an exemplary embodiment of the invention. It can be seen in this exemplary embodiment that during deployment plunger 408 pushed insert 402 membrane through its center, biasing it towards the distal end of device 400. As described herein, the membrane is constructed so that when it is biased towards the proximal end of device 400 it is flaccid, and when it is biased towards the distal end of device 400 it is sufficiently rigid to apply radial pressure to support arms 404 causing them to increase their diameter for urethral support. Optionally, the urethral support is mid-urethral.

Removal of device 400 is depicted in FIG. 4C, which shows a profile view of incontinence device 400 with an optional removal device 410, such as a string. Force on removal device 410 in a proximal direction, away from the cervix, causes insert 402 membrane to re-invert transforming membrane from at least semi-rigid to flaccid. The reduced radial pressure exerted by insert 402 membrane facilitates the movement of support arms 404 towards the central axis of device 400 for easier removal. In some exemplary embodiments of the invention, continued force on removal device 410 pulls support arms 404 towards the central axis of device 400 and towards the vaginal opening. Additionally, alternatively or optionally, removal device 410 is fastened to a cover 412 which, when downward force is applied to removal device 410, exerts pressure on support arms 404 towards the central axis of device 400 for easier removal. The embodiment depicted in FIGS. 4A-C is optionally used with an integrated resilient support, as described below with respect to FIG. 5.

Figure 14A:
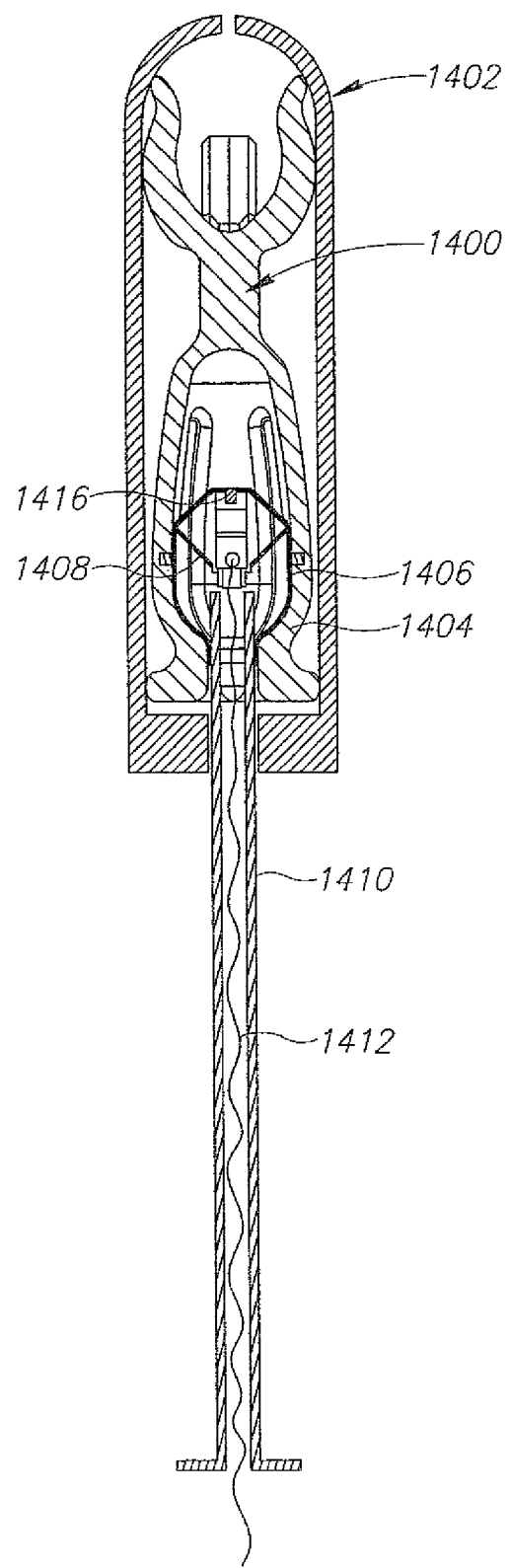
FIG. 14A is a cutaway view of an applicator containing a bi-stable incontinence device within accordance with an exemplary embodiment of the invention.
Figure 14B:
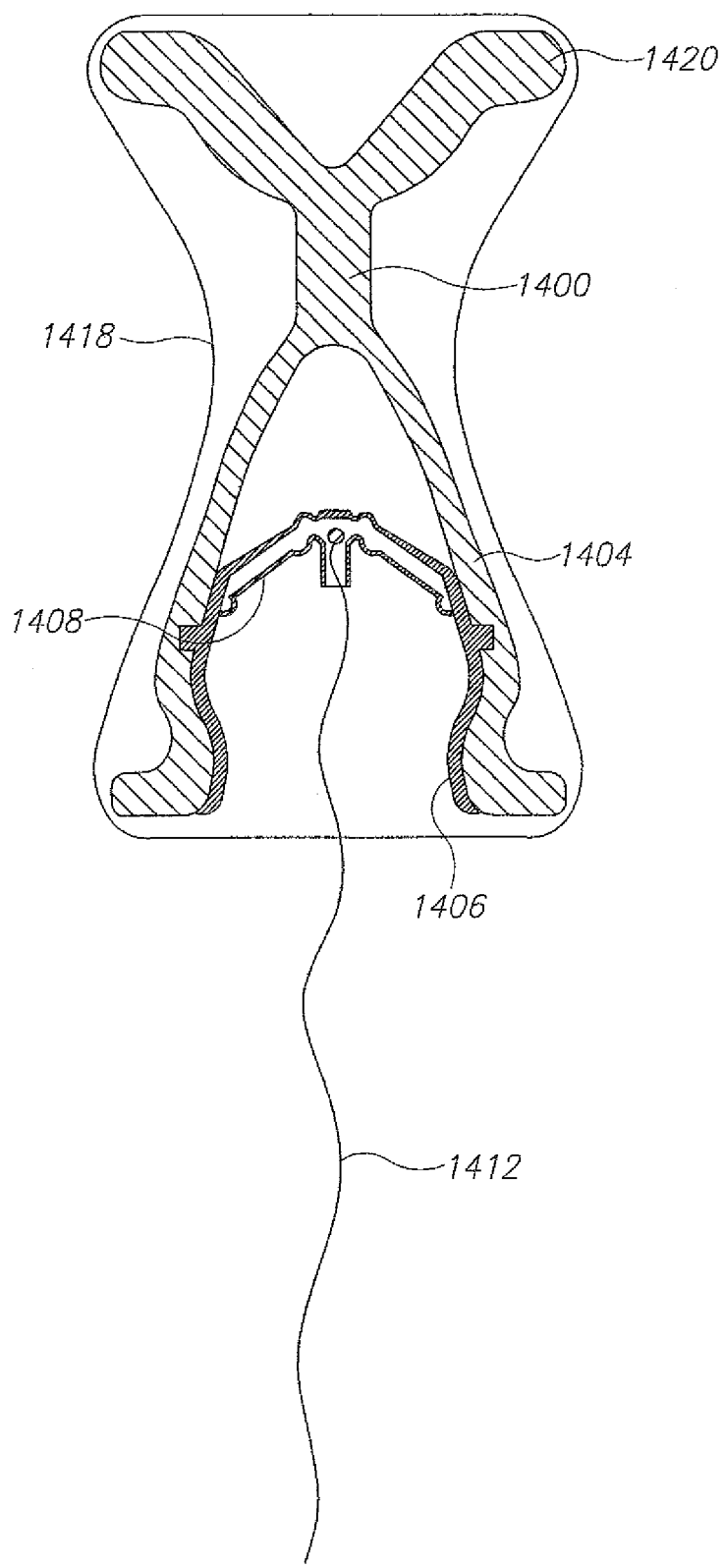
FIG. 14B is a bi-stable incontinence device in a deployed configuration in accordance with an exemplary embodiment of the invention.

Referring to FIG. 14A, a cutaway view of an applicator 1402 is shown, depicting a bi-stable incontinence device 1400 therein, in accordance with an exemplary embodiment of the invention. The bi-stable insert of FIGS. 14A-B is different from that of FIGS. 4A-C in that rather than using a membrane which exhibits first and second stable positions depending on its bias, mechanical arms are provided which exhibit first and second stable positions. As described with respect to other incontinence device embodiments herein, bi-stable incontinence device 1400 is configured in a reduced diameter form for storage within applicator 1402. Applicator 1402 is, optionally, similar to any of the applicators described herein and in related applications, known to those skilled in the art or not yet invented. In an exemplary embodiment of the invention, bi-stable incontinence device 1400 is provided with a bi-stable locking element 1408 which is attached to a support arm reinforcing element 1406. Bi-stable locking element 1408 is optionally configured such that in a first stable position, wherein the bi-stable locking element 1408 is biased towards support arms 1404 of device 1400, bi-stable locking element 1408 does not substantially urge support arm reinforcing element 1406 radially outwards. However, in a second stable position, wherein bi-stable locking element 1408 is biased towards the anchoring arms 1420, shown in FIG. 14B, of device 1400, bi-stable locking element 1408 applies force to support arm reinforcing element 1406 causing support arms 1404 to urge radially outwards from a central axis of incontinence device 1400. In some exemplary embodiments of the invention, a plurality of reinforcing arms are attached to the support arms 1404 of incontinence device 1400 such that when bi-stable locking element 1408 is in the second stable position reinforcing arms urge support arms 1404 radially outward from a central axis of device 1400. Optionally, each support arm 1404 is provided with a reinforcing arm. Optionally, selected support arms 1404 are supplied with reinforcing arms, for example if forced deployment of support arms 1404 is only desired along a single axis.

In some exemplary embodiments of the invention, support arm reinforcing element 1406 has a central portion with a male locking cylinder 1416. Optionally, bi-stable locking element 1408 is provided with a central female locking cylinder receiver, which allows for bi-stable locking element 1408 to be removably fastened to support arm reinforcing element 1406. Removably fastening bi-stable locking element to support arm reinforcing element counters pressure from the vaginal wall which acts to force device 1400 into the first stable position. Optionally, locking cylinder 1416 is provided with a lip which is sized slightly larger than an inner circumference of the locking cylinder receiver, which is optionally a hole located on bi-stable locking element, such then when locking cylinder 1416 is urged against locking cylinder 1416 with sufficient force the receiver passes over the lip and becomes removably fastened to support arm reinforcing element 1406. Optionally, bi-stable locking element 1408 is biased such that when urged towards support arm reinforcing element 1406, bi-stable locking element 1408 removably locks into a reinforcing position without the need for lockably mating locking cylinder 1416 with locking cylinder receiver. In some exemplary embodiments of the invention, bi-stable locking element 1408 is urged towards support arm reinforcing element 1406 by a plunger 1410. Optionally, the anchoring force provided by anchoring arms 1420 is more than the force required to switch support arm reinforcing element 1406 from the first stable position to the second stable position such that upon the insertion of device 1400 into the vagina, when anchoring arms 1420 are in position, they prevent device 1400 from moving towards the cervix as pressure to "pop" into the second stable position is exerted on support arm reinforcing element 1406 by plunger. Optionally, incontinence device 1400 is provided with a removal device 1412 which is attached to bi-stable locking element 1408 such that it can change the position of bi-stable locking element 1408 from the second stable position to the first stable position.

Referring to FIG. 14B, bi-stable incontinence device 1400 is shown deployed in the second stable position, in accordance with an exemplary embodiment of the invention. It can be seen that bi-stable locking element 1408 is urged against support arm reinforcing element 1406, urging the reinforcing arms radially outwards, and hence support arms 1404 radially outwards from a central axis of device 1400. In an exemplary embodiment of the invention, support arms 1404 provide support to a urethra. Optionally, the support is mid-urethral support. Optionally, device 1400 is used in conjunction with a cover 1418, such as those described herein. Removal of device 1400 is optionally facilitated by exerting a downward force on removal device 1412 towards a vaginal opening. This downward force causes bi-stable locking element 1408 to change from the second stable position to the first stable position, removing reinforcement from support arms 1404 and allowing them to converge on a central axis of device 1400. The reduction in radial diameter of device 1400 due to this convergence enables an easier and/or more comfortable removal than if support arms 1404 had remained deployed.

In an exemplary embodiment of the invention, bi-stable locking element 1408 is provided with reinforcing arms and the central portion of support arm reinforcing element 1406 is omitted.

Exemplary Elastomeric Ring Incontinence Devices

Figure 20A:
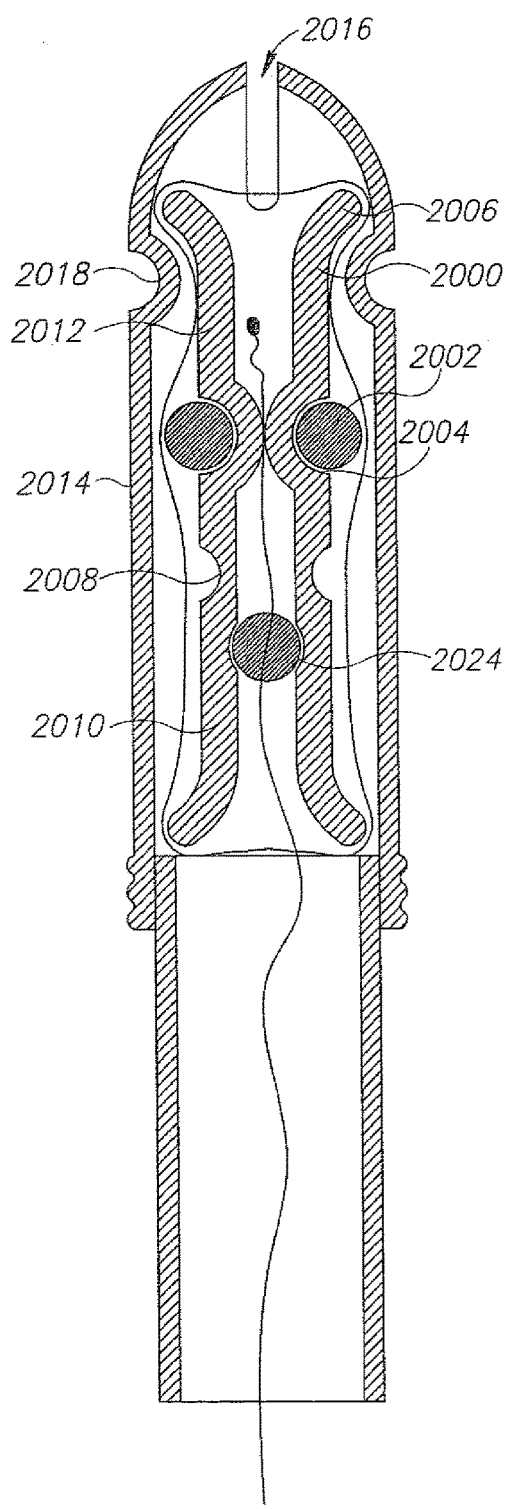
FIG. 20A is a cross-sectional view of an incontinence device provided with an elastomeric ring in a storage configuration, in accordance with an exemplary embodiment of the invention.
Figure 20B:
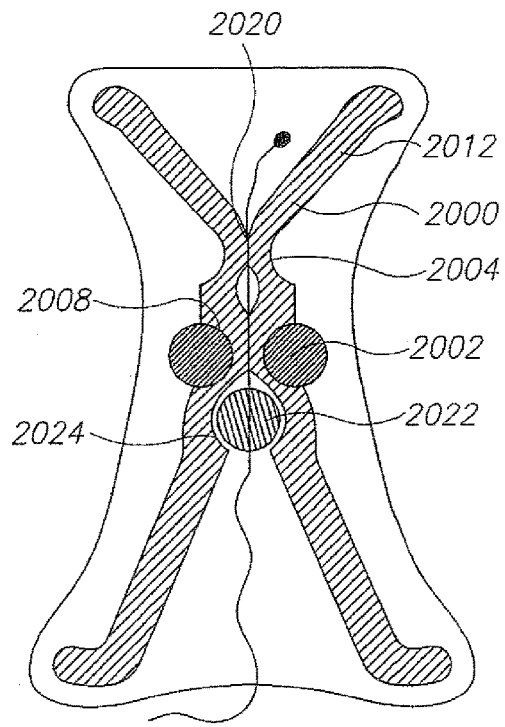
FIG. 20B is a cross-sectional view of an incontinence device provided with an elastomeric ring in a deployed configuration, in accordance with an exemplary embodiment of the invention.
Figure 20C:
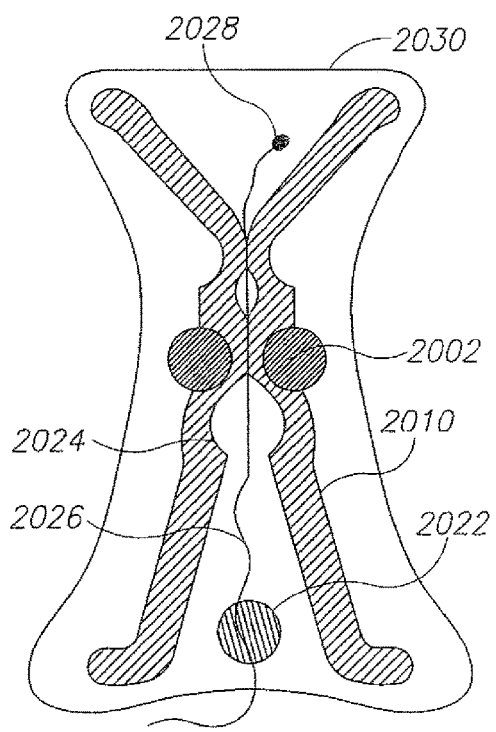
FIG. 20C is a cross-sectional view of an incontinence device provided with an elastomeric ring in a removal configuration, in accordance with an exemplary embodiment of the invention.

Some of the embodiments described in this section are provided with multiple stable configurations, for example those depicted in FIGS. 20A-C. In some exemplary embodiments of the invention, an elastomeric ring 2002 is used to provide an incontinence device 2000 with radial expansion and/or contraction, depending on whether ring 2002 is in the first stable position or the second stable position. Optionally, radial expansion and/or contraction is caused by material properties and/or configuration of an incontinence device and a ring is selectively positioned to prevent specific configurations from manifesting themselves. Referring to FIG. 20A, incontinence device 2000 is shown in a first stable position, or a storage configuration, in accordance with an exemplary embodiment of the invention. Elastomeric ring 2002 is initially located in a first groove 2004, situated between an anchor section 2006 of incontinence device 2000 and a second groove 2008 in some exemplary embodiments of the invention, is used to help maintain device 2000 in a storage configuration. In an exemplary embodiment of the invention, first groove 2004 is situated on body of device 2000 where when elastomeric ring 2002 applies pressure to device 2000 from first groove 2004 support 2010 and anchor 2012 arms are not urged radially outwards.

In some exemplary embodiments of the invention, elastomeric ring 2002 is comprised of latex, rubber, silicone, polyurethane or nylon. Optionally, elastomeric ring 2002 is constructed of any at least slightly elastic material. In some exemplary embodiments of the invention, the elastomeric ring is not elastic and/or flexible. In some exemplary embodiments of the invention, elasticity and/or flexibility aid elastomeric ring 2002 in moving from first groove 2004 to second groove 2008 and/or remaining in the grooves 2004, 2008. For example, in some exemplary embodiments of the invention, ring 2002 uses its elastic ability, like a rubber band, to apply pressure to device 2000 while ring 2002 is in a groove, thereby helping to retain ring 2002 in the groove and also in the case of first groove 2004 holding device in a storage configuration and in the case of second groove 2008 helping the radial expansion of support 2010 and anchor 2012 arms. Optionally, the elastomeric ring is not ring shaped, it is optionally square, rectangular, triangular, ovoid, or u-shaped, for example.

Deployment of incontinence device 2000 transitions elastomeric ring 2002 from a first stable position where ring 2002 is located in a first groove 2004 to a second stable position, where ring 2002 is located in a second groove 2008, in accordance with some exemplary embodiments of the invention. As device 2000 moves in an applicator 2014 towards an applicator exit 2016, elastomeric ring 2002 hits a transition element 2018 located on the interior surface of applicator 2014. Device 2000 is subjected to sustained pressure for deployment, urging device 2000 out of applicator 2014, while elastomeric ring 2002 is pushed by transition element 2018 down the exterior surface of device 2000 until it settles into second groove 2008. In some exemplary embodiments of the invention, second groove 2008 is adapted to prevent further movement of elastomeric ring 2002 as a result of transition element 2018, and further pressure on device 2000 deploys device 2000 into position, optionally in the user's vagina. Optionally, first groove 2004 and/or second groove 2008 are adapted to allow movement of ring 2002 out of first groove 2004 as a result of encountering transition element 2018 but to prevent movement of ring 2002 out of second groove 2008. For example, second groove 2008 is deeper than first groove 2004 in some exemplary embodiments of the invention.

FIG. 20B shows incontinence device 2000 in the second stable position, or in a deployment configuration, where elastomeric ring 2002 is located in second groove 2008, in accordance with an exemplary embodiment of the invention. When elastomeric ring 2002 is located in second groove 2008, anchor arms 2012 are urged radially outwards in part because of the compressive force exerted by elastomeric ring 2002 at its second groove 2008 position towards a central axis of device 2000 and because of a pivot point 2020 created by the curvature of device 2000 at first groove 2004 location. In some exemplary embodiments of the invention, the pivot point is created by the meeting of the two points on at least two of the anchor arms which are the lowest in the curvature of first groove 2004. In an exemplary embodiment of the invention, the support arms 2010 do not derive the benefit of a curved groove, like first groove 2004, therefore a pivot point is provided by positioning a pivot piece 2022 between elastomeric ring 2002 and support arms 2010. Optionally, pivot piece 2022 is a ball. In some exemplary embodiments of the invention, pivot piece 2022 is situated in a third groove 2024 adapted to receive pivot piece 2022 and prevent it from falling out prior to removal. As above, the pressure exerted by elastomeric ring 2002 and pivot piece 2022 causes support arms 2010 to expand radially. In some exemplary embodiments of the invention, the pressure exerted on device 2000 by elastomeric ring 2002 is varied depending on the length of the lever between ring 2002 and a pivot point (pivot point 2020 and/or pivot piece 2022) and/or the effect desired to be achieved on device 2000. Additionally or alternatively, the flexibility of the material from which device 2000 is constructed is also taken into consideration.

Referring to FIG. 20C, incontinence device 2000 is shown in a removal configuration, in accordance with an exemplary embodiment of the invention. The radial profile of at least a portion of incontinence device 2000 is reduced to ease removal of device 2000, in some exemplary embodiments of the invention. Optionally, reduction of the radial profile is accomplished by dislodging pivot piece 2022 using a removal device 2026 attached to pivot piece 2022. In an exemplary embodiment of the invention, force applied on removal device 2026 away from cervix and towards the direction of the user's vaginal opening causes pivot piece 2022 to dislodge from third groove 2024. This dislodgement of pivot piece 2022 removes a part of the mechanism from which support arms 2010 were deriving radial expansion, allowing support arms 2010 to return to a reduced radial profile configuration. Sustained force on removal device 2026 away from the cervix eventually removes device 2000 from the user's vagina. Removal device 2026 is optionally secured to incontinence device 2000 by threading it through the central node of device 2000 and provided an enlarged end 2028 to prevent removal device 2026 from being pulled out of device during removal. In some exemplary embodiments of the invention, device 2000 is provided with a cover 2030.

While not necessarily a bi-stable device in some exemplary embodiments of the invention, the device depicted in FIG. 20D shows another exemplary embodiment of an incontinence device 2050 which uses an elastomeric ring 2052 to selectively apply pressure to device 2050. Incontinence device 2050 depicted in FIG. 20D is similar to many of the other embodiments described herein, which use an insert 2054 to radially expand support arms 2056 and/or to provide support to support arms 2056 against the counter-pressure exerted by the vaginal wall, and in this embodiment elastomeric ring 2052, when device 2050 is deployed. Optional insert configurations which could be used with any of the embodiments described herein are depicted in FIGS. 20E-I. In some exemplary embodiments of the invention, the hollow passage traversing the center of the inserts is to allow the passage of a removal device. In some exemplary embodiments of the invention, the inserts are configured to achieve various radial expansion effects on the support arms of the incontinence device. Optionally, the inserts are configured to be removably attached to the incontinence device.

In an exemplary embodiment of the invention, elastomeric ring 2052 acts in concert with the removal of insert 2054 to force radial contraction of support arms 2056 in order to ease removal of device 2050. In an exemplary embodiment of the invention, force applied to a removal device 2058, as shown in FIG. 20E, dislodges insert 2054. This allows support arms 2056 the freedom to converge towards the central axis of device 2050, and elastomeric ring 2052 applies pressure to support arms 2056 to reinforce this contracting motion. In an exemplary embodiment of the invention, upon sustained force away from the cervix of the user, the device 2050 is removed from the user's vagina.

An Exemplary Integrated Resilient Support Member Embodiment

FIG. 5 is a profile view of an incontinence device 500 with an integrated resilient support member 502, in accordance with an exemplary embodiment of the invention. Optionally, device 500 is any of the devices described herein. In an exemplary embodiment of the invention, resilient support member 502 is used to bias the support arms 504 of device 500. Optionally, support arms 504 are biased in an expanded radial configuration. Optionally, support arms 504 are biased in a compact radial configuration. Optionally, integrated support member 502 is embedded within device 500. Optionally, integrated support member 502 is located externally of the device 500, like an exoskeleton. In some exemplary embodiments of the invention, integrated support member 502 is used in conjunction with the support arms 504 of device 500. Integrated support member 502 is optionally constructed of a material with an enduring shape memory (such as stainless steel or polymers, such as nylon or silicone based materials). In an exemplary embodiment of the invention, a shape memory integrated support member 502 imparts to device 500 an extended shelf life since compressed in the applicator for an extended time will not substantially diminish the integrated support member's 502 spring coefficient. Integrated support member 502 is designed such that when device 500 is deployed from an applicator, integrated support member 502 forces support arms 504 to deploy radially outwards from the central axis of device 500 for urethral support. Optionally, an integrated support member is used with the anchor arms 508.

Removal of device 500 is assisted by attaching a removal device 506 to support arms 504. Downward force on removal device 506 away from the cervix causes support arms 504 to converge on the central axis of device 500 enabling easier and/or more comfortable removal. Optionally, removal device 506 and integrated support member 502 are constructed of the same material. Optionally, removal device 506 and integrated support member 502 are manufactured simultaneously. In other exemplary embodiments of the invention, integrated support members are used which bias support and/or anchor arms towards the central axis of device 500 instead of away from the central axis. Such a configuration is optionally used to provide better arm convergence for easier incontinence device removal.

Exemplary Tension Reducing Arms Embodiment

Figure 6:
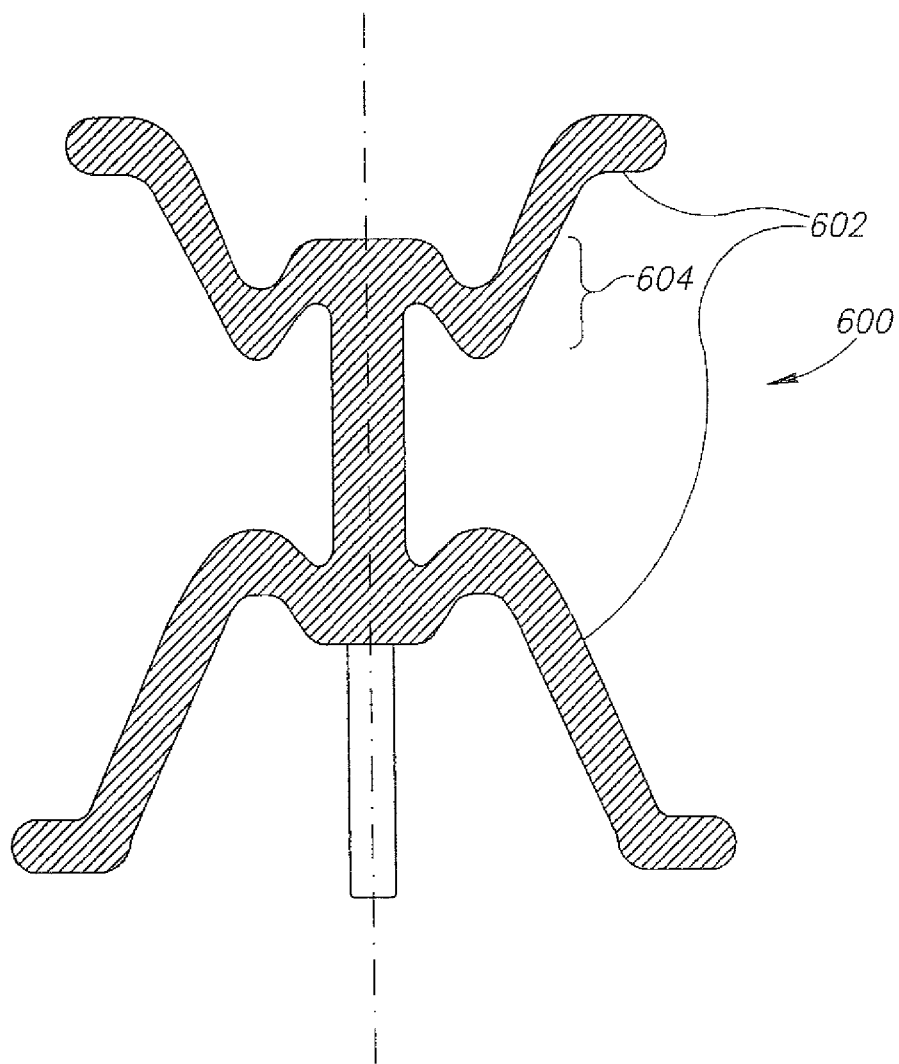
FIG. 6 is a profile view of an incontinence device provided with tension reducing arms in accordance with an exemplary embodiment of the invention.

Referring to FIG. 6, a profile view of an incontinence device 600 provided with tension reducing support and/or anchor arms 602 is shown, in accordance with an exemplary embodiment of the invention. Reduction in tension in support and/or anchor arms 602 extends the shelf life of device 600. In an exemplary embodiment of the invention, the area of an incontinence device which undergoes the most stress and/or tension, the joint between the support and/or anchor arms and the node, is reconfigured to distribute that stress and/or tension. Optionally, the stress and/or tension are reduced by spreading it out of a greater area of the device. In an exemplary embodiment of the invention, tension is optionally reduced on support and/or anchor arms 602 by providing them with an accordion-like section 604 which folds in on itself when compressed within an applicator. Optionally, folding is accomplished without the use of hinges and/or other mechanical means. Optionally, other devices such as described herein are provided with tension reducing arms such as shown in FIG. 6. However, upon deployment from the applicator, in an exemplary embodiment of the invention, support and/or anchor arms 602 deploy themselves to expand radially from the central axis of device 500. In an exemplary embodiment of the invention, arms 602 deploy to render mid-urethral support. Optionally, device 600 is used in conjunction with a cover, such as those described herein. In some exemplary embodiments of the invention, device removal is facilitated by applying a downward force, away from the cervix, to a removal device attached to the cover encapsulating device 600. As described in other embodiments herein, this force causes the arms of device 600 to converge towards the central axis of device 600, enabling an easier and/or more comfortable removal than without the arm convergence.

In an exemplary embodiment of the invention, an additional benefit of some embodiments of tension reducing devices is greater flexibility in device size and/or applicator size. Optionally, the tension reduction configuration described herein permits the use of an incontinence device that has a wider diameter than would normally be suitable for use with an applicator, for example in the use of prolapse devices, which generally require a larger diameter. Alternatively, a narrower applicator can be used for a tension reducing device which when deployed exhibits a similar radius to a non-tension reducing embodiment. In an exemplary embodiment of the invention, this is due to the folding nature of arms 602 which occupy less space when folded than when arms 602 are at full expansion. In another exemplary embodiment of the invention, folding arms enable the use of a longer central node than would typically fit in an applicator, by increasing the length of folding accordion section 604.

Exemplary Scrolling Incontinence Devices

In some exemplary embodiments of the invention, incontinence devices comprising at least one scrolling section are provided. Exemplary embodiments are depicted in FIGS. 7A-D and 8. These devices 700, 800 are distinguishable in at least one aspect from other incontinence devices described herein, in that rather than the support and/or anchor arms converging towards a central axis in order to reduce the radial profile of the device, the scrolling sections are provided with the ability to roll up to reduce the radial profile of the device.

Referring to FIG. 7A, a profile view of a scrolling incontinence device 700 is shown, in accordance with an exemplary embodiment of the invention. Device 700 is comprised of a central member 702, which when deployed optionally has a generally cylindrical shape. Optionally, located at or near the proximal and distal ends of central member 702 are support arms 704 (proximal end) and anchor arms 706 (at distal end). In some exemplary embodiments of the invention, central member 702 is comprised of a rolled sheet provided with arms 704, 706, as described more in detail with respect to FIG. 7C. In some exemplary embodiments of the invention, a removal device 708 is attached to device 700 to facilitate removal. Removal device 708 is optionally attached to device 700 such that when a downward force is applied to removal device 708 away from the cervix, device 700 exhibits a deforming behavior towards the vaginal opening thereby reducing its profile for easier removal. For example, a removal force on removal device 708 optionally deforms the proximal end of device 700 into a conical-like shape, with the peak pointed towards the vaginal opening.

FIG. 7B is a profile view of another scrolling incontinence device 720 embodiment, wherein device 720 has a flared proximal end, in accordance with an exemplary embodiment of the invention. A flared proximal end is optionally desirable in the treatment of incontinence in order to provide additional support with the support arms 722 over device 700, which does not have a flared proximal end. In an exemplary embodiment of the invention, a flared proximal end allows the length of support arms 722 to be shorter, reducing a source of potential discomfort upon deployment and/or use of device 720. Optionally, support arms 704, 722 are variable in length depending on the requirements of the patient. Optionally, anchor arms 706 located at the distal end of devices 700, 720 are variable in length depending on the requirements of the patient. Optionally, support and/or anchor arms are sufficiently long to prevent vaginal tissue from becoming caught in the crease between the two ends of central member 702. In some exemplary embodiments of the invention, the support and/or anchor arms are up to 10 mm in length. Optionally, the arms are longer than 10 mms. Optionally, the arms are less than 5 mm in length. Optionally, support is rendered to the mid-urethra.

A top or bottom view of scrolling incontinence device 700, in accordance with an exemplary embodiment of the invention, is shown in FIG. 7C. It can be seen that when viewed in conjunction with FIG. 7A, central member 702 is optionally, generally cylindrical in shape. In some exemplary embodiments of the invention, central member 702 is comprised of a sheet, which is rolled to provide the generally cylindrical shape. Optionally, the sheet is comprised of a material which is biased to cause the sheet to open from the cylindrical shape but which is prevented from doing so when in an applicator or in a vagina, for example.

Therefore, in an exemplary application, device 700 is rolled up like a scroll and placed in an applicator 730, shown in FIG. 7D. Device 700 is rolled such that its natural bias to open will cause device 700 to expand into its generally cylindrical shape, and also exert at least some outward radial support pressure, upon deployment from applicator 730. Optionally, support pressure is directed towards the mid-urethra. Optionally, device 720 is used as described herein with respect to device 700.

Figure 8:
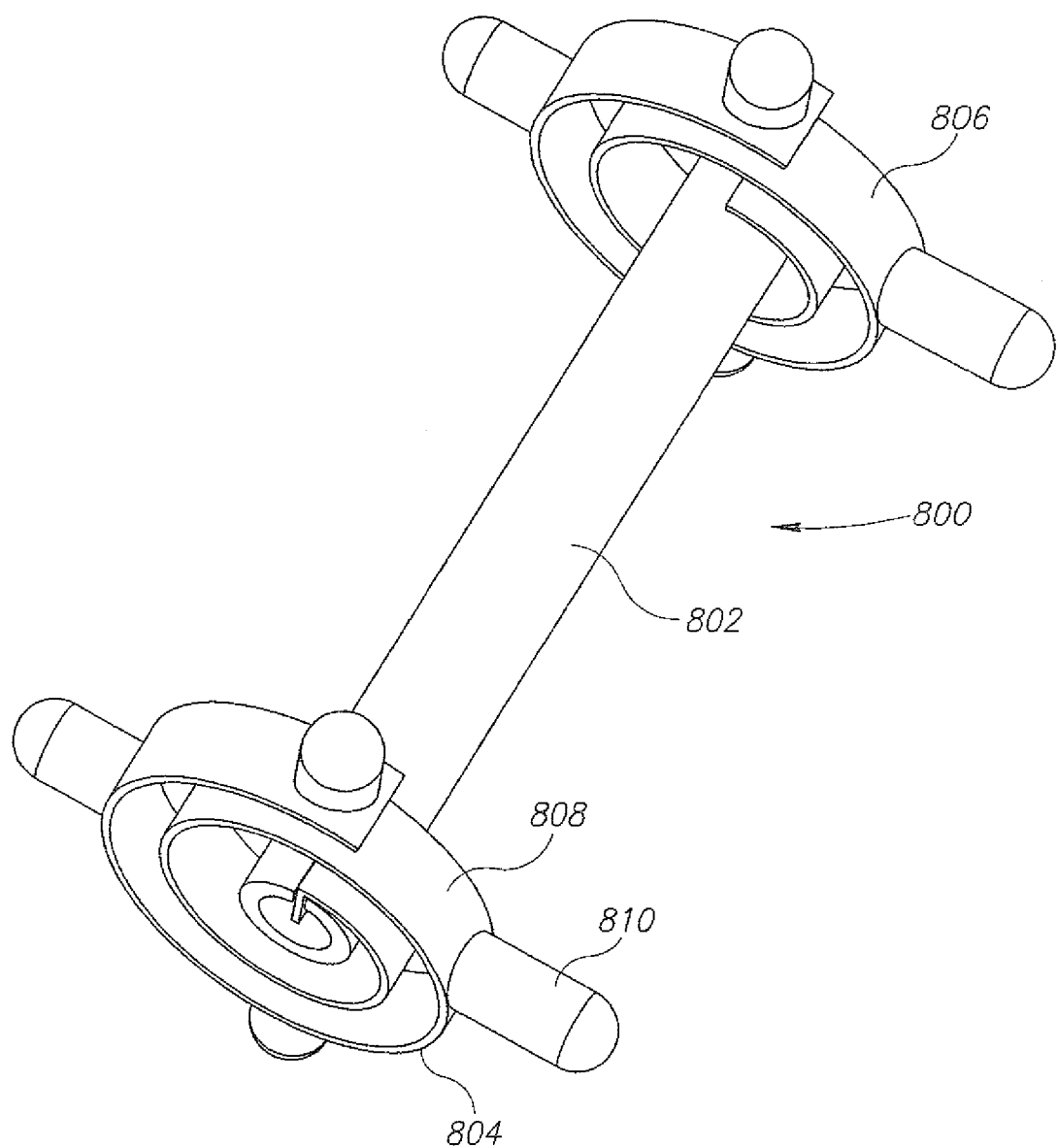
FIG. 8 is a profile view of a connected, double-sided, scrolling incontinence device in accordance with an exemplary embodiment of the invention.

Referring to FIG. 8, a double-sided, scrolling incontinence device 800 is shown, in accordance with an exemplary embodiment of the invention. Device 800 is optionally comprised of a connecting node 802 which is provided with scrolling, spring-like arm sections located on connecting node's 802 proximal and distal ends. A support arm section 804 and an anchor arm 806 section optionally comprise the arm sections provided to connecting node 802. In an exemplary embodiment of the invention, an arm section is comprised of a coiling strip 808 which defines a generally circular profile around connecting node 802, as shown in FIG. 8. Optionally, a coiling strip 808 has protrusions 810 located thereon for providing support and/or anchoring. In some exemplary embodiments of the invention, at least the coiling strip 808 of the arm section is flexible. The flexibility of coiling strip 808 allows for compression of the strip in order to fit device 800 into an applicator. Furthermore, the flexible nature of coiling strip 808 optionally provides enhanced comfort to a patient using device 800 as it tends to fit better to the patient during movement than a rigid device. Optionally, connecting node 802 is flexible. Optionally, protrusions 810 are flexible. Optionally, protrusions 810 are provided in varied lengths, such as described in conjunction with FIGS. 7A-D. Optionally, coiling strips defining larger and/or smaller radius circles are used with incontinence device 800, depending on the needs of the patient.

Exemplary Elasto-Mechanical Incontinence Device

Figure 19C:
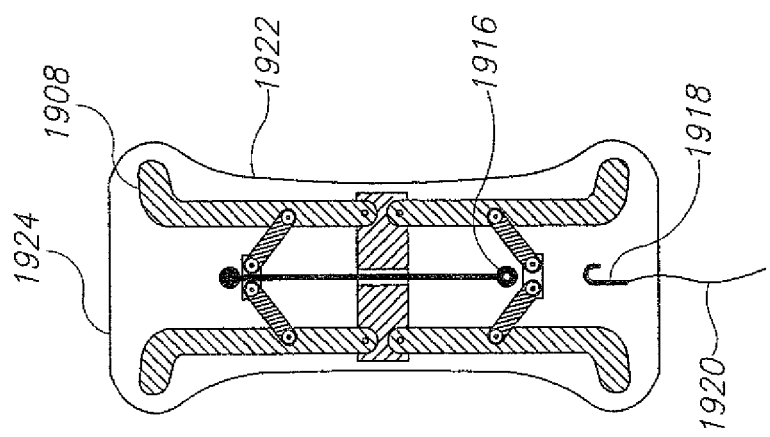
FIG. 19C is a cross-sectional view of an elasto-mechanically expanding incontinence device in a removal configuration, in accordance with an exemplary embodiment of the invention.
Figure 19B:
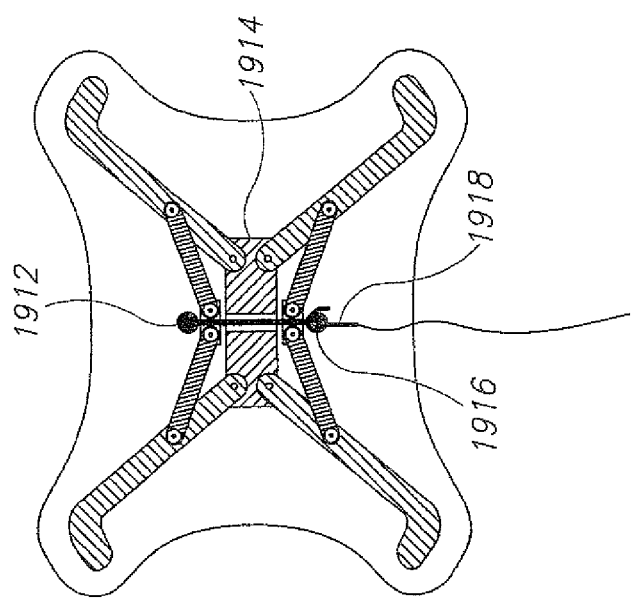
FIG. 19B is a cross-sectional view of an elasto-mechanically expanding incontinence device in a deployed configuration, in accordance with an exemplary embodiment of the invention.
Figure 19A:
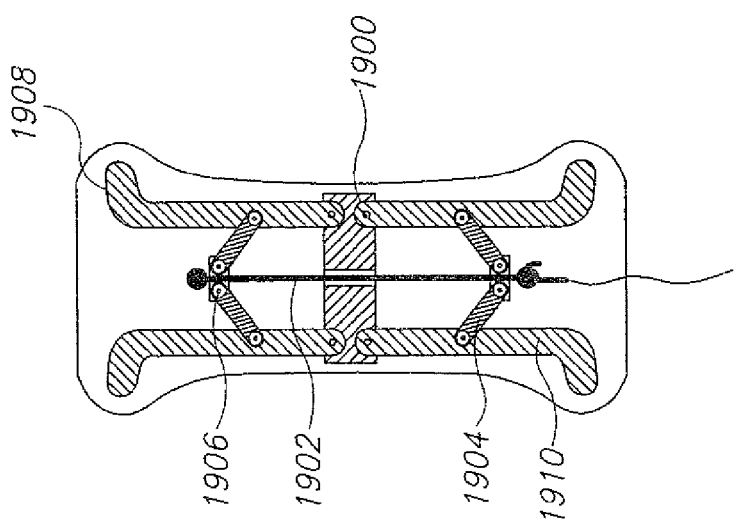
FIG. 19A is a cross-sectional view of an elasto-mechanically expanding incontinence device in a storage configuration, in accordance with an exemplary embodiment of the invention.

Referring to FIGS. 19A-C, an incontinence device 1900 is shown which is provided with an elasto-mechanical operation to achieve radial expansion and/or contraction, in accordance with an exemplary embodiment of the invention. In some exemplary embodiments of the invention, at least one expander 1904 is provided to device 1900 connected to an anchor arm 1908 or a support arm 1910 of the device 1900. An elastic member 1902 is provided to incontinence device 1900 which, in some exemplary embodiments of the invention, selectively causes expanders 1904 to radially expand and/or contract device 1900.

FIG. 19A shows incontinence device 1900 in a storage configuration (for example, while in an applicator), in accordance with an exemplary embodiment of the invention. Expanders 1904 are connected on one end to an expander node 1906 and on the other end to either anchor arm 1908 or support arm 1910, such that both ends of expanders 1904 can pivot with respect to whatever it is attached to. In a storage configuration, elastic member 1902 is stretched, allowing expanders 1904 to pivot, permitting support arms and anchor arms to assume a reduced radial profile.

FIG. 19B shows incontinence device 1900 deployed, in accordance with an exemplary embodiment of the invention. Elastic member 1902, previously stretched during storage, contracts to its nominal state catching the expander nodes with the enlarged ends 1912 of elastic member 1902 and forcing expanders 1904 into an expanded configuration. In an exemplary embodiment of the invention, expanders 1904 push out their respective arms causing device 1900 to expand its radial profile. The arms are connected to a central node 1914 such that they may pivot to assume various operational configurations (e.g. storage, deployed, removal). In an exemplary embodiment of the invention, support section enlarged end 1916 is sized so that it would pass through the expander node but for the safety catch 1918, which is removable as seen in FIG. 19C.

In FIG. 19C, incontinence device 1900 is shown in a removal configuration, in accordance with an exemplary embodiment of the invention. Removal of device 1900 is optionally facilitated by reducing the radial profile of device 1900. In an exemplary embodiment of the invention, reducing the radial profile of device 1900 is achieved by removing safety catch 1918, which nominally prevents support section enlarged end 1916 from passing through the expander node. Once support section enlarged end 1916 passes through the expander node, the expanders for that node are free to collapse the support arms towards a central axis of device 1900, at least in response to pressure exerted on them by the vaginal wall. Optionally, expanders 1904 are at least partially elastic. Optionally, safety catch 1918 is removed by applying force on a removal device 1920 in a direction opposite the user's cervix and towards the vaginal opening. Optionally, security catch 1918 is tied in a looseable knot, which comes undone upon the application of sufficient force away from the cervix. Optionally, security catch 1918 is comprised of a breakaway portion which causes catch 1918 to become unfastened to support section enlarged end 1916 when sufficient force is applied to catch 1918 by removal device 1920. In some exemplary embodiments of the invention, a cover 1924 is provided to incontinence device 1900. Optionally, removal device 1920 is affixed to cover 1924 to aid in removal of device 1900. In such an embodiment, sustained force on removal device 1920 applied away from the user's cervix subsequently causes the reduced profile device 1900 to be pulled out of the user's vagina along with cover 1924.

Exemplary Embodiment of an Incontinence Device Provided With a Tensile Element

Figures 21A, 21B:
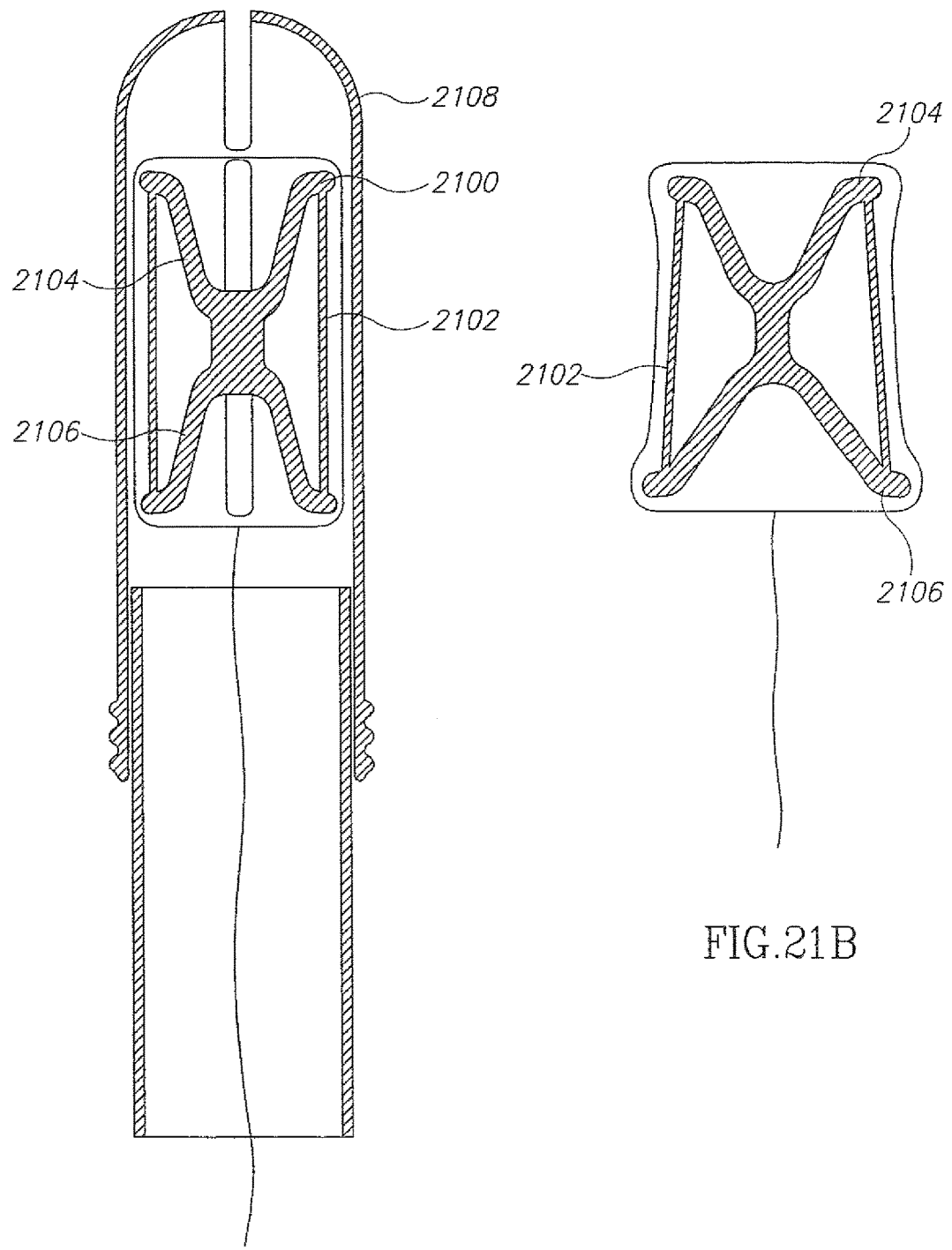
FIG. 21A is a cross-sectional view of an incontinence device provided with dimension setting connectors in a storage configuration, in accordance with an exemplary embodiment of the invention.
FIG. 21B is a cross-sectional view of an incontinence device provided with dimension setting connectors in a deployed configuration, in accordance with an exemplary embodiment of the invention.

Referring to FIG. 21A, an incontinence device 2100 is shown which is provided with at least one tensile element 2102, in accordance with an exemplary embodiment of the invention. In some exemplary embodiments of the invention, at least one tensile element 2102 extends between arms of an anchor section 2104 and corresponding arms of a support section 2106 of incontinence device 2100. Optionally, at least one tensile element 2102 is elastic. In some exemplary embodiments of the invention, at least one tensile element 2102 is stretched prior to deployment and/or while being stored in an applicator 2108 in order to reduce the radial profile of device 2100 and optionally, to provide force for expanding the arms of support section 2106 during deployment.

FIG. 21B shows incontinence device 2100 in a deployed configuration, in accordance with an exemplary embodiment of the invention. In some exemplary embodiments of the invention, at least one tensile element 2102 substantially unstretches upon being deployed, providing a deployment force to support section 2106 and, optionally, anchor section 2104 of incontinence device 2100. Optionally, the flexibility of anchor section 2104 and/or support section 2106 is varied in order to control the response to at least one tensile element 2102. For example, in an embodiment where anchor section 2104 is not expected to display much radial expansion, it would be suitable to decrease the flexibility of anchor section 2104 so it would not respond to at least one tensile element 2102 as it would have if it were more flexible. It should be understood that at least one tensile element 2102 can be used in conjunction with any of the incontinence devices described herein in order to assist with incontinence device deployment.

Exemplary Lubricating Applicator Embodiments

In some exemplary embodiments of the invention, lubrication is provided to the applicator used for inserting a device into the vagina. Lubrication of the applicator eases its insertion and/or removal from the vagina and/or enhances the comfort to the user. FIGS. 9A-B, 10A-B and 24 depict exemplary embodiments of lubricating applicators.

Figure 9A:
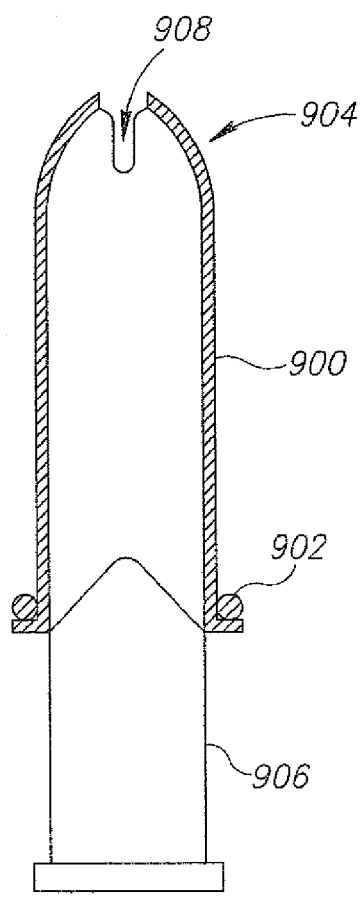
FIG. 9A is a cross sectional view of an applicator with a lubricating ring in accordance with an exemplary embodiment of the invention.

FIG. 9A is a cross sectional view of an applicator 900 with a lubricating ring 902, in accordance with an exemplary embodiment of the invention. Applicator 900 serves for insertion of an incontinence device into the vagina of a patient. Insertion is accomplished using this applicator in a similar fashion to inserting a regular menstrual tampon. In an exemplary embodiment of the invention, the incontinence device is kept within the distal end 904 of applicator 900 that is inserted into the vagina. When pushing on a plunger 906 located at the proximal end of applicator 900, the incontinence device is pushed through the exit 908, allowing for utilization of the incontinence device once the applicator 900 is removed from the vagina. It should be noted that in an exemplary embodiment of the invention, the exit 908 remains closed until plunger 906 is pushed and the incontinence device is forced out of applicator 900. Optionally, exit 908 is comprised of a plurality of sections.

While introducing an incontinence device into the vagina with the applicator 900, insertion is optionally facilitated by lubricating applicator 900. In an exemplary embodiment of the invention, lubricating ring 902 is provided to lubricate the external surface of applicator 900. Optionally, ring 902 is slidable over the length of applicator in order to provide lubrication at least over the area to be inserted into the vagina. Optionally, lubrication is directed towards at least the distal end of the applicator near the exit. Optionally, ring 902 is hollow. Materials located within ring 902 are optionally squeezed out from ring 902 via a plurality of small holes (not shown) located on ring 902. In an exemplary embodiment of the invention, ring 902 is filled with lubricant. Optionally, ring 902 is filled with a pharmaceutical. Optionally the small holes face applicator 900 such that when the materials come out of ring 902 they are primarily deposited on applicator 900. Optionally, ring 902 is constructed of a flexible material, such as silicone. In an exemplary embodiment of the invention, ring 902 is pulled along applicator 900 while applying at least slight pressure to ring 902 in order to eject the materials within through the plurality of holes. As ring 902 moves along applicator 900, the material is deposited on applicator 900 in accordance with the speed of movement of ring 902, pressure on ring 902, amount of material within ring 902 and/or other variables. Ring 902 is optionally removed from applicator 900 before applicator 900 is used to deploy a device. Optionally, ring 902 remains on applicator 900 during device deployment and then is disposed of, along with applicator 900.

Figure 9B:
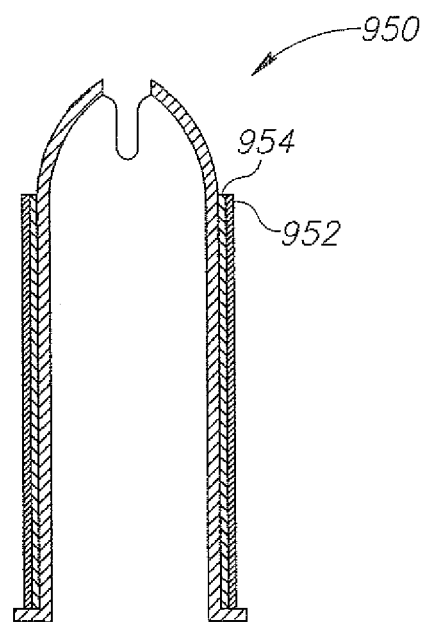
FIG. 9B is a cross sectional view of an applicator with a removable cover in accordance with an exemplary embodiment of the invention.

Referring to FIG. 9B, a cross sectional view of an applicator 950 with a removable cover 952 is shown, in accordance with an exemplary embodiment of the invention. Applicator 950 is optionally circumferentially enclosed by a removable cover 952. In an exemplary embodiment of the invention, removable cover 952 seals between it and applicator 950 a layer 954 of a material such as a lubricant and/or a pharmaceutical. Optionally, removable cover 952 is manufactured from a substance, such as polymers, nylon or aluminum foil, that preserves the lubricant and/or pharmaceutical material layer 954 for an extended period of time. Prior to insertion of applicator 950 into the patient's vagina, removable cover 952 is removed from applicator 950 to reveal material layer 954. Optionally, removable cover 952 and/or material layer 954 cover only a portion of applicator 950.

Figure 10A:
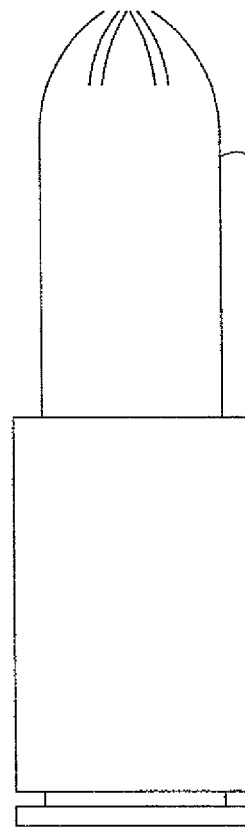
FIG. 10A is side view of an applicator with a lubricating sleeve in accordance with an exemplary embodiment of the invention.
Figure 10B:
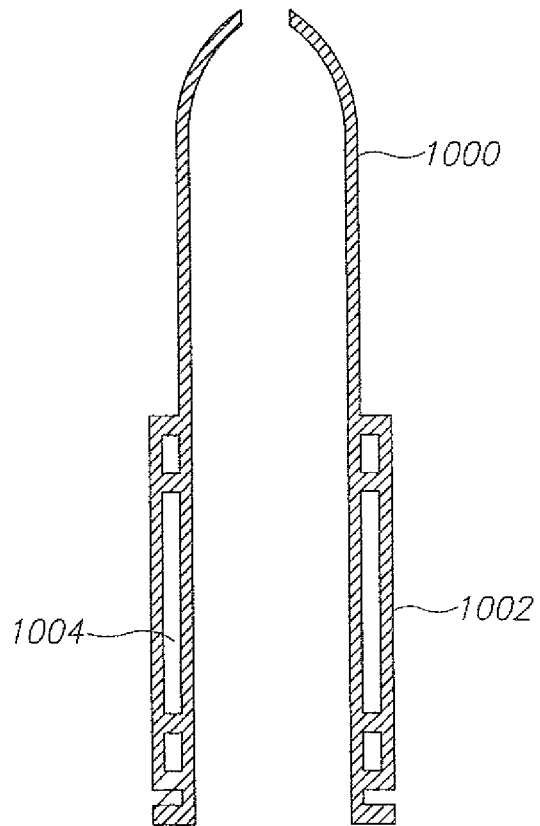
FIG. 10B is a cross sectional view of an applicator with a lubricating sleeve in accordance with an exemplary embodiment of the invention.

FIG. 10A illustrates a side view of an applicator 1000 with a lubricating sleeve 1002 in accordance with an exemplary embodiment of the invention. Similar to the lubricating ring embodiment described with respect to FIG. 9A, lubricating sleeve 1002 is used to ease insertion of applicator 1000 into a patient's vagina for incontinence device deployment by spreading a lubricant onto the exterior surface of applicator 1000. Optionally, lubricating sleeve 1002 is used to dispense a pharmaceutical onto applicator 1000. A cross sectional view of applicator 1000 is shown in FIG. 10B. In an exemplary embodiment of the invention, lubricating sleeve 1002 is provided with a reservoir 1004 which is used for storage of the lubricant and/or a pharmaceutical. Lubricating sleeve 1002 is optionally provided with a plurality of outlets whereby upon the release of the lubricant through the outlets, at least a portion of applicator 1000 receives coverage. In an exemplary embodiment of the invention, lubricating sleeve 1002 is moved along the surface of applicator 1000 to deposit lubricant. Optionally, lubricating sleeve 1002 is removed from applicator 1000 by sliding it over the distal end of the applicator prior to insertion of applicator 1000 into the patient's vagina.

Figure 24:
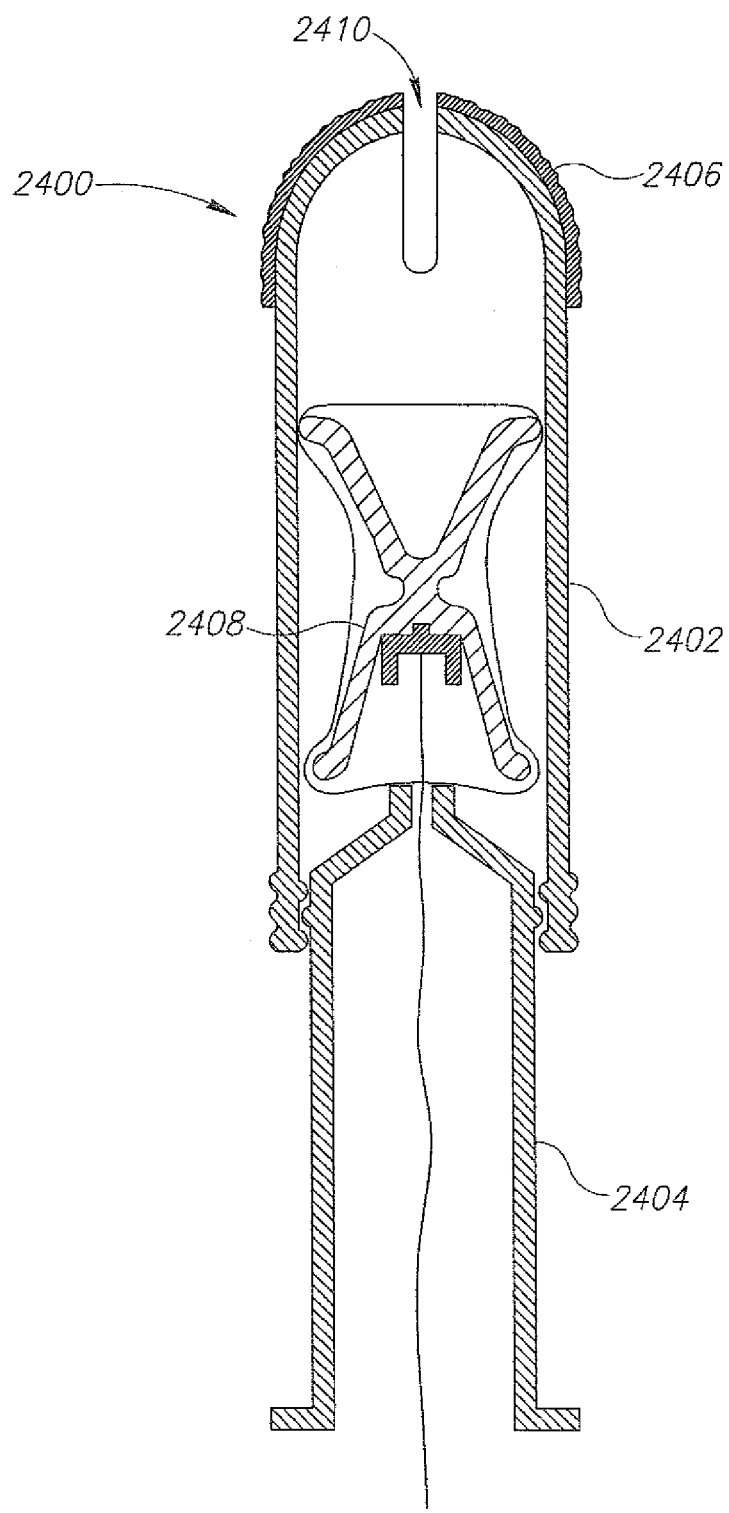
FIG. 24 is a cross-sectional view of an applicator with a lubricating layer, in accordance with an exemplary embodiment of the invention; and, FIG. 25A is a cross-sectional view of a slotted applicator with a sliding sleeve in a distal position in accordance with an exemplary embodiment of the invention.

Referring to FIG. 24, a lubricating applicator 2400 is shown in accordance with an exemplary embodiment of the invention. Applicator 2400 operates in a similar fashion to deploy an incontinence device 2408 as other applicators described herein, by applying pressure on a plunger 2404 to expel device 2408 from an enclosure 2402 and into a vagina, in an embodiment of the invention. A lubricating layer 2406 is applied to applicator 2400, optionally towards a proximal end 2410 of applicator to ease insertion of applicator 2400 into a user's vagina. In some exemplary embodiments of the invention, lubricating layer 2406 is comprised of a lubricant which is highly viscous. The highly viscous lubricant is applied at the proximal end of applicator 2400 at the time of manufacture and remains in place during storage. At the time of use, the viscous lubricating layer 2406 eases insertion of applicator 2400 into the user's vagina. Optionally, the lubricating layer 2406 is comprised of silicone oil. Optionally, the lubricating layer 2406 is comprised of glycerin. Optionally, the lubricating layer 2406 is comprised of a petroleum jelly. Optionally, lubricating layer 2406 is comprised of a viscous, water based material. Optionally, viscous lubricating layer 2406 is applied to any of the applicators described herein.

Exemplary Applicator Embodiments for Improving Storage Conditions of Incontinence Devices In some exemplary embodiments of the invention, methods and apparatuses for storing and applying incontinence devices are provided. FIGS. 11A-B, 12A-D and 25A-C depict exemplary embodiments which allow for at least a portion of the device to remain in a substantially uncompressed condition during storage. It is believed that reduction of the storage stresses on at least a portion of the device enhances performance and/or shelf life of the device.

Figure 11A:
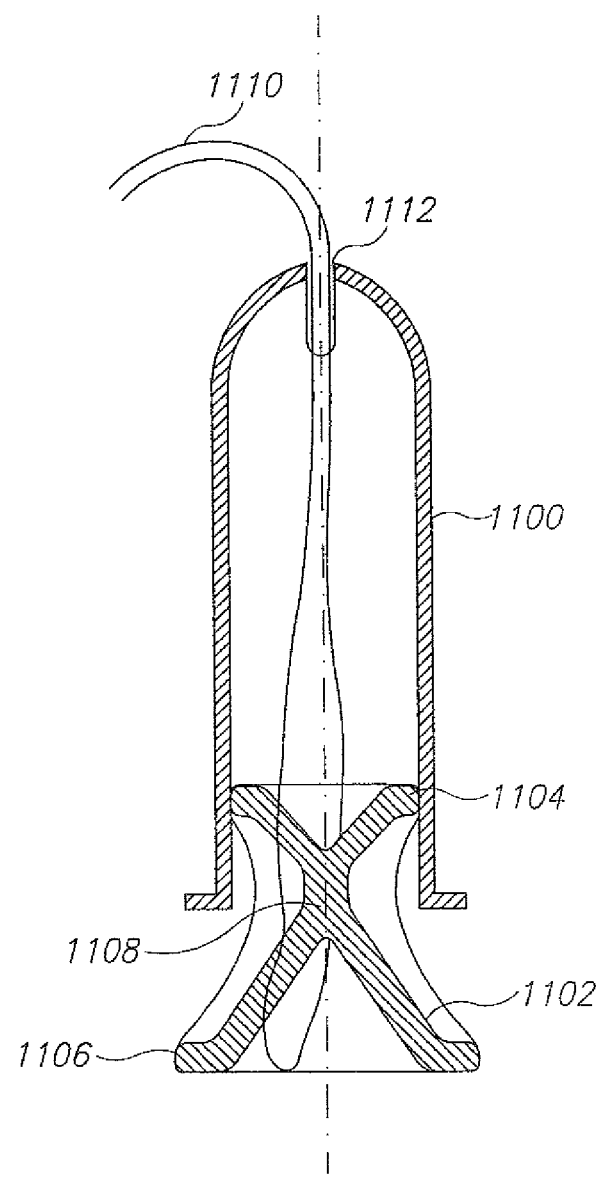
FIG. 11A is a cross sectional view of an applicator and a loosely loaded incontinence device in accordance with an exemplary embodiment of the invention.

Referring to FIG. 11A, a cross sectional view of an applicator 1100 and a loosely loaded incontinence device 1102 is shown, in accordance with an exemplary embodiment of the invention. Optionally, incontinence device 1102 is any of those described herein or radially expandable and known in the art. Typically, storage of an at least partially elastic device in a compressed state reduces the efficacy of the device somewhat. In an exemplary embodiment of the invention, an incontinence device, such as some of those described herein, is only loosely loaded into applicator 1100 in order to avoid degradation of incontinence device 1102 as a result of compression during storage within applicator 1100. Optionally, loosely loaded comprises loading only an anchor section 1104 of incontinence device 1102 into applicator 1100, while support section 1106 and optionally central node 1108 remain outside of applicator 1100. In an exemplary embodiment of the invention, a loading device 1110 is provided which is connected to incontinence device 1102 and which extends through the applicator 1100 and out via an exit 1112 located at a distal end of applicator 1100. Optionally, loading device 1110 is removably connected to incontinence device 1102 so that after loading device 1102 into applicator 1100, loading device 1110 is removed from applicator 1100. Optionally, loading device 1110 is string-like and is looped around incontinence device 1102 such that the two ends of the string are accessible at exit 1112, as depicted in FIG. 11A.

Loading incontinence device 1102 into applicator is accomplished by pulling on loading device 1110 towards distal end of applicator which in turn pulls incontinence device 1102 into applicator 1100. Optionally, pulling is performed with clean hands to maintain the sterility of applicator. Optionally, a peel off layer is provided to applicator which is removed after device 1102 is loaded into applicator 1100. In the embodiment depicted in FIG. 11A, both ends of loading device 1110 are pulled simultaneously to achieve loading. Removal of loading device 1110 from applicator 1100 is optionally accomplished by pulling on one end of loading device 1110 available at exit 1112 until the entire loading device 1110 is pulled out of applicator 1100. In an exemplary embodiment of the invention, a plunger (not shown) is applied to the proximal end of applicator 1100 (where incontinence device 1102 was loaded) in order to deploy incontinence device 1102 into a patient's vagina. Optionally, the plunger is provided separately from applicator 1150, shown in FIG. 11B, and is used only when deployment of incontinence device 1102 is desired.

Figure 11B:
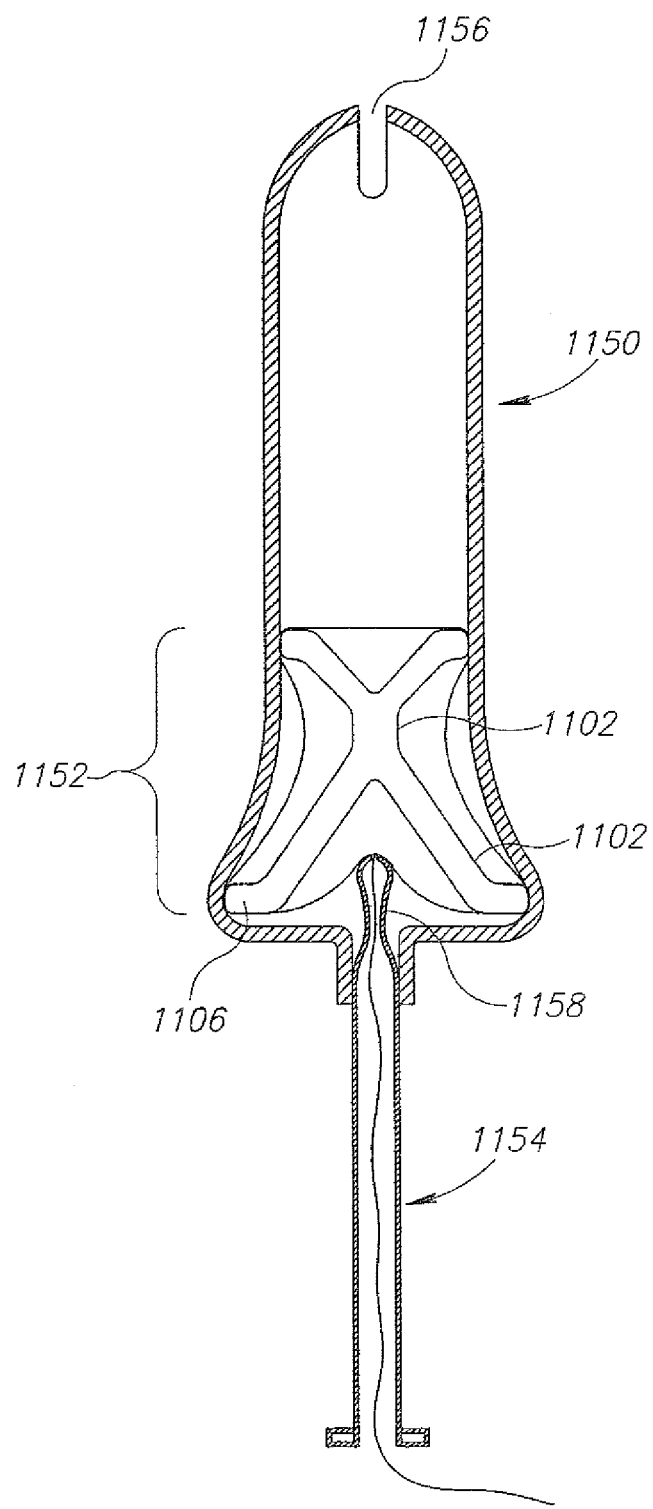
FIG. 11B is a cross sectional view of a flared proximal end applicator loaded with an incontinence device in accordance with an exemplary embodiment of the invention.

FIG. 11B shows a cross sectional view of a flared proximal end applicator 1150 which is loaded with an incontinence device 1102, in accordance with an exemplary embodiment of the invention. Applicator 1150 is provided with a flared section 1152 towards its proximal end. As in the embodiment described with respect to FIG. 11A, incontinence device 1102 is only partially loaded into a narrow portion of applicator 1150, whereas the remainder of incontinence device 1102 is positioned within flared section 1152. Optionally, flared section 1152 is sized to allow full expansion of the support section 1106 of incontinence device 1102. In an embodiment of the invention, flared section 1152 is provided with flared segments in number and size to accommodate each arm of support section 1106. Optionally, flared section is at least partially conical shaped, and not provided with specific flared segments, but a generally flared, conical shape for accommodation of device 1102 irrespective of rotational orientation. Deployment of incontinence device 1102 is accomplished by using a plunger 1154 to urge incontinence device 1102 towards an exit 1156 located at the distal end of applicator 1150. Optionally, plunger 1154 is provided with a shaped head 1158 in order to stimulate convergence of support section 1106 towards the central axis of device 1102. Optionally, plunger 1154 is provided separately from applicator 1150, and is used only when deployment of incontinence device 1102 is desired.

Optionally, flared section 1152 begins its flare at the proper place on the applicator to indicate correct insertion depth. In an embodiment of the invention, applicator 1150 is substantially open on the proximal end (not substantially closed as shown in FIG. 11B). In some embodiments of the invention, the open proximal end is provided with a lip, which corresponds to a lip on plunger 1154, designed to prevent plunger 1154 from dislocating from applicator 1150.

Figure 12A:
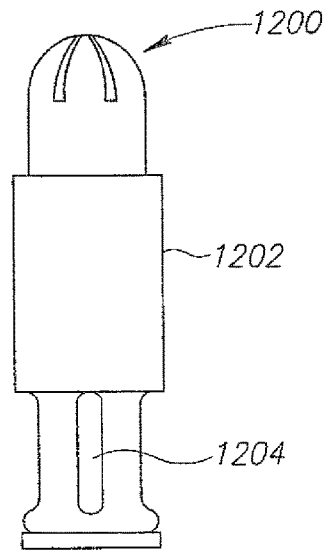
FIG. 12A is a side view of a slotted applicator with a sliding sleeve in a distal position in accordance with an exemplary embodiment of the invention.
Figure 12B:
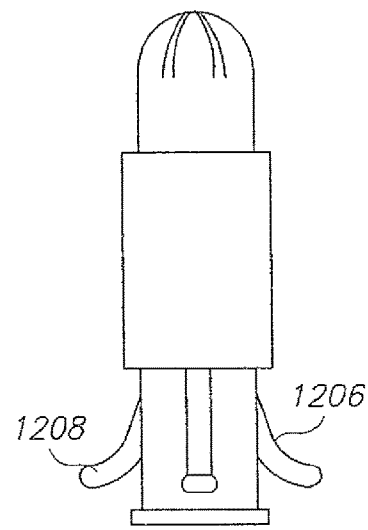
FIG. 12B is a side view of a slotted applicator with a sliding sleeve loaded with an incontinence device with arms protruding out of the applicator slots in accordance with an exemplary embodiment of the invention.

Referring to FIG. 12A, a side view of a slotted applicator 1200 with a sliding sleeve 1202 is shown, in accordance with an exemplary embodiment of the invention. Sliding sleeve 1202 is optionally located on the external surface of applicator 1200 and is capable of movement up and/or down the length of applicator 1200. It can be seen that applicator 1200 is provided with a plurality of slots 1204 in an exemplary embodiment of the invention. Optionally, slots 1204 correspond in shape and/or number to support arms of an incontinence device. In an exemplary embodiment of the invention, the shelf life of an incontinence device is lengthened by avoiding storage of the device in a compressed configuration within an applicator. Instead, the support arms of an incontinence device 1206 optionally project out of slots 1204 prior to deployment in a patient's vagina, as depicted in FIG. 12B.

Figure 12C:
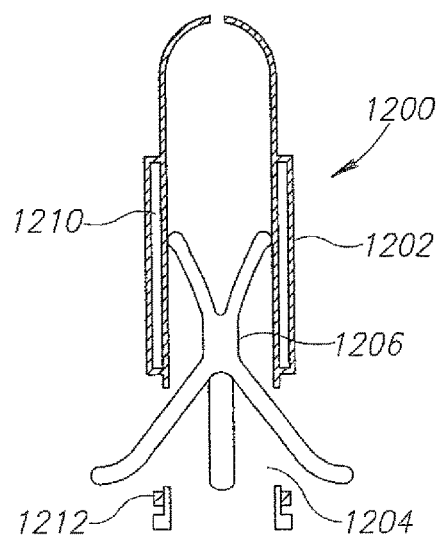
FIG. 12C is a cross sectional view of a slotted applicator with a sliding sleeve loaded with an incontinence device in accordance with an exemplary embodiment of the invention.

FIG. 12C is a cross sectional view of slotted applicator 1200 with sliding sleeve 1202 loaded with incontinence device 1206, in accordance with an exemplary embodiment of the invention. From this perspective, it can be seen that incontinence device 1206, while within applicator 1200, is partially located outside of applicator 1200 and avoids compression on the support arms 1208 during storage. In some exemplary embodiments of the invention, sliding sleeve 1202 is provided with a reservoir 1210, from which substances may be deposited onto surface of applicator 1200. Optionally, reservoir 1210 is provided with a plurality of openings between itself and applicator 1200 to deposit substances stored within onto surface of applicator 1200. Optionally, a lubricant is a substance which is stored in reservoir 1210. Optionally, a pharmaceutical is a substance stored within reservoir 1210. Substances in reservoir 1210 are optionally deposited on applicator 1200 by moving sliding sleeve 1202 up and/or down the length of applicator's 1200 surface. In some exemplary embodiments of the invention, lubricant is deposited on applicator 1200 from reservoir 1210 prior to insertion of applicator 1200 in a vagina, in order to ease insertion of applicator 1200 into vagina and the deployment of incontinence device 1206 stored within.

Figure 12D:
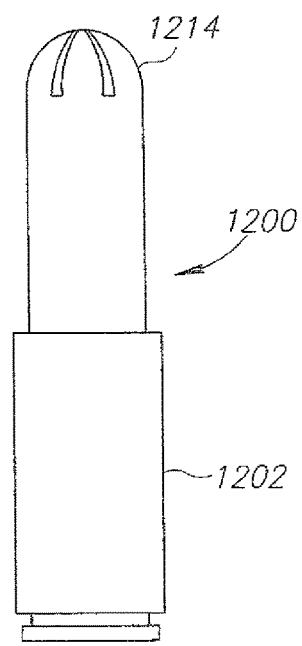
FIG. 12D is a side view of a slotted applicator with a sliding sleeve wherein a sliding sleeve is in a proximal position in accordance with an exemplary embodiment of the invention.

Referring to FIG. 12D, a side view of slotted applicator 1200 with sliding sleeve 1202 is shown wherein sliding sleeve 1202 is in deployment position, in accordance with an exemplary embodiment of the invention. Prior to incontinence device 1206 deployment, sliding sleeve 1202 is slid along applicator 1200 to its proximal end (closest to the vaginal opening when inserted in the vagina) where sliding sleeve 1202 becomes locked into deployment position. The motion of sliding 1202 sleeve pushes arms 1208 into slots 1204 readying them for deployment. Once sliding sleeve 1202 reaches deployment position, it is held in place by a dent 1212 to prevent it from sliding back to the distal end 1214 of applicator 1200. When sliding sleeve 1202 is in deployment position, arms 1208 are forcefully converged towards the central axis of incontinence device 1206 such that the device is deployable from applicator 1200. In some exemplary embodiments of the invention, the sleeve does not rely on sliding for movement but instead screws up and down applicator 1200 along threads located on external surface of applicator 1200.

Figures 25A, 25B:
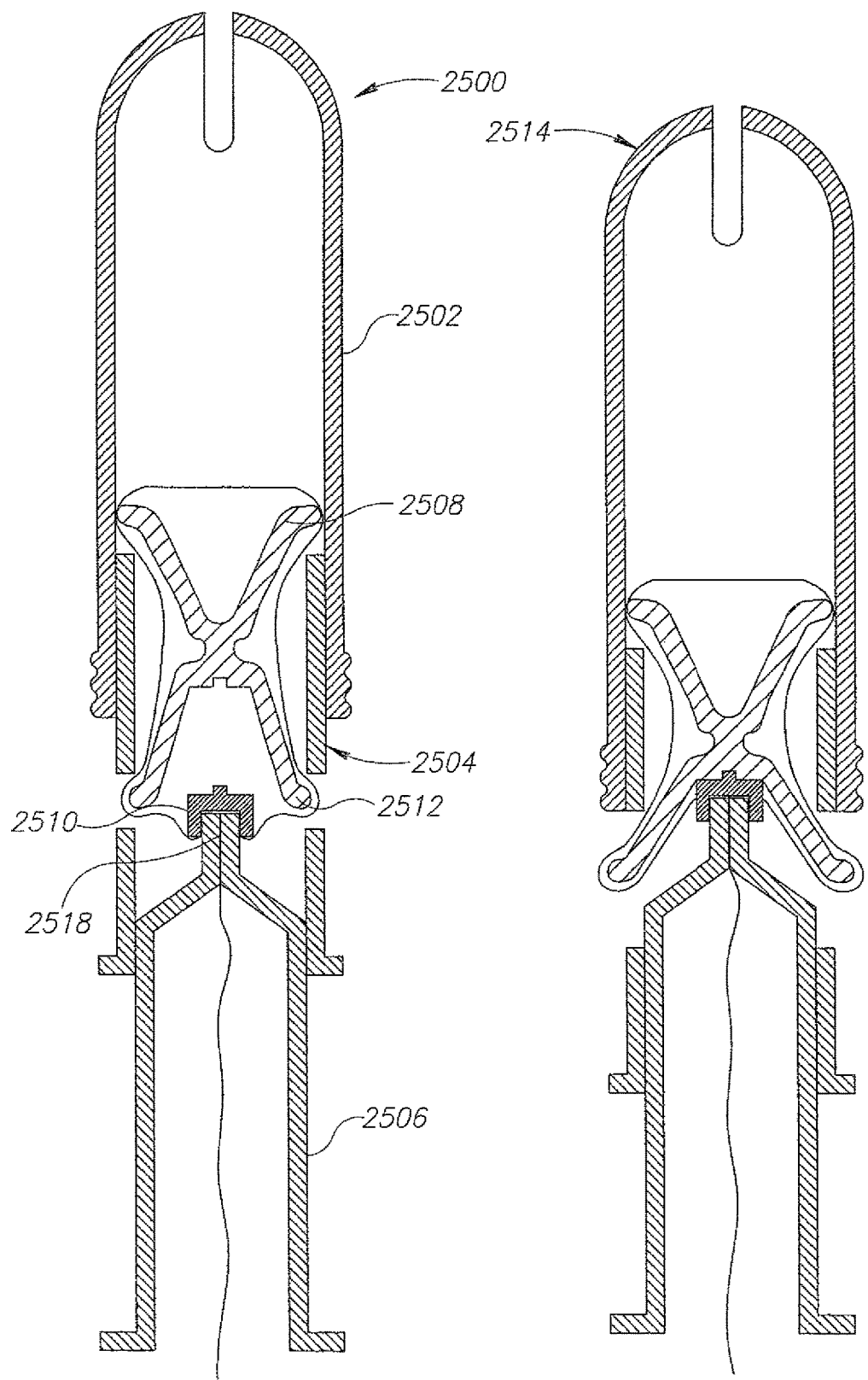
FIG. 25B is a cross-sectional view of a slotted applicator with a sliding sleeve in a primed position in accordance with an exemplary embodiment of the invention.

FIG. 25A depicts an applicator 2500 which is comprised of a three part slotted applicator designed to reduce stress on an incontinence device 2508 located therein during storage, in accordance with an exemplary embodiment of the invention. Applicator 2500 includes an enclosure 2502, a slotted section 2504, and a plunger 2506 in an embodiment of the invention. Slotted section 2504 is substantially cylindrical and is provided with slots (similar to the slots of applicator 1200) which correspond to the number and approximate size of support arms 2512 of device 2508. While device 2508 is in storage, support arms 2512 jut out of the slots provided to slotted section 2504, thereby reducing compressive stress forces on device 2508 and improving shelf life and performance of device 2508. Optionally, support arms 2512 are protected by a bag or cover while they are exposed.

In an exemplary embodiment of the invention, slotted section 2504 is coaxially mounted on the inner circumference of enclosure 2502 such that the slots remain exposed, thereby allowing support arms 2512 of a device 2508 located therein to jut out. Plunger 2506 is mounted coaxially on the inner circumference of slotted section 2504, optionally with a protrusion 2518 in contact with an insert 2510, insert 2510 being used to cause support arm 2512 expansion for treatment rendering deployment. In an embodiment of the invention, plunger 2506 is slidable within slotted section 2504 and slotted section 2504 is slidable within enclosure 2502.

In an embodiment of the invention, slotted section 2504 fits friction fits within enclosure 2502 such that it requires more force on plunger 2506 to cause slotted section 2504 to slide within enclosure 2502 than it does to attach insert 2510 to device 2508. In operation, depicted in FIG. 25B, plunger is moved by the user towards a distal end 2514 of enclosure 2502 depositing insert 2510 in device 2508, but without substantially moving slotted section 2504. Once insert 2510 is deposited, continued force on plunger 2506 towards distal end 2514 causes slotted section 2504 to slide towards distal end 2514 of enclosure 2502. It should be noted that although insert 2510 is rendering radial expansion force to support arms 2512 while device 2508 is still within applicator 2500, the flexible nature of device 2508, and optionally insert 2510, allows for temporary compression of device 2508 prior to expulsion from applicator 2500 and deployment within the user's vagina. In an exemplary embodiment of the invention, device 2508 is deployed shortly after insert 2510 is deposited into device 2508.

Figure 25C:
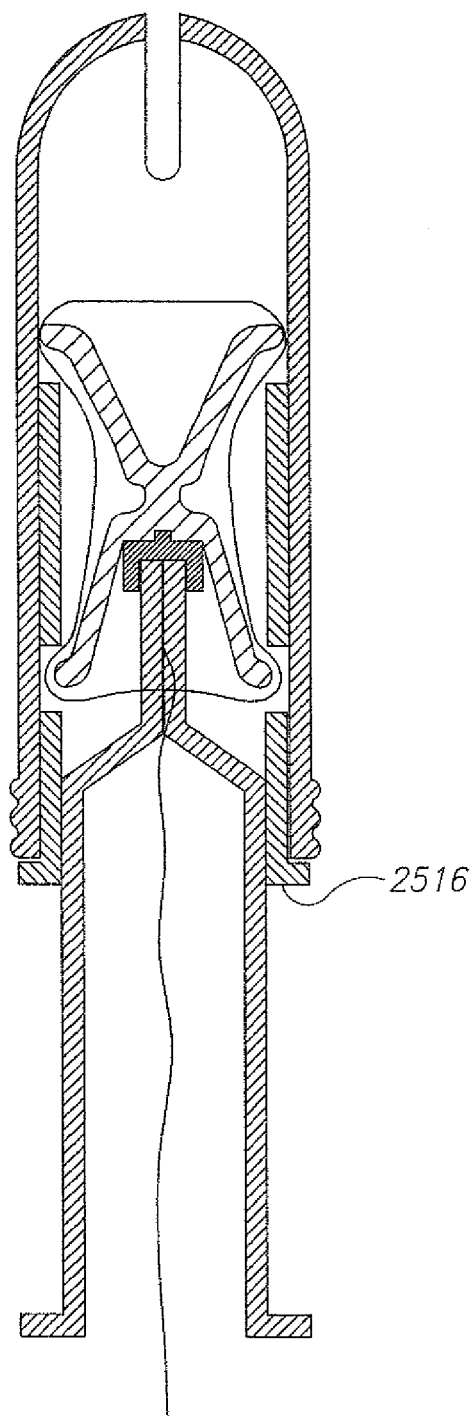
FIG. 25C is a cross-sectional view of a slotted applicator with a sliding sleeve in an imminent deployment position in accordance with an exemplary embodiment of the invention.

As shown in FIG. 25C, slotted section 2504 continues movement within enclosure 2502 until a circumferential ring 2516 around the distal end of slotted section 2504 abuts enclosure 2502. Optionally, at least one protrusion is used in lieu of circumferential ring 2516. Continued application of force on plunger 2506 ejects device 2508 from applicator 2500 and the force of the insert 2510 on the support arms 2512 causes them to radially expand in place in the user's vagina, thereby rendering urethral support to the user. Optionally, the support is mid-urethral.

Exemplary Collapsible Applicator Embodiment

Figures 26A, 26B:
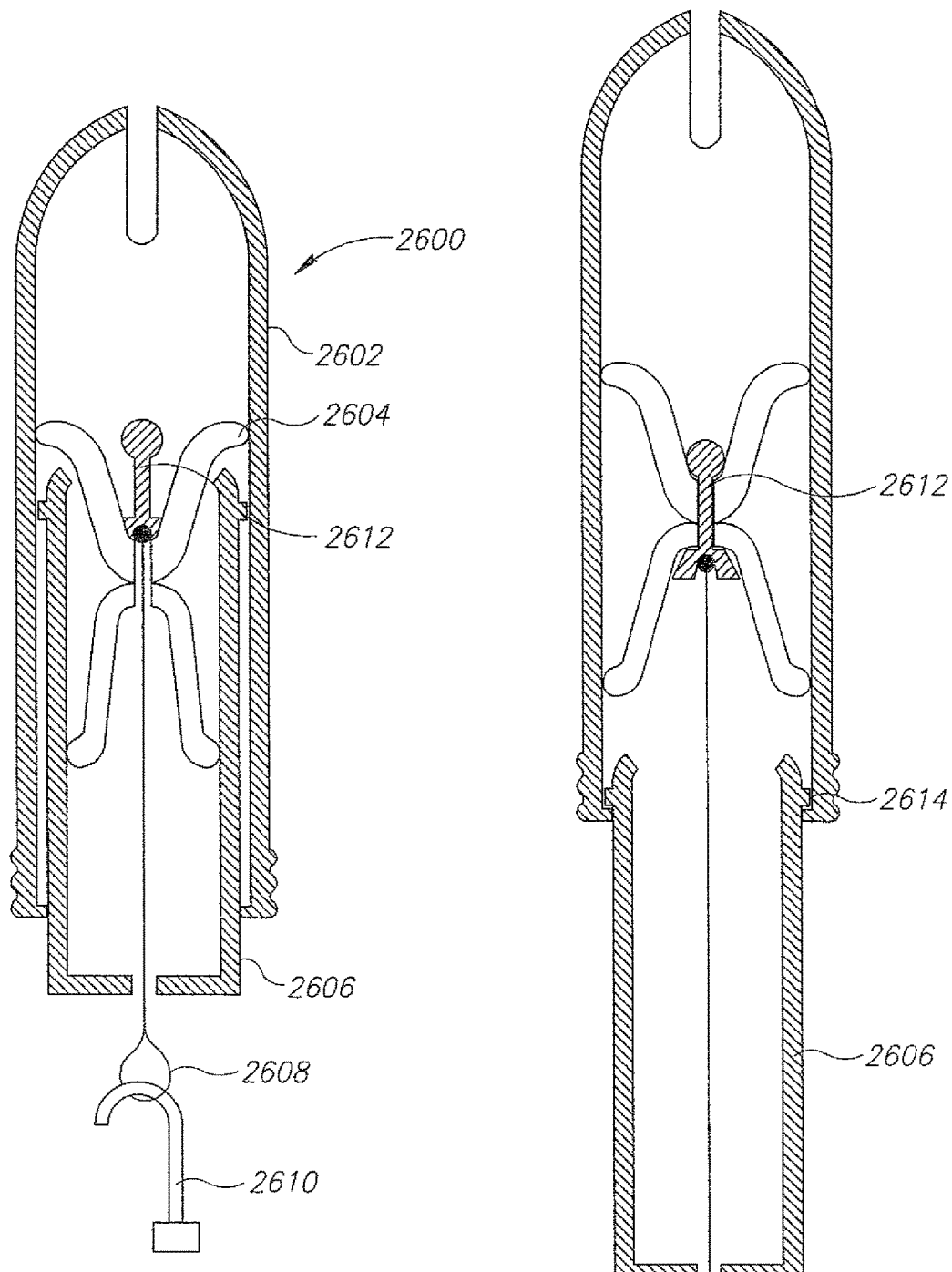
FIG. 26A is a cross-sectional view of a collapsible applicator in a collapsed configuration, in accordance with an exemplary embodiment of the invention.
FIG. 26B is a cross-sectional view of a collapsible applicator in an expanded configuration, in accordance with an exemplary embodiment of the invention.

Referring to FIG. 26A, an applicator 2600 is shown which in some embodiments is capable of assuming an axially collapsed configuration prior to use. In addition, applicator 2600 prepares an incontinence device 2604 for use during deployment, in some embodiments of the invention. A collapsible applicator could be desirable for more convenient storage (takes up less space), for example. An enclosure 2602 is provided to applicator 2600 which contains incontinence device 2604 (device 2604 shown is that of FIGS. 27A-B) therein and while in a collapsed configuration, a large portion of a plunger 2606. In an exemplary embodiment of the invention, an insert 2612 used to help deploy device 2604 is attached to an activation/removal device 2608, for reasons described below. Optionally, activation/removal device 2608 is removably fastened to applicator 2600 by a latch 2610.

In an exemplary embodiment of the invention, prior to use of applicator 2600 to deploy incontinence device 2604, plunger 2606 is pulled downwards to a configuration shown in FIG. 26B. Interfacing ledges 2614 are provided on plunger 2606 and enclosure 2602 to prevent plunger 2606 from dislodging from applicator 2600, in some embodiments of the invention. The pulling action on plunger 2606 causes insert 2612 to pass partially through device 2604 since insert 2612 is attached to activation/removal device 2608 and activation/removal device 2608 is fastened to plunger 2606 by latch 2610. An enlarged distal end of insert 2612 prevents insert 2604 from passing completely through device 2604. The proximal end of insert 2612 is adapted to cause radial expansion of support arms of device 2604, particularly upon deployment of device 2604 out of applicator 2600 and as described with reference to FIGS. 27A-B. In an exemplary embodiment of the invention, latch 2610 is removed from activation/removal device 2608 to enable deployment of device 2604 from applicator 2600. Deployment is optionally effectuated by advancing plunger 2606 towards distal end of applicator 2600 and pushing device 2604 out of applicator.

An Exemplary Plunger

Figure 13:
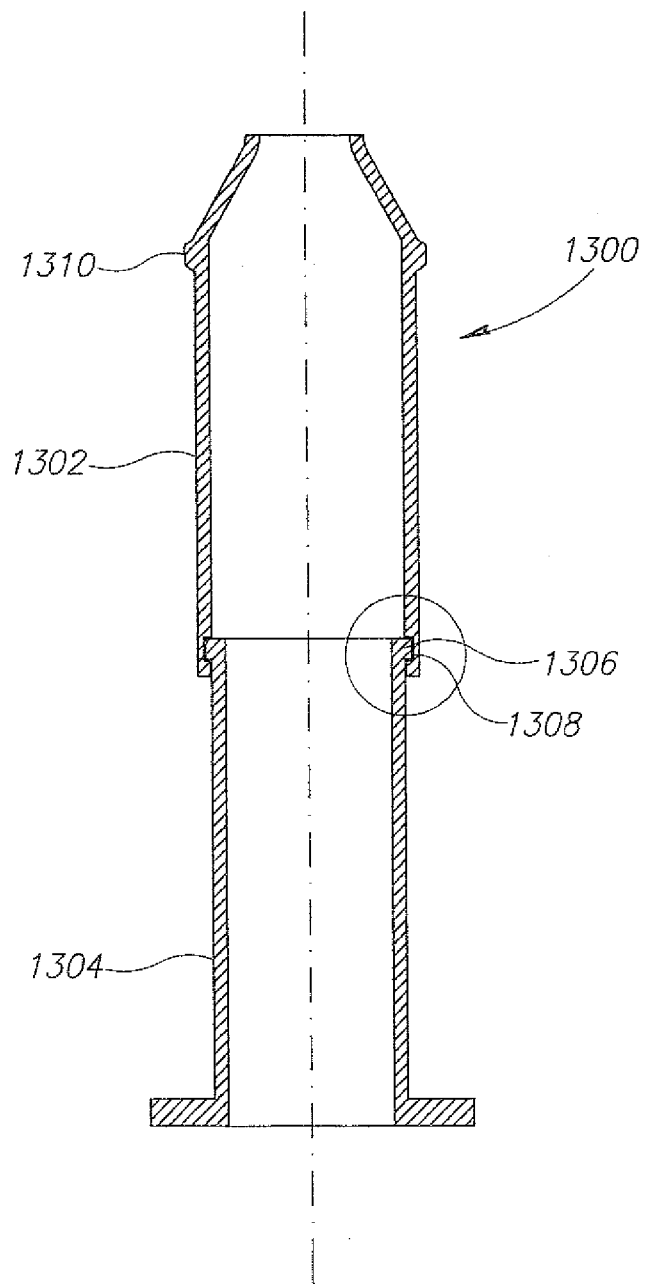
FIG. 13 is a cross sectional view of a telescoping plunger in accordance with an exemplary embodiment of the invention.

FIG. 13 is a cross sectional view of a telescoping plunger 1300, in accordance with an exemplary embodiment of the invention. In some situations, it is desirable to minimize the size of the overall incontinence device package, which generally comprises an applicator, an incontinence device and/or a plunger, in some exemplary embodiments of the invention. The plunger, for example, is long enough to expel an incontinence device from an applicator but also has enough length that it can be manually operated by the patient. In an exemplary embodiment of the invention, the plunger is reduced in size during storage by providing telescoping plunger 1300. In order to shorten the device package without changing dimensions of the applicator, the plunger is optionally supplied in a "closed" or folded position which is expanded for deployment of an incontinence device. In an exemplary embodiment of the invention, telescoping plunger 1300 is provided with two parts, one inside the other. The outer part 1302 of plunger 1300 is partially held inside the body of the applicator as with a non-telescoping plunger while the inner part 1304 of plunger 1300 is positioned at least partially within outer part 1302.

Deployment of plunger 1300 in an exemplary embodiment of the invention involves holding inner part 1304 and pulling it away from outer part 1302 into an "open" position. Continued pulling of inner part 1304 away from outer part 1302 results in inner part 1304 locking into outer part 1302 via an insert 1306 located on inner part 1304 which fits into a recess 1308 adapted to receive and/or interlock with insert 1306 on outer part 1302.

Plunger 1300 is optionally fitted with a ring 1310 which when inserted into an applicator provides at least slight friction between plunger 1300 and the applicator during relative movement between the two and also to prevent plunger from freely falling out of the applicator. Optionally, ring 1310 is comprised of rubber. Optionally, ring is comprised of a polymer based substance. Optionally, ring 1310 is flexible. In some exemplary embodiments of the invention, an applicator is provided with a lip at its proximal opening where plunger is to be inserted. This lip is adapted to resist allowing passage of plunger 1300 and ring 1310 without at least some modicum of force supplied by the person inserting plunger 1300 into the applicator. In an exemplary embodiment of the invention, once plunger 1300 is inside the applicator, this lip resists movement of plunger 1300 back out of the applicator, preventing inadvertent dislodgment of plunger from applicator.

Additional Exemplary Embodiments

It should be noted that a circular ring (not shown in any figures), but previously described in PCT/IL2005/000304, which is herein incorporated by reference, may be located on any applicator in order to mark the proper depth of insertion of the applicator into the vagina. Optionally, the ring can be provided with selectable positions corresponding to different sized women, for personalization.

Furthermore, any of the incontinence devices described herein can be used in conjunction with a cover. In an exemplary embodiment of the invention, a cover is made of a flexible, smooth mesh material. Optionally, the cover is porous. Optionally, the cover is designed as small sack which encapsulates an incontinence device, which acts as an internal support structure for the cover. Use of the cover can potentially provide one or more benefits in using the device. For example, the cover optionally reduces friction between the applicator and the device upon insertion. In addition, the cover optionally reduces friction between the vagina and the device during insertion and/or removal. In some embodiments of the invention, the mesh of the cover, being stretched between the arms of the device, serves as a sling-like support for the urethra. In a woman who leaks urine during a stressful event (when abdominal pressure rises during coughing, sneezing, etc.), the urethra sags down but meets the cover in its mid part. This causes an elevation of the intra urethral pressure with resultant urinary continence. Optionally, the cover provides support to the urethra. In an exemplary embodiment of the invention, the device does not put pressure against the urethra or the bladder neck, but only provides support when there is a rise in abdominal pressure, as described above. Optionally, the device applies direct pressure to the urethra and/or bladder neck. In some embodiments of the invention, the cover is disposable. Optionally, the cover is sterilized between uses and is reusable. Optionally, the cover is decorated.

In some embodiments of the invention, the cover assists with removal of the device from the vagina. First, the cover optionally reduces friction between the incontinence device and the vaginal wall. Second, the cover is optionally provided with a removal device, such as a string. Optionally, the cover and the removal device are constructed of the same unitary piece of material. The removal device optionally assists with the removal of the device in a number of ways. Pulling the removal device causes tightening of the cover. Tightening of the cover causes the straightening of the vaginal walls. The straightening of the vaginal walls reduces the tent-like effect described above and relieves tension applied to the device, allowing for an easy and smooth removal of the device from the vagina. In addition, pulling on the removal device optionally causes the support and anchor arms to fold slightly towards the central axis of the incontinence device, thereby reducing the radial size of the incontinence device and allowing for an easy and smooth removal of the device from the vagina. In an exemplary embodiment of the invention, the device can be "walked"

out of the vagina by pulling on removal device causing the support arms to move towards the vaginal opening (and thereby pulling the anchor section along), releasing the string suddenly, and then repeating the process.

In some exemplary embodiments of the invention, lubricant is delivered by the incontinence device in response to a configuration change and/or during removal of the device. Optionally, lubricant is contained within the incontinence device.

FIGS. 22A-C show cross-sectional views of incontinence devices, which are by way of example only. In some exemplary embodiments of the invention, different cross-sectional configurations are used for manipulating the tension and compression stresses applied to incontinence devices during storage, deployment, use and/or removal. Optionally, different cross-sectional configurations are used for reducing resistance to certain motions of the incontinence device and/or increasing resistance to other motions. Optionally, different configurations are used for preventing necrosis and/or discomfort to the wearer. These Figures are used to show some of the many possibilities available for the shape and configuration of the devices described herein. For example, quadrilateral and ovoid shapes for the arms are not shown, but are also capable of use with the current inventions.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. When used in the following claims, the terms "comprises", "includes", "have" and their conjugates mean "including but not limited to". The scope of the invention is limited only by the following claims.

What is claimed is:

1. An apparatus for treating urinary incontinence comprising:
   a. a support section comprising at least one arm that provides urethral support;
   b. an anchoring section comprising at least one arm;
   c. a node positioned between the support section and the anchoring section;
   d. a removable insert separate from the support section and comprising an o-ring; and
   e. a removal device attached directly to the o-ring and the apparatus;
   wherein a portion of said insert is selectively positioned proximal to said support section and wherein said insert selectively provides at least support to said support section of said apparatus, and wherein a force exerted on the removal device will remove the insert from the apparatus.

2. The apparatus according to claim 1 wherein said insert provides pressure to said support section, causing radial expansion of said support section.

3. The apparatus according to claim 1 wherein said support section is flexible.

4. The apparatus according to claim 1 wherein the at least one arm of the support section is open-ended.

5. The apparatus according to claim 1 wherein the insert is removably positioned in a groove of the support section when the insert is providing support.

6. The apparatus according to claim 1 further comprising a cover.

7. The apparatus according to claim 6 wherein said cover encapsulates said apparatus.

* * * * *